US008507456B2

(12) United States Patent
Purschke et al.

(10) Patent No.: US 8,507,456 B2
(45) Date of Patent: Aug. 13, 2013

(54) C5A BINDING NUCLEIC ACIDS

(75) Inventors: Werner Purschke, Berlin (DE); Florian Jarosch, Berlin (DE); Dirk Eulberg, Berlin (DE); Sven Klussmann, Berlin (DE); Klaus Buchner, Berlin (DE); Christian Maasch, Berlin (DE)

(73) Assignee: NOXXON Pharma AG, Berlin (DE)

( * ) Notice: Subject to any disclaimer, the term of this patent is extended or adjusted under 35 U.S.C. 154(b) by 188 days.

(21) Appl. No.: 12/679,307

(22) PCT Filed: Sep. 24, 2008

(86) PCT No.: PCT/EP2008/008097

§ 371 (c)(1),
(2), (4) Date: Sep. 12, 2010

(87) PCT Pub. No.: WO2009/040113

PCT Pub. Date: Apr. 2, 2009

(65) Prior Publication Data

US 2011/0046207 A1 Feb. 24, 2011

(30) Foreign Application Priority Data

Sep. 24, 2007 (EP) .................................... 07018750

(51) Int. Cl.

| | |
|---|---|
| ***C07H 21/04*** | (2006.01) |
| ***C07H 21/02*** | (2006.01) |
| ***C12Q 1/68*** | (2006.01) |
| *C12N 5/00* | (2006.01) |

(52) U.S. Cl.
USPC ....... 514/44 A; 536/24.1; 536/23.1; 536/24.5; 435/6.1

(58) Field of Classification Search
None
See application file for complete search history.

(56) References Cited

U.S. PATENT DOCUMENTS

| | | | |
|---|---|---|---|
| 7,538,211 B2 | 5/2009 | Benedict et al. | |
| 7,579,456 B2 | 8/2009 | Benedict et al. | |
| 2006/0018871 A1 | 1/2006 | Benedict et al. | |
| 2006/0105980 A1 | 5/2006 | Benedict et al. | |
| 2007/0048248 A1 | 3/2007 | Benedict et al. | |
| 2007/0116710 A1 | 5/2007 | Bell et al. | |
| 2012/0065254 A1* | 3/2012 | Jarosch et al. .............. | 514/44 R |

OTHER PUBLICATIONS

Proctor et al., Recent . . . C5/C5a inhibitors, Exp Opin Ther Patents 16(4)445-458, 2006.
Nimjee et al., Apatamers . . . therapeutics, Ann Rev Med 56, 555-583, 2005.
Biesecker et al., Derivation of . . . complement C5, Immunopharm 42(1-3)219-230, 1999.
Eulberg et al., Development of . . . P antagonist, Nucl Acids Res 33(4)e45, 2005.
Eulberg et al., Spiegelmers: biostable aptamers, Chembiochem Eur J Chem Biol 4(10)979-983, 2003.
Search Report for EP2008/008097, Jan. 4, 2009.

* cited by examiner

*Primary Examiner* — Sean McGarry
(74) *Attorney, Agent, or Firm* — MDIP LLC

(57) ABSTRACT

The present invention is related to a nucleic acid, preferably binding to C5a, selected from the group comprising type A nucleic acids, type B nucleic acids, type C nucleic acids, type D nucleic acids and nucleic acids having a nucleic acid sequence according to any of SEQ.ID.No. 73 to 79.

67 Claims, 22 Drawing Sheets

Type A C5a binding nucleic acid 172-D7-000 and derivatives thereof

| Name | nt. | Sequence: 5'-3' | C | PD $K_D$ [nM] | FB $K_D$ [nM] | Ca $IC_{50}$ [nM] |
|---|---|---|---|---|---|---|
| 172-D7-000 | 49 | **AGCGUGCUU**GUCCGAUUGGCGGCA***CCC***UUGC***GGG***ACUGGG**GAGUACGCU** | = | 30 | 4.9 | 2-3 |
| | | | | | | |
| 172-D7-001 | 45 | **CGUGCUU**GUCCGAUUGGCGGCA***CCC***UUGC***GGG***ACUGGG**GAGUACG** | | 30 | | |
| 172-D7-002 | 43 | **GUGCUU**GUCCGAUUGGCGGCA***CCC***UUGC***GGG***ACUGGG**GAGUAC** | | 108 | | |
| 172-D7-003 | 49 | **AGCGUGCUC**GUCCGAUUGGCGGCA***CCC***UUGC***GGG***ACUGGG**GAGUACGCU** | | 372 | | |
| 172-D7-004 | 46 | **AGCGUGCUU**GUCCGA GCGGCA***CCC***UUGC***GGG***ACUGGG**GAGUACGCU** | | 153 | | |
| 172-D7-005 | 47 | **AGCGUGCUU**GUCCGAUUGGCGGCA***CCC***U C***GGG***ACUGGG**GAGUACGCU** | | 48 | | |
| 172-D7-008 | 43 | **CGUGCUU**GUCCGAUUGGCGGCA***CCC***U C***GGG***ACUGGG**GAGUACG** | | 22 | | |
| 172-D7-009 | 41 | **CGUGCUU**GUCCGAUUGGCGGCA***CCC*** ***GGG***ACUGGG**GAGUACG** | | 31 | | |
| 172-D7-010 | 45 | **CGCGCUU**GUCCGAUUGGCGGCA***CCC***UUGC***GGG***ACUGGG**GAGUGCG** | = | | | |
| 172-D7-011 | 45 | **CGCGCUU**GUCCGAUUGGCGGCA***CCC***UUGC***GGG***ACUGGG**GAGCGCG** | = | | | |

nucleotides that may hybridize to each other (bold) nt.: = nucleotides nucleotides which may mainly comprise a C5a-binding motif (boxed) (shaded): = C18-PEG-spacer

*nucleotides within the C5a binding motif that may hybridize to each other (bold and italic)*

C: = Clones were tested as aptamers in a competition binding assay vs. 172-D7-000

=: = equal binding affinity as AIT2-172-D7-000 <: = weaker binding affinity than 172-D7-000

PD.: = Clones were tested as aptamers in a pull-down binding assay to bind biotinylated human D-C5a

FB.: = Clones were tested as Spiegelmers in a filter binding assay to bind C5

Ca: = Clones were tested as Spiegelmers in a cell culture *in vitro* $Ca^{2+}$-release assay to inhibit human C5a

Fig. 1

Further derivatives of Type A C5a binding nucleic acid 172-D7-000

| Name | nt. | Sequence: 5'-3' | C | PD $K_D$ [nM] | FB $K_D$ [nM] | Ca $IC_{50}$ [nM] |
|---|---|---|---|---|---|---|
| 172-D7-000 | 49 | **AGCGUGCUU**GUCCGAUUGGCGGCA***CCC***UUGC***GGG***ACUGGG**GAGUACGCU** | = | 30 | 4.9 | 2-3 |
| | | | | | | |
| 172-D7-012 | 43 | **GCGCUU**GUCCGAUUGGCGGCA***CCC***UUGC***GGG***ACUGGG**GAGCGC** | = | | | |
| 172-D7-013 | 41 | **GCGCUU**GUCCGAUUGGCGGCA***CCC***U▒C***GGG***ACUGGG**GAGCGC** | = | 29 | 5.2 | 2-3 |
| 172-D7-014 | 39 | **GCGCUU**GUCCGAUUGGCGGCA***CCC***▒***GGG***ACUGGG**GAGCGC** | | 35 | | |
| 172-D7-015 | 37 | **GCGCUU**GUCCG▒UGGCGGCA***CCC***▒***GGG***ACUGGG**GAGCGC** | | 786 | | |
| 172-D7-016 | 37 | **GCGCUU**GUCCGAUU▒CGGCA***CCC***▒***GGG***ACUGGG**GAGCGC** | | 145 | | |
| 172-D7-017 | 37 | **GCGC-U**GUCCGAUUGGCGGCA***CCC***▒***GGG***ACUGGG**G-GCGC** | | 86 | | |
| 172-D7-018 | 37 | **GCGCUU**GUCCGAUUGGCGGCA***CC***▒***GG***ACUGGG**GAGCGC** | | 102 | | |
| | | | | | | |
| Type A Formula-1 | | GUCCGAUUGGCGGCA***CCC***UUGC***GGG***ACUGGG | | | | |

nucleotides that may hybridize to each other (bold) nt.: = nucleotides nucleotides which may mainly comprise a C5a-binding motif ▒: = C18-PEG-spacer

*nucleotides within the C5a binding motif that may hybridize to each other (bold and italic)*

C: = Clones were tested as aptamers in a competition binding assay vs. 172-D7-000

=: = equal binding affinity as 172-D7-000 <: = weaker binding affinity than 172-D7-000

PD.: = Clones were tested as aptamers in a pull-down binding assay to bind biotinylated human D-C5a

FB.: = Clones were tested as Spiegelmers in a filter binding assay to bind C5

Ca: = Clones were tested as Spiegelmers in a cell culture *in vitro* $Ca^{2+}$-release assay to inhibit human C5a

Fig. 2

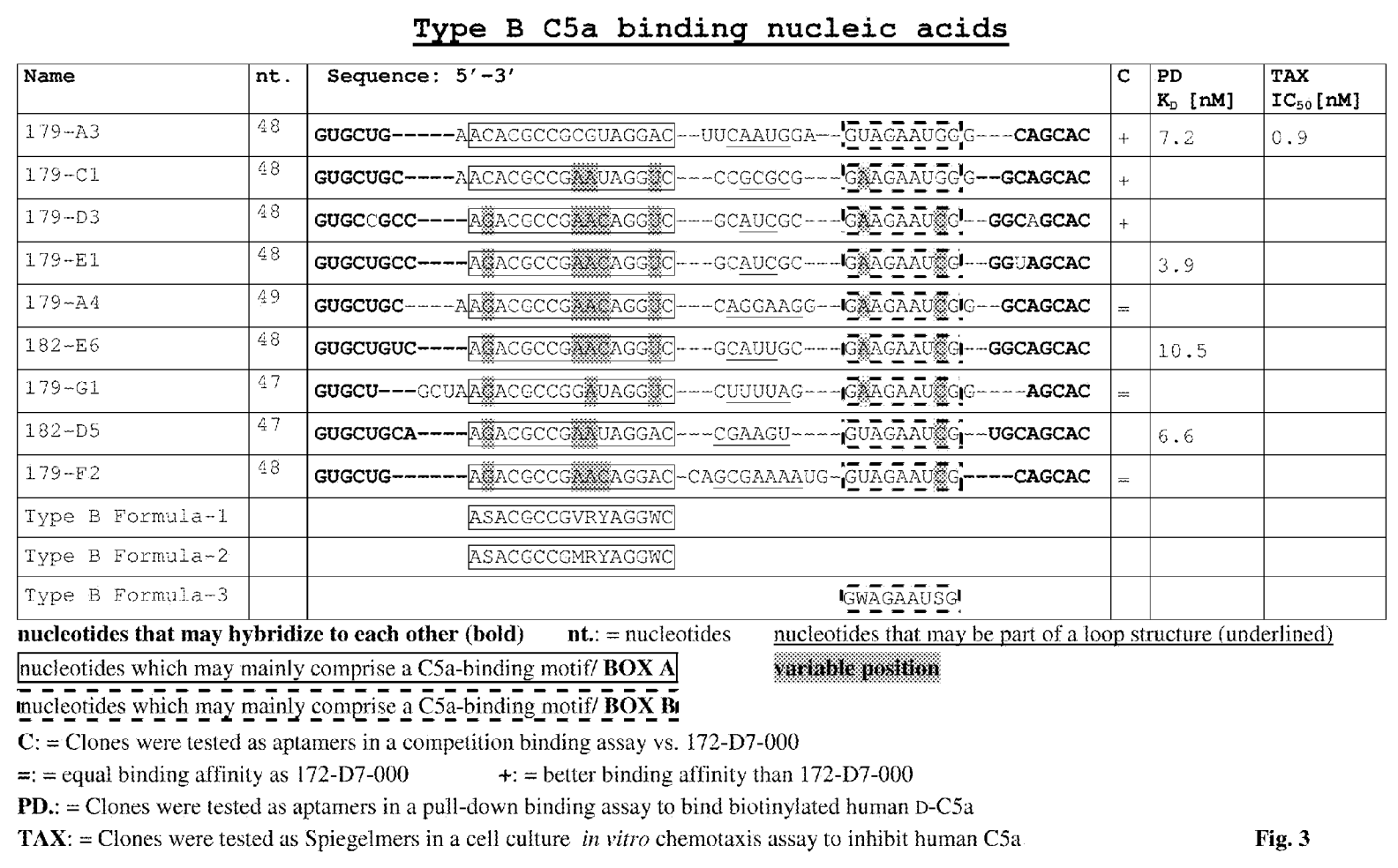

Type B C5a binding nucleic acids

| Name | nt. | Sequence: 5'-3' | C | PD $K_D$ [nM] | TAX $IC_{50}$ [nM] |
|---|---|---|---|---|---|
| 179-A3 | 48 | GUGCUG-----AACACGCCGCGUAGGAC--UUCAAUGGA--GUAGAAUGGG---CAGCAC | + | 7.2 | 0.9 |
| 179-C1 | 48 | GUGCUGC----AACACGCCGAAUAGGUC---CCGCGCG---GAAGAAUGGG--GCAGCAC | + | | |
| 179-D3 | 48 | GUGCCGCC----AGACGCCGAACAGGUC---GCAUCGC---GAAGAAUCG--GGCAGCAC | + | | |
| 179-E1 | 48 | GUGCUGCC----AGACGCCGAACAGGUC---GCAUCGC---GAAGAAUCG--GGUAGCAC | | 3.9 | |
| 179-A4 | 49 | GUGCUGC-----AAGACGCCGAACAGGUC---CAGGAAGG--GAAGAAUCGG--GCAGCAC | = | | |
| 182-E6 | 48 | GUGCUGUC----AGACGCCGAACAGGUC---GCAUUGC---GAAGAAUCG--GGCAGCAC | | 10.5 | |
| 179-G1 | 47 | GUGCU---GCUAAGACGCCGGAUAGGUC---CUUUUAG---GAAGAAUCGG----AGCAC | = | | |
| 182-D5 | 47 | GUGCUGCA----AGACGCCGAAUAGGAC---CGAAGU----GUAGAAUCG--UGCAGCAC | | 6.6 | |
| 179-F2 | 48 | GUGCUG------AGACGCCGAACAGGAC~CAGCGAAAAUG~GUAGAAUCG----CAGCAC | = | | |
| Type B Formula-1 | | ASACGCCGVRYAGGWC | | | |
| Type B Formula-2 | | ASACGCCGMRYAGGWC | | | |
| Type B Formula-3 | | GWAGAAUSG | | | |

nucleotides that may hybridize to each other (bold) nt.: = nucleotides nucleotides that may be part of a loop structure (underlined)

nucleotides which may mainly comprise a C5a-binding motif/ BOX A variable position nucleotides which may mainly comprise a C5a-binding motif/ BOX B

C: = Clones were tested as aptamers in a competition binding assay vs. 172-D7-000

=: = equal binding affinity as 172-D7-000 +: = better binding affinity than 172-D7-000

PD.: = Clones were tested as aptamers in a pull-down binding assay to bind biotinylated human D-C5a

TAX: = Clones were tested as Spiegelmers in a cell culture *in vitro* chemotaxis assay to inhibit human C5a

Fig. 3

Derivatives of Type B binding nucleic acid 179-A3

| Name | nt. | Sequence: 5'-3' | C | PD $K_D$ [nM] | FB $K_D$ [nM] | TAX $IC_{50}$ [nM] |
|---|---|---|---|---|---|---|
| 179-A3 | 48 | **GUGCUG**------AACACGCCGCGUAGGACUUCAAUGGAGUAGAAUGGG·······**CAGCAC** | | 7.2 | | 0.9 |
| | | | | | | |
| 179-A3-003 | 46 | **G-GCUG**-----AACACGCCGCGUAGGACUUCAAUGGAGUAGAAUGGG----**CAGC-C** | = | | | |
| 179-A3-007 | 44 | **GCUG**------AACACGCCGCGUAGGACUUCAAUGGAGUAGAAUGGG----**CAGC** | = | | | |
| 179-A3-008 | 42 | **CUG**------AACACGCCGCGUAGGACUUCAAUGGAGUAGAAUGGG----**CAG** | < | | | |
| 179-A3-014 | 44 | **G-GCUG**------AACACGCCGCGUAGGAC-CCAAUGG-GUAGAAUGGG-----**CAGC-C** | = | | 2.9 | 0.9 |
| 179-A3-042 | 41 | **G-GCUG**------AACACGCCGCGUAGGAC-CC▒GG-GUAGAAUGGG----**CAGC-C** | =* | | | |
| 179-A3-015 | 42 | **GCUG**------AACACGCCGCGUAGGAC-CCAAUGG-GUAGAAUGGG----**CAGC** | <* | | 9.3 | |
| 179-A3-020 | 42 | **GCGG**------AACACGCCGCGUAGGAC-CCAAUGG-GUAGAAUGGG----**CCGC** | <* | | | |
| 179-A3-021 | 42 | **GCUGC**------ACACGCCGCGUAGGAC-CCAAUGG-GUAGAAUGG·········**GCAGC** | =* | | | |

nucleotides that may hybridize to each other (bold) nt.: = nucleotides nucleotides which may mainly comprise a C5a-binding motif/ BOX A ▒: = C18-PEG-spacer nucleotides which may mainly comprise a C5a-binding motif/ BOX B

C: = Clones were tested as aptamers in a competition binding assay vs. 179-A3 or 179-A3-014 (*)

=: = equal binding affinity as 179-A3 or 179-A3-014 (*) <: = weaker binding affinity than 179-A3 or 179-A3-014 (*)

PD.: = Clones were tested as aptamers in a pull-down binding assay to bind biotinylated human D-C5a

FB.: = Clones were tested as Spiegelmers in a filter binding assay to bind C5

TAX: = Clones were tested as Spiegelmers in a cell culture *in vitro* chemotaxis assay to inhibit human C5a

Fig. 4

More derivatives of Type B binding nucleic acid 179-A3

| Name | nt. | Sequence: 5′-3′ | C |
|---|---|---|---|
| 179-A3-024 | 42 | **GGCU**------AACACGCCGCGUAGGAC-CCAAUGG-GUAGAAUGGG---**AGCC** | < |
| 179-A3-026 | 42 | **GGCC**------AACACGCCGCGUAGGAC-CCAAUGG-GUAGAAUGGG---**GGCC** | < |
| 179-A3-029 | 42 | **GCCC**------AACACGCCGCGUAGGAC-CCAAUGG-GUAGAAUGGG---**GGGC** | < |
| 179-A3-030 | 42 | **CGCC**------AACACGCCGCGUAGGAC-CCAAUGG-GUAGAAUGGG---**GGCG** | = |
| 179-A3-034 | 42 | **CCGG**------AACACGCCGCGUAGGAC-CCAAUGG-GUAGAAUGGG---**CCGG** | = |
| 179-A3-037 | 42 | **CGGG**------AACACGCCGCGUAGGAC-CCAAUGG-GUAGAAUGGG---**CCCG** | < |

nucleotides that may hybridize to each other (bold) nt.: = nucleotides nucleotides which may mainly comprise a C5a-binding motif/ BOX A nucleotides which may mainly comprise a C5a-binding motif/ BOX B

C: = Clones were tested as aptamers in a competition binding assay vs. 179-A3-014

=: = equal binding affinity as 179-A3-014 <: = weaker binding affinity than 179-A3-014

Fig. 5

Type C C5a binding nucleic acids

| Name | nt. | Sequence: 5'-3' | C |
|---|---|---|---|
| 185-H3-001 | 36 | **GCUGGG-C**GUGUUUACUUGCUUAAUAGGGG**G-CCCAGC** | ++ |
| 185-D3 | 36 | **GCUGGG-C**GUGUUUACUUGCUUAAUAGGGG**U-CCCAGC** | = |
| 185-B3 | 36 | **GCUGGG-C**GUGUUUACUUGCUUAAUAGGGG**G-CCUAGC** | = |
| 185-B1 | 36 | **GCUGGG-C**GUGUUUAUUUGCUUAAUAGGGG**G-UCCAGC** | < |
| 185-F4 | 36 | **GCUGGG-C**GUGUUUACUUGCUUAAUAGGGA**G-CCCAGC** | <* |
| 185-A3 | 36 | **GCUGGG-C**GUGUUUACUGGCUUAAUAGGGG**A-CCCAGC** | << |
| 185-B4 | 38 | **GCUGGGGA**GUGUUUACUUGCUUAAUAGGGG**UCCCCAGC** | = |
| 185-G4 | 38 | **GCUGGGGA**GUGUUUACUUGCUUAAUAGGGG**UCCUCAGC** | = |
| 185-H4 | 38 | **GCUGGGGA**GUGUUUACUUGCUUAAUAGGGA**UCCUUAGC** | < |
| 185-C3 | 38 | **GCUGAGGA**GUGUUUACUUGCUUAAUAGGGG**UCCCCAGC** | <* |
| | | | |
| Type C Formula-1 | 22 | GUGUUUAYUYGCUUAAUAGGGR | |
| Type C Formula-2 | 22 | GUGUUUACUUGCUUAAUAGGGG | |

nucleotides that may hybridize to each other (bold)

nucleotides which may mainly comprise a C5a-binding motif nt.: = nucleotides variable position

C: = Clones were tested as aptamers in a competition binding assay vs. 179-A3-015 (except from 185-F4 and 185-C3 that were tested in competition vs. 185-H3-001)

++: = much better binding affinity than 179-A3-015

=: = equal binding affinity as 179-A3-015

<: = weaker binding affinity than 179-A3-015

<*: = weaker binding affinity than 185-H3-001

<<: = much weaker binding affinity than 179-A3-015

Fig. 6

Derivatives of Type C C5a binding nucleic acid 185-H3-001 and 185-B4

| Name | nt. | Sequence: 5'-3' | C | PD $K_D$ [nM] | FB $K_D$ [nM] | TAX $IC_{50}$ [nM] | Ca $IC_{50}$ [nM] |
|---|---|---|---|---|---|---|---|
| 185-H3-001 | 36 | **GCUGGG-C**GUGUUUACUUGCUUAAUAGGGG**G-CCCAGC** | | 5 | 6.3 | 2-3 | 1-2 |
| 185-H3-005 | 34 | **CGUGG-C**GUGUUUACUUGCUUAAUAGGGG**G-CCACG** | < | | | | |
| 185-H3-006 | 34 | **CCGCG-C**GUGUUUACUUGCUUAAUAGGGG**G-CGCGG** | << | | | | |
| 185-H3-002 | 32 | **UGGG-C**GUGUUUACUUGCUUAAUAGGGG**G-CCCA** | < | | 4.3 | | |
| 185-H3-007 | 32 | **CGGG-C**GUGUUUACUUGCUUAAUAGGGG**G-CCCG** | < | | | | |
| 185-H3-014 | 32 | **GGGG-C**GUGUUUACUUGCUUAAUAGGGG**G-CCCC** | = | 6.5 | 4.2 | 1.5 | 1.8 |
| 185-B4-002 | 32 | **GGGG-A**GUGUUUACUUGCUUAAUAGGGG**U-CCCC** | < | | | | |
| 185-H3-003 | 30 | **GGG-C**GUGUUUACUUGCUUAAUAGGGG**G-CCC** | << | | 9.3 | | |
| 185-B4-003 | 30 | **GGG-A**GUGUUUACUUGCUUAAUAGGGG**U-CCC** | << | | | | |

nucleotides may hybridize to each other (bold) nt.:= nucleotides nucleotides which may mainly comprise a C5a-binding motif (boxed) =: = equal binding affinity as 185-H3-001

</<<: = weaker (<), or much weaker (<<) binding affinity than 185-H3-001

C: = Clones were tested as aptamers in a competition binding assay vs. 185-H3-001

PD.: = Clones were tested as aptamers in a pull-down binding assay to bind biotinylated human D-C5a

FB.: = Clones were tested as Spiegelmers in a filter binding assay to bind C5

TAX: = Clones were tested as Spiegelmers in a cell culture *in vitro* chemotaxis assay to inhibit human C5a

Ca: = Clones were tested as Spiegelmers in a cell culture *in vitro* $Ca^{2+}$-release assay to inhibit human C5a

Fig. 7

Type D C5a binding nucleic acids

| Name | nt. | Sequence: 5′-3′ | C | PD $K_D$ [nM] | FD $K_D$ [nM] | TAX $IC_{50}$ [nM] |
|---|---|---|---|---|---|---|
| 182-E5 | 48 | **GUACUGC**-GUUCGGACGUGGCAUGUUCCUUGACAAACGGUUG-**GCAGUAC** | + | 2.4 | 0.7 | 1.1 |
| 182-C5 | 48 | **GUGCUGC**-GUUCGGACGUGGCAUGUUCCUUGACAAACGGUUG-**GCAGCAC** | + | 2.2 | 2.2 | |
| 182-A8 | 48 | **GUGCUGG**-GUUCGGACGUGGCAUGUUCCUUGAUAAACGGUUG-**CCAGCAC** | | 3.2 | | |
| | | | | | | |
| Type D Formula-1 | | GUUCGGACGUGGCAUGUUCCUUGAYAAACGGUUG | | | | |

nucleotides that may hybridize to each other (bold) nt.: = nucleotides nucleotides which may mainly comprise a C5a-binding motif variable position

C: = Clones were tested as aptamers in a competition binding assay vs. 179-A3-014

+: = better binding affinity as 179-A3-014

PD.: = Clones were tested as aptamers in a pull-down binding assay to bind biotinylated human D-C5a

FB.: = Clones were tested as Spiegelmers in a filter binding assay to bind C5

TAX: = Clones were tested as Spiegelmers in a cell culture *in vitro* chemotaxis assay to inhibit human C5a

Fig. 8

Further nucleic acids binding to C5a

| Name | nt. | Sequence: 5′-3′ | C | PD $K_D$ [nM] |
|---|---|---|---|---|
| 179-B3 | 48 | **GUGUUGCGU**-AGAAUGGACAUAGAGGACACGCCGCGCAGG-**ACGCAGCAC** | + | |
| 179-A2 | 48 | **GUGCUGCGA**-AGAAUGGACAAAUCGUACACGCCGAGCAGG-**UCGCAGUAC** | + | |
| 182-A5 | 48 | **GUGCUG**-GACAGGACCAAGGUAAGGGCGGACCGAAAAACCUAG-**CAGCAC** | | 4.4 |
| 172-C5-000 | 49 | **AGCGUG**AACACGCCGAAUAGGUCCUAUAGGUGGGAAGAAUGGG**CACGCU** | | 56 |
| 173-A11-000 | 49 | **CCUGUGCGA**AGAAUGGGCCCUAGGGAACACGCCGAAAAGG**UUGCACAGG** | | 67 |
| 173-B12-000 | 48 | **CCUGUGC**GAAGCGCUCGGCGCAUACCGAUCAGGUCCGGCAA**GCACAGG** | | 79 |
| 171-B1-000 | 48 | **CGUGC**AACACGGCGAAUAGCGUCCUACAGUUAGGCAGAAUGGG**GCACG** | | 81 |

nucleotides that may hybridize to each other (bold) nt.: = nucleotides nucleotides which may mainly comprise a C5a-binding motif

C: = Clones were tested as aptamers in a competition binding assay vs. 172-D7-000

+: = better binding affinity as 172-D7-000

PD.: = Clones were tested as aptamers in a pull-down binding assay to bind biotinylated human D-C5a

Fig. 9

C5A BINDING NUCLEIC ACIDS

SEQUENCE LISTING

The instant application contains a Sequence Listing which has been submitted via EFS-Web and is hereby incorporated by reference in its entirety. Said ASCII copy, created on Jul. 7, 2010, is named 02131508.txt and is 78,824 bytes in size.

The present invention is related to nucleic acids binding to C5a and/or C5, and the use thereof for the manufacture of a medicament and a diagnostic agent, respectively.

The primary structure of the anaphylatoxin C5a (complement factor 5a; SwissProt entry P01031) was determined in 1978 (Fernandez and Hugli, 1978). It consists of 74 amino acids accounting for a molecular weight of 8,200 Da while the carbohydrate portion accounts for approximately 3,000 Da. The carbohydrate portion of C5a exists as a single complex oligosaccharide unit attached to an asparagine at position 64. The three disulfide bonds confer a stable, rigid structure to the molecule.

The tertiary structure of C5a was determined by NMR analysis. The protein consists of four helices juxtaposed in an approximately antiparallel topology connected by peptide loops located at the surface of the molecule (Zuiderweg et al., 1989).

Although the three-dimensional structure of C5a forms from different mammalian species has generally been maintained, the amino acid sequence has not particularly well been conserved during evolution. Sequence alignment results demonstrate 64% overall sequence identity with mouse C5a. Human C5a shares the following percentages of identical amino acids with C5a from:

| | |
|---|---|
| *Macaca mulatta* (rhesus monkey) | 85% |
| *Macaca fascicularis* (cynomolgus monkey) | 85% |
| *Bos taurus* (bovine) | 69% |
| *Sus scrofa* (pig) | 68% |
| *Mus musculus* (mouse) | 64% |
| *Rattus norvegicus* (rat) | 61% |

The more distantly related human proteins C3a and C4a share only 35 and 40% identity with C5a, respectively.

The complement system was discovered at the beginning of the last century as a heat sensitive serum fraction that "complemented" the antisera mediated lysis of cells and bacteria. Being a humoral component of the natural unspecific (innate) immune response, it plays an essential role in host defence against infectious agents and in the inflammatory process. Complement can be activated via three distinct pathways (i) after an antibody attaches itself to a cell surface or bacteria (referred as classical pathway), (ii) directly by bacterial or viral glycolipids (referred as alternative pathway), or (iii) by carbohydrates on bacteria (referred as lectin pathway). All these activation pathways converge at the point of activation of the complement component C5, where the common terminal pathway starts, culminating in assembly of the membrane attack complex (abbr. MAC). The complement system consists of more than 20 soluble proteins that function either as proteolytic enzymes or as binding proteins and making up about 10% of the total globulins in vertebrate serum. In addition, the complement system includes multiple distinct cell-surface receptors that exhibit specificity for proteolytic fragments of complement proteins and that are expressed by inflammatory cells and cells regulating the adaptive immune response. There are several regulatory proteins that inhibit complement activation and thus protect host cells from accidental complement attack. The complement system can become activated independently or together with the adaptive immune response.

The functions of complement include the process of opsonization (i.e. making bacteria more susceptible to phagocytosis), lysis of bacteria and foreign cells by inserting a pore into their membrane (referred as membrane attack complex), generation of chemotactically active substances, increase of vascular permeability, evocation of smooth muscle contraction, and promotion of mast cell degranulation. Similarly to the coagulation cascade, the process of complement activation is organized in sequential enzymatic steps also known as an enzymatic cascade (Sim and Laich, 2000). The detailed sequence of these interactions is outlined in the following:

Classical Pathway. This antibody-dependent activation pathway complements the specific antibody response. It is as elaborately controlled as the alternative pathway, but lacks the spontaneous initiation ability; i.e. the antibody-independent recognition function, and the feedback amplification mechanism. Among the activators of the classical pathway are antigen-antibody complexes, β-amyloid, DNA, polyinosinic acid, polyanion-polycation complexes like heparin/protamine, some enveloped viruses, monosodium urate crystals, lipid A of bacterial cell walls, plicatic acid, ant venom polysaccharide, subcellular membranes (such as mitochondria), as well as cell- and plasma-derived enzymes such as plasmin, kallikrein, activated Hageman factor, elastase or cathepsins. The antibody-induced classical pathway starts with C1, which binds to the Fc-fragment of an antibody (IgM>IgG3>IgG1>>IgG2) ligated to a cell surface antigen. C1 is a recognition complex composed of 22 polypeptide chains in 3 subunits; C1q, C1r, C1s. C1q is the actual recognition portion, a glycoprotein containing a collagen-like domain (exhibiting hydroxyproline and hydroxylysine residues) that looks like a bunch of tulips. Upon binding via C1q, C1r is activated to become a protease that cleaves C1s to a form that activates (by cleavage) both C2 and C4 to C2a/b and C4a/b. C2a and C4b combine to produce C4b2a, the C3 convertase (C3 activating enzyme). C4a has only weak anaphylatoxin activity but is not chemotactic. C3 is central to all three activation pathways. In the classical pathway, C4b2a convertase cleaves C3 into C3a/b. C3a is an anaphylatoxin. C3b combines with C4b2a to form C4b2a3b complex (C5 convertase). C3b can also bind directly to cells making them susceptible to phagocytosis (opsonization).

Alternative pathway. This pathway does not require antibodies for activation and is of major importance in host defence against bacterial and viral infection because—unlike the classical pathway—it is directly activated by surface structures of invading microorganisms such as bacterial/viral glycolipids or endotoxins. Other activators are inulins, rabbit erythrocytes, desialylated human erythrocytes, cobra venom factor, or phosphorothioate oligonucleotides. The six proteins C3, Factors B, D, H, I, and properdin together perform the functions of initiation, recognition and activation of the pathway which results in the formation of activator-bound C3/C5 convertase. The cascade begins with C3. A small amount of C3b is always found in circulation as a result of spontaneous cleavage of C3 ("C3-tickover"), but the concentrations are generally kept very low by subsequent degradation. However, when C3b binds covalently to sugars on a cell surface, it can serve as a nucleus for alternative pathway activation. Then Factor B binds to C3b. In the presence of Factor D, bound Factor B is cleaved to Ba and Bb; Bb contains the active site for a C3 convertase. Next, properdin binds to C3bBb to stabilize the C3bBb convertase on the cell surface leading to cleavage of further C3 molecules. Finally, the alternative C5 convertase C3bBb3b forms which cleaves C5 to C5a/b. Once present, C5b initiates assembly of the membrane attack complex as described above. Generally, only Gram-negative cells can be directly lysed by antibody plus complement; Gram-positive cells are mostly resistant. However, phagocytosis is greatly enhanced by opsonization with C3b (phagocytes have C3b receptors on their surface) and antibody is not always required. In addition, complement can neutralize virus particles either by direct lysis or by preventing viral penetration of host cells.

(3) Lectin pathway. The most recently discovered lectin or mannan-binding lectin (abbr. MBL) pathway depends on innate recognition of foreign substances (i.e., bacterial surfaces). This pathway has structural and functional similarities to the classical pathway. Activation of the lectin pathway is initiated by the acute phase protein MBL, which recognizes mannose on bacteria, IgA and probably structures exposed by damaged endothelium. MBL is homologous to C1q and triggers the MBL associated serine proteases (abbr. MASPs), of which the three forms MASP1, MASP2 and MASP3 have been described. Further lectin pathway activation is virtually identical to classical pathway activation forming the same C3 and C5 convertases. In addition there is some evidence that MASPs under some conditions may activate C3 directly.

(4) Terminal pathway. All three activation pathways converge in the formation of C5 convertase (C4b2a3b in the classical and lectin pathway, C3bBb3b in the alternative pathway), which cleaves C5 to C5a/b. C5a has potent anaphylatoxin activity and is chemotactic. The other C5 fragment C5b functions with its hydrophobic binding site as an anchor on the target cell surface to which the lytic membrane attack complex (MAC or terminal complement complex, abbr. TCC) forms. The MAC is assembled from five precursor proteins: C5b, C6, C7, C8, and C9. The final event is the formation of C9 oligomers, which insert themselves as transmembrane channels into the plasma membrane leading to osmotic lysis of the cell. MAC assembly is controlled by the soluble plasma factors S protein (also so known as vitronectin) and SP-40,40 (also so known as clusterin), and by CD59 and HRF (homologous restriction factor) on host cell membranes. Many kinds of cells are sensitive to complement mediated lysis: erythrocytes, platelets, bacteria, viruses possessing a lipoprotein envelope, and lymphocytes.

The complement system is a potent mechanism for initiating and amplifying inflammation. This is mediated through fragments of the complement components. Anaphylatoxins are the best defined fragments and are proteolytic fragments of the serine proteases of the complement system: C3a, C4a and C5a. Anaphylatoxins are not only produced in the course of complement activation, but also from activation of other enzyme systems which may directly cleave C3, C4 and C5. Such enzymes include plasmin, kallikrein, tissue and leukocyte lysosomal enzymes, and bacterial proteases. The anaphylatoxins have powerful effects on blood vessel walls, causing contraction of smooth muscle (e.g. ileal, bronchial, uterine and vascular muscle) and an increase in vascular permeability. These effects show specific tachyphylaxis (i.e. repeated stimulation induces diminishing responses) and can be blocked by antihistamines; they are probably mediated indirectly via release of histamine from mast cells and basophils. C5a is the 74-amino acid N-terminal cleavage product of the C5 plasmaprotein $\alpha$ chain. It is bound by the receptor C5aR (also known as C5R1 or CD88) with high affinity, a molecule present on many different cell types: most prominently on neutrophils, macrophages, smooth muscle cells, and endothelial cells. C5a is by far the most powerful anaphylatoxin, approximately 100 times more effective than C3a, and 1000 times more effective than C4a. This activity decreases in the order C5a>histamine>acetylcholine>C3a>>C4a.

C5a is extremely potent at stimulating neutrophil chemotaxis, adherence, respiratory burst generation and degranulation. C5a also stimulates neutrophils and endothelial cells to present more adhesion molecules; the intravenous injection of C5a, for example, quickly leads to neutropenia in animal experiments by triggering adherence of neutrophils to the blood vessel walls. Ligation of the neutrophil C5a receptor is followed by mobilization of membrane arachidonic acid which is metabolized to prostaglandins and leukotrienes including LTB4, another potent chemoattractant for neutrophils and monocytes. Following ligation of monocyte C5a receptors, IL-1 is released. Thus, the local release of C5a at sites of inflammation results in powerful pro-inflammatory stimuli. In fact, the release of C5a is connected directly or indirectly with many acute or chronic conditions, such as immune complex associated diseases in general (Heller et al., 1999); asthma (Kohl, 2001); septic shock (Huber-Lang et al., 2001); systemic inflammtory response syndrome (abbr. SIRS); multiorgan failure (abbr. MOF); acute respiratory distress syndrome (abbr. ARDS); inflammatory bowel syndrome (abbr. IBD) (Woodruff et al., 2003); infections; severe burns (Piccolo et al., 1999); reperfusion injury of organs such as heart, spleen, bladder, pancreas, stomach, lung, liver, kidney, limbs, brain, sceletal muscle or intestine (Riley et al., 2000); psoriasis (Bergh et al., 1993); myocarditis; multiple sclerosis (Muller-Ladner et al., 1996); and rheumatoid arthritis (abbr. RA) (Woodruff et al., 2002).

Numerous overviews over the relation between the complement system and diseases are published (Kirschfink, 1997; Kohl, 2001; Makrides, 1998; Walport, 2001a; Walport, 2001b).

Cell injury by complement occurs as a consequence of activation of either the classical or the alternative pathway on the surface of a cell. The MAC constitutes a supramolecular organisation that is composed of approximately twenty protein molecules and representing a molecular weight of approx. 1.7 million Da. The fully assembled MAC contains one molecule each of C5b, C6, C7, and C8 and several molecules of C9. All these MAC components are glycoproteins. When C5 is cleaved by C5 convertase and C5b is produced, self-assembly of the MAC begins. C5b and C6 form a stable and soluble bimolecular complex which binds to C7 and induces it to express a metastable site through which the nascent trimolecular complex (C5b-7) can insert itself into membranes, when it occurs on or in close proximity to a target lipid bilayer. Insertion is mediated by hydrophobic regions on the C5b-7 complex that appear following C7 binding to C5b-6. Membrane-bound C5b-7 commits MAC assembly to a membrane site and forms the receptor for C8. The binding of one C8 molecule to each C5b-7 complex gives rise to small trans-membrane channels of less than 1 nm functional diameter that may perturb target bacterial and erythrocyte membranes. Each membrane-bound C5b-8 complex acts as a receptor for multiple C9 molecules and appears to facilitate insertion of C9 into the hydrocarbon core of the cell membrane. Binding of one molecule of C9 initiates a process of C9 oligomerisation at the membrane attack site. After at least 12 molecules are incorporated into the complex, a discrete channel structure is formed. Therefore the end product consists of the tetramolecular C5b-8 complex (with a molecular weight of approximately 550 kDa) and tubular poly-C9 (with a molecular weight of approximately 1,100 kDa). This form of the MAC, once inserted into the cell membranes, creates complete transmembrane channels leading to osmotic lysis of the cell. The transmembrane channels formed vary in size depending on the number of C9 molecules incorporated into the channel structure. Whereas the presence of poly-C9 is not absolutely essential for the lysis of red blood cells or of nucleated cells, it may be necessary for the killing of bacteria.

The complement system is primarily beneficial in the body's defense against invading microorganisms. The early components of the complement cascade are important for opsonization, of infectious agents followed by their elimination from the body. In addition, they serve several normal functions of the immune system like controlling formation and clearance of immune complexes or cleaning up debris, dead tissues and foreign substances. All three activation pathways which recognize different molecular patterns that (in the healthy body) define an extensive array of non-self structures help controlling invaders. The terminal complement pathway—which culminates in the assembly of the MAC—represents a further line of defense by lysing bacteria and foreign cells.

The importance of a functional complement system becomes clear when the effects of complement deficiencies are considered. For example, individuals that are missing one of the alternative pathway proteins or late components (C3-C9) tend to get severe infections with pyogenic organisms, particularly *Neisseria* species. Deficiencies in the classical pathway components (such as C1, C2, C4) are also associated with increased, though not as strongly elevated, risk of infection. Complement components like C1 and MBL do also have the ability to neutralize viruses by interfering with the viral interaction with the host cell membrane, thus preventing entrance into the cell.

Of note, although cleavage of C5 leads to C5a as well as the MAC, the clinical features of C5 deficiency do not differ markedly from those of other terminal component deficiencies (e.g. C6, C7, C8, C9) suggesting that the absence of C5a does not contribute significantly to the clinical picture in C5-deficient patients. Therefore, the selective antagonisation of C5a promises to be the optimal leverage, so that the normal up- and downstream disease-preventing functions of complement remain intact. Thus, only the deleterious overproduction of the proinflammatory anaphylatoxin is blocked.

The fact that C5aR-deficient mice—although they are more susceptible for infections with *Pseudomonas aeruginosa*—appear otherwise normal, suggests that the blockade of C5a function does not have deleterious effects.

The problem underlying the present invention is to provide a means which specifically interacts with C5a. More specifically, the problem underlying the present invention is to provide for a nucleic acid based means which specifically interacts with C5a.

A further problem underlying the present invention is to provide a means for the manufacture of a medicament for the treatment of a human or non-human diseases, whereby the disease is characterized by C5a being either directly or indirectly involved in the pathogenetic mechanism of such disease.

A still further problem underlying the present invention is to provide a means for the manufacture of a diagnostic agent for the treatment of a disease, whereby the disease is characterized by C5a being either directly or indirectly involved in the pathogenetic mechanism of such disease.

These and other problems underlying the present invention are solved by the subject matter of the attached independent claims. Preferred embodiments may be taken from the dependent claims.

More specifically, the problem underlying the present invention is solved in a first aspect which is also a first embodiment, by a nucleic acid, capable of binding to C5a, selected from the group comprising type A nucleic acids, type B nucleic acids, type C nucleic acids, type D nucleic acids and nucleic acids having a nucleic acid sequence according to any of SEQ.ID.No. 73 to 79. The type A nucleic acids constitute a first subaspect of the first aspect, the type B nucleic acids constitute a second subaspect of the first aspect, the type C nucleic acids constitute a third subaspect of the first aspect, the type D nucleic acids constitute a fourth subaspect, and the nucleic acids having a nucleic acid sequence according to any of SEQ.ID.No. 73 to 79 constitute a fifth subaspect of the first aspect.

According to a first embodiment of the first subaspect, the type A nucleic acid comprises in 5'->3' direction a first stretch, a second stretch and a third stretch, whereby

- the first stretch and the third stretch optionally hybridize with each other, whereby upon hybridization a double-stranded structure is formed,
- the first stretch comprises five to nine nucleotides,
- the second stretch comprises a nucleotide sequence of GUCCGAUUGGCGGCACCCUUGCGGGACUGGG (SEQ ID NO: 20)
- the third stretch comprises five to nine nucleotides.

According to a second embodiment of the first subaspect which is also an embodiment of the first embodiment of the first subaspect, the nucleic acid comprises in 5'->3' direction a third stretch, a second stretch and a first stretch, whereby the first stretch and the third stretch optionally hybridize with each other, whereby upon hybridization a double-stranded structure is formed,

- the first stretch comprises five to nine nucleotides,
- the second stretch comprises a nucleotide sequence of GUCCGAUUGGCGGCACCCUUGCGGGACUGGG (SEQ ID NO: 20)
- the third stretch comprises five to nine nucleotides.

According to a third embodiment of the first subaspect which is also an embodiment of the first and second embodiment of the first subaspect, the second stretch is essential for bindung to C5a.

According to a fourth embodiment of the first subaspect which is also an embodiment of the first, second and third embodiment of the first subaspect, the double-stranded structure consists of five to nine basepairs.

According to a fifth embodiment of the first subaspect which is also an embodiment of the first, second, third and fourth embodiment of the first subaspect, the first stretch of nucleotides comprises a nucleotide sequence of 5' $X_1X_2X_3$GYGC$X_4$Y3' (SEQ ID NOS 173 and 190-191, respectively, in order of appearance) and the third stretch of nucleotides comprises a nucleotide sequence of 5' G$X_5$GYRC$X_6X_7X_8$ 3' (SEQ ID NO: 174 and 192-193, respectively, in order of appearance), whereby $X_1$ is A or absent,
$X_2$ is G or absent,
$X_3$ is C or absent,
$X_4$ is U,
$X_5$ is A,
$X_6$ is G or absent,
$X_7$ is C or absent, and
$X_8$ is U or absent, or
$X_1$ is A or absent,
$X_2$ is G or absent,
$X_3$ is C or absent,
$X_4$ is absent,
$X_5$ is absent,
$X_6$ is G or absent,
$X_7$ is C or absent, and
$X_8$ is U or absent,
preferably
$X_1$ is absent,
$X_2$ is absent,
$X_3$ is C or absent,
$X_4$ is U,
$X_5$ is A,
$X_6$ is G or absent,
$X_7$ is absent, and
$X_8$ is absent.

According to a sixth embodiment of the first subaspect which is also an embodiment of the fifth embodiment of the first subaspect, the first stretch of nucleotides comprises a nucleotide sequence of 5' $X_3$GYGC$X_4$U 3' (SEQ ID NO: 175) and the third stretch of nucleotides comprises a nucleotide sequence of 5' G$X_5$GYGC$X_6$ 3' (SEQ ID NO: 176), whereby
$X_3$ is C or absent,
$X_4$ is U,
$X_5$ is A, and
$X_6$ is G or absent.

According to a seventh embodiment of the first subaspect which is also an embodiment of any of the first to the sixth embodiment of the first subaspect, the second stretch comprises a first substretch and a second substretch and the first substretch and the second substrech can hybridize to each other whereby upon hybridization a double-stranded structure is formed.

According to an eighth embodiment of the first subaspect which is also an embodiment of the seventh embodiment of the first subaspect, each of the first and the second substrech comprises a sequence of three nucleotides and preferably the first substretch comprises the nucleotides at position 16 to 18 of the second stretch and the second substretch comprises the nucleotides 23 to 25 of the second stretch.

According to a ninth embodiment of the first subaspect which is also an embodiment of the eighth embodiment of the first subaspect, the sequence of three nucleotides for the first and the second substretch is independently CCC or GGG, under the proviso that the sequence of three nucleotides is different for the first and the second substretch.

According to a tenth embodiment of the first subaspect which is also an embodiment of the seventh, eighth and ninth embodiment of the first subaspect, the first substrech and the second substretch are separated within the second stretch by a separating stretch comprising a least three nucleotides or a spacer, whereby preferably the nucleotides of the separating stretch are not hybridized to each other.

According to an eleventh embodiment of the first subaspect which is also an embodiment of the tenth embodiment of the first subaspect, the separating stretch comprises at least three nucleotides, preferably consists of four nucleotides.

According to a twelfth embodiment of the first subaspect which is also an embodiment of the tenth and eleventh embodiment of the first subaspect, within the separating stretch a minimum of two nucleotides is replaced by a spacer.

According to a $13^{th}$ embodiment of the first subaspect which is also an embodiment of the tenth, eleventh and twelfth embodiment of the first subaspect, the separating stretch consists of a spacer.

According to a $14^{th}$ embodiment of the first subaspect which is also an embodiment of any of the tenth to $13^{th}$ embodiment of the first subaspect, the spacer is a hydrophilic spacer.

According to a $15^{th}$ embodiment of the first subaspect which is also an embodiment of the $14^{th}$ embodiment of the first subaspect, the hydrophilic spacer consists of polyethylene moieties.

According to a $16^{th}$ embodiment of the first subaspect which is also an embodiment of any of the first to the $15^{th}$ embodiment of the first subaspect, the nucleic acid comprises a nucleic acid sequence according to SEQ.ID.No 3, 11 to 13, 14 and 225, and 167 and 246.

According to a first embodiment of the second subaspect, the type B nucleic acid comprises in 5'->3' direction a first stretch, a second stretch Box A, a third stretch Box L, a fourth stretch Box B and a fifth stretch, whereby

- the first stretch and the fifth stretch optionally hybridize with each other, whereby upon hybridization a double-stranded structure is formed,
- the first stretch comprises four to eight nucleotides,
- the second stretch Box A comprises a nucleotide sequence of ASACGCCGVRYAGGWC (SEQ ID NO: 30),
- the third stretch Box L comprises four to eleven nucleotides,
- the fourth stretch Box B comprises a nucleotide sequence of GWAGAAUSG (SEQ ID NO: 32),
- the fifth stretch comprises four to eight nucleotides.

According to a second embodiment of the second subaspect which is also an embodiment of the first embodiment of the second subaspect, the arrangement of the second stretch Box A, the third stretch Box L and the fourth stretch Box B in 5'->3' direction is essential for bindung to C5a.

According to a third embodiment of the second subaspect which is also an embodiment of the first and the second embodiment of the second subaspect, the double-stranded structure consists of four to eight basepairs.

According to a fourth embodiment of the second subaspect which is also an embodiment of the first, second and third embodiment of the second subaspect, the first stretch and the second stretch Box A are separated by one to four nucleotides.

According to a fifth embodiment of the second subaspect which is also an embodiment of the first . second, third and fourth embodiment of the second subaspect, the first stretch and the second strech Box A are separatd by one nucleotide, whereby preferably said one nucleotide is A.

According to a sixth embodiment of the second subaspect which is also an embodiment of any of the first to the fifth embodiment of the second subaspect, the fourth stretch Box B and the fifth stretch are separated by one nucleotide, whereby preferably said one nucleotide is G.

According to a seventh embodiment of the second subaspect which is also an embodiment of any of the first to the sixth embodiment of the second subaspect, the first stretch and the second stretch Box A are separated by one nucleotide and the fourth stretch Box B and the fifth stretch are separated by one nucleotide and the one nucleotide separating the first stretch and the second stretch Box A, and the one nucleotide separating the fourth stretch Box B and the fifth stretch do not hybridize to each other.

According to an eighth embodiment of the second subaspect, the type B nucleic acid comprises in 5'->3' direction a fifth stretch, a second stretch Box A, a third stretch Box L, a fourth stretch Box B and a first stretch, whereby the first stretch and the fifth stretch optionally hybridize with each other, whereby upon hybridization a double-stranded structure is formed, whereby the first stretch comprises four to eight nucleotides, the second stretch Box A comprises a nucleotide sequence of ASACGCCGVRYAGGWC (SEQ ID NO: 30), the third stretch Box L comprises four to eleven nucleotides, the fourth stretch Box B comprises a nucleotide sequence of GWAGAAUSG (SEQ ID NO: 32), the fifth stretch comprises four to eight nucleotides.

According to a ninth embodiment of the second subaspect which is also an embodiment of the eighth embodiment of the second subaspect, the arrangement of the second stretch Box A, the third stretch Box L and the fourth stretch Box B in 5'->3' direction is essential for binding to C5a.

According to a tenth embodiment of the second subaspect which is also an embodiment of the eighth and the ninth embodiment of the second subaspect, the double-stranded structure consists of four to eight basepairs.

According to an eleventh embodiment of the second subaspect which is also an embodiment of the eighth, ninth and tenth embodiment of the second subaspect, the fifth stretch and the second stretch Box A are separated by one to four nucleotides.

According to a twelfth embodiment of the second subaspect which is also an embodiment of any of the eighth to the eleventh embodiment of the second subaspect, the fifth stretch and the second strech Box A are separatd by one nucleotide, whereby preferably said one nucleotide is A.

According to a $13^{th}$ embodiment of the second subaspect which is also an embodiment of any of the eighth to the twelfth embodiment of the second subaspect, the fourth stretch Box B and the first stretch are separated by one nucleotide, whereby preferably said one nucleotide is G.

According to a $14^{th}$ embodiment of the second subaspect which is also an embodiment of any of the eighth to the $13^{th}$ embodiment of the second subaspect, the fifth stretch and the second stretch Box A are separated by one nucleotide and the fourth stretch Box B and the first stretch are separated by one nucleotide and the one nucleotide separating the fifth stretch and the second stretch Box A, and the one nucleotide separating the fourth stretch Box B and the first stretch do not hybridize to each other.

According to a $15^{th}$ embodiment of the second subaspect which is also an embodiment of any of the eighth to the $14^{th}$ embodiment of the second subaspect,32. The nucleic acid molecule according to any of claims 18 to 31, whereby the first stretch of nucleotides comprise a nucleotide sequence of 5' $X_1X_2SBBX_3X_4X_5$ 3' (SEQ ID NOS 177 and 194-200, respectively, in order of appearance) and the fifth stretch of nucleotides comprise a nucleotide sequence of 5' $X_6X_7X_8VVSX_9X_{10}$ 3' (SEQ ID NOS 178 and 201-207, respectively, in order of appearance), whereby $X_1$ is G or absent,
$X_2$ is U or absent,
$X_3$ is B,
$X_4$ is Y,
$X_5$ is M,
$X_6$ is K,
$X_7$ is G,
$X_8$ is N,
$X_9$ is A or absent, and
$X_{10}$ is C or absent;

or $X_1$ is G or absent,
$X_2$ is U or absent,
$X_3$ is B,
$X_4$ is Y,
$X_5$ is absent,
$X_6$ is absent,
$X_7$ is G,
$X_8$ is N,
$X_9$ is A or absent, and
$X_{10}$ is C or absent;

or $X_1$ is G or absent,
$X_2$ is U or absent,
$X_3$ is B,
$X_4$ is absent,
$X_5$ is M,
$X_6$ is K,
$X_7$ is absent,
$X_8$ is N,
$X_9$ is A or absent, and
$X_{10}$ is C or absent;

or $X_1$ is G or absent,
$X_2$ is U or absent,
$X_3$ is absent,
$X_4$ is Y,
$X_5$ is M,
$X_6$ is K,
$X_7$ is G,
$X_8$ is absent,
$X_9$ is A or absent, and
$X_{10}$ is C or absent;

or $X_1$ is G or absent,
$X_2$ is U or absent,
$X_3$ is B,
$X_4$ is absent,
$X_5$ is absent,
$X_6$ is absent,
$X_7$ is absent,
$X_8$ is N,
$X_9$ is A or absent, and
$X_{10}$ is C or absent;

or $X_1$ is G or absent,
$X_2$ is U or absent,
$X_3$ is absent,
$X_4$ is absent,
$X_5$ is M,
$X_6$ is K,
$X_7$ is absent,
$X_8$ is absent,
$X_9$ is A or absent, and
$X_{10}$ is C or absent, or $X_1$ is G or absent,
$X_2$ is U or absent,
$X_3$ is absent,
$X_4$ is Y,
$X_5$ is absent,
$X_6$ is absent,
$X_7$ is G,
$X_8$ is absent,
$X_9$ is A or absent, and
$X_{10}$ is C or absent;

or $X_1$ is G or absent, $X_2$ is U or absent, $X_3$ is absent, $X_4$ is absent, $X_5$ is absent, $X_6$ is absent, $X_7$ is absent, $X_8$ is absent, $X_9$ is A or absent, and $X_{10}$ is C or absent.

According to a 16$^{th}$ embodiment of the second subaspect which is also an embodiment of the 15$^{th}$ embodiment of the second subaspect, the first stretch of nucleotides comprise a nucleotide sequence of 5' $X_1X_2$SSB$X_3X_4X_5$ 3' (SEQ ID NOS 188 and 208, respectively, in order of appearance) and the fifth stretch of nucleotides comprise a nucleotide sequence of 5' $X_6X_7X_8$VSS$X_9X_{10}$ 3' (SEQ ID NOS 189 and 209, respectively, in order of appearance), whereby $X_1$ is G or absent, $X_2$ is U or absent, $X_3$ is S, $X_4$ is absent, $X_5$ is absent, $X_6$ is absent, $X_7$ is absent, $X_8$ is S, $X_9$ is A or absent, and $X_{10}$ is C or absent;

whereby preferably $X_1$ is absent, $X_2$ is absent, $X_3$ is S, $X_4$ is absent, $X_5$ is absent, $X_6$ is absent, $X_7$ is absent, $X_8$ is S, $X_9$ is absent, and $X_{10}$ is absent.

According to a 17$^{th}$ embodiment of the second subaspect which is also an embodiment of the 15$^{th}$ and the 16$^{th}$ embodiment of the second subaspect, the first stretch of nucleotides comprise a nucleotide sequence of 5' GCUG 3' and the fifth stretch of nucleotides comprise a nucleotide sequence of 5' CAGC 3' or whereby the first stretch of nucleotides comprise a nucleotide sequence of 5' CGCC 3' and the fifth stretch of nucleotides comprise a nucleotide sequence of 5' GGCG 3' or whereby the first stretch of nucleotides comprise a nucleotide sequence of 5' CCGG 3' and the fifth stretch of nucleotides comprise a nucleotide sequence of 5' CCGG 3'.

According to an 18$^{th}$ embodiment of the second subaspect which is also an embodiment of the 15$^{th}$ embodiment of the second subaspect, the first stretch of nucleotides comprises a nucleotide sequence of 5' $X_1X_2$GCV$X_3X_4X_5$ 3' (SEQ ID NO: 210) and the fifth stretch of nucleotides comprises a nucleotide sequence of 5' $X_6X_7X_8$AGC$X_9X_{10}$ 3' (SEQ ID NO: 180), whereby $X_1$ is G or absent, $X_2$ is U or absent, $X_3$ is G, $X_4$ is C, $X_5$ is absent, $X_6$ is absent, $X_7$ is G, $X_8$ is C, $X_9$ is A or absent, and $X_{10}$ is C or absent.

According to a 19$^{th}$ embodiment of the second subaspect which is also an embodiment of the 15$^{th}$ embodiment of the second subaspect, the first stretch of nucleotides comprise a nucleotide sequence of 5' $X_1X_2$GCC$X_3X_4X_5$ 3' (SEQ ID NO: 181) and the fifth stretch of nucleotides comprise a nucleotide sequence of 5' $X_6X_7X_8$AGC$X_9X_{10}$ 3' (SEQ ID NO: 211), whereby $X_1$ is G or absent, $X_2$ is U or absent, $X_3$ is G, $X_4$ is C, $X_5$ is C, $X_6$ is G, $X_7$ is G, $X_8$ is C, $X_9$ is A or absent, and $X_{10}$ is C or absent.

According to a 20$^{th}$ embodiment of the second subaspect which is also an embodiment of any of the first to the 19$^{th}$ embodiment of the second subaspect, the second nucleotide at the 5'-end of the second stretch Box A is C and the penultimate nucleotide at the 3'-end of the fourth stretch Box B is G or the second nucleotide at the 5'-end of the second stretch Box A is G and the penultimate nucleotide at the 3'-end of the fourth stretch Box B is C.

According to a 21$^{st}$ embodiment of the second subaspect which is also an embodiment of any of the first to the 20$^{th}$ embodiment of the second subaspect, the penultimate nucleotide at the 3'-end of the second stretch Box A is A and the second nucleotide at the 5'-end of the fourth stretch Box B is U or the penultimate nucleotide at the 3'-end of the second stretch Box A is U and the second nucleotide at the 5'-end of the fourth stretch Box B is A.

According to a 22nd embodiment of the second subaspect which is also an embodiment of any of the first to the 21$^{st}$ embodiment of the second subaspect, the second stretch Box A comprises a nucleotide sequence of ASACGCCGMRYAGGWC (SEQ ID NO: 31), preferably a nucleotide sequence of ACACGCCGCGUAGGAC (SEQ ID NO: 212).

According to a 23$^{rd}$ embodiment of the second subaspect which is also an embodiment of any of the first to the 22nd embodiment of the second subaspect, the fourth stretch Box B comprises a nucleotide sequence of GUAGAAUGG (SEQ ID NO: 213).

According to a 24$^{th}$ embodiment of the second subaspect which is also an embodiment of any of the first to the 23rd embodiment of the second subaspect, the third stretch Box L comprises a first substretch and a second substretch and the first substretch and the second substrech hybridize to each other whereby upon hybridization a double-stranded structure is formed.

According to a 25$^{th}$ embodiment of the second subaspect which is also an embodiment of the 24$^{th}$ embodiment of the second subaspect, the sequence of the first and the second substretch is independently CC or GG, under the proviso that the sequence of the nucleotides is different for the first and the second substretch.

According to a 26$^{th}$ embodiment of the second subaspect which is also an embodiment of any of the 24$^{th}$ and 25$^{th}$ embodiment of the second subaspect, the first substrech and the second substretch are separated within the second stretch by a separating stretch comprising a spacer or a nucleotide sequence of AAU whereby preferably the nucleotides of the separating stretch are not hybridized to each other.

According to a $27^{th}$ embodiment of the second subaspect which is also an embodiment of any of the $26^{th}$ embodiment of the second subaspect, the separating stretch a minimum of two nucleotides is replaced by a spacer.

According to a $28^{th}$ embodiment of the second subaspect which is also an embodiment of any of the $26^{th}$ and the $27^{th}$ embodiment of the second subaspect, the separating stretch consists of a spacer.

According to a $29^{th}$ embodiment of the second subaspect which is also an embodiment of any of the first to the $28^{th}$ embodiment of the second subaspect, the spacer is a hydrophilic spacer.

According to a $30^{th}$ embodiment of the second subaspect which is also an embodiment of any of the first to the $29^{th}$ embodiment of the second subaspect, the hydrophilic spacer consists of polyethylene moieties.

According to a $31^{st}$ embodiment of the second subaspect which is also an embodiment of any of the first to the $30^{th}$ embodiment of the second subaspect, the nucleic acid comprises a nucleic acid sequence according to SEQ.ID.No 21 to 23, 33, 34, 36, 37 and 232, 40, 46, 47 and 168.

According to a first embodiment of the third subaspect, the type C nucleic acid comprises in 5'->3' direction a first stretch, a second stretch and a third stretch, whereby

- the first stretch and the third stretch optionally hybridize with each other, whereby upon hybridization a double-stranded structure is formed,
- the first stretch comprises five to eight nucleotides,
- the second stretch comprises a nucleotide sequence of GUGUUUAYUYGCUUAAUAGGGR (SEQ ID NO: 59),
- the third stretch comprises five to eight nucleotides.

According to a second embodiment of the third subaspect which is also an embodiment of the first embodiment of the third subaspect, the type C nucleic acid comprises in 5'->3' direction a third stretch, a second stretch and a first stretch, whereby

- the first stretch and the third stretch optionally hybridize with each other, whereby upon hybridization a double-stranded structure is formed,
- the first stretch comprises five to eight nucleotides,
- the second stretch comprises a nucleotide sequence of GUGUUUAYUYGCUUAAUAGGGR (SEQ ID NO: 59),
- the third stretch comprises five to eight nucleotides.

According to a third embodiment of the third subaspect which is also an embodiment of the first and second embodiment of the third subaspect, the second stretch is essential for bindung to C5a.

According to a fourth embodiment of the third subaspect which is also an embodiment of the first, second and third embodiment of the third subaspect, the double-stranded structure consists of five to eight base pairs.

According to a fifth embodiment of the third subaspect which is also an embodiment of any of the first to the fourth embodiment of the third subaspect, the first and third stretch each and independently comprises five nucleotides.

According to a sixth embodiment of the third subaspect which is also an embodiment of any of the first to the fifth embodiment of the third subaspect, the first stretch of nucleotides comprise a nucleotide sequence of 5' $X_1X_2X_3$ KVG$X_4$M 3' (SEQ ID NOS 182 and 214-215, respectively, in order of appearance) and the third stretch of nucleotides comprise a nucleotide sequence of 5' D$X_5$YBH$X_6X_7X_8$ 3' (SEQ ID NOS 183 and 216-217, respectively, in order of appearance).

whereby $X_1$ is G or absent,
$X_2$ is C or absent,
$X_3$ is B or absent,
$X_4$ is G,
$X_5$ is C,
$X_6$ is V or absent,
$X_7$ is G or absent,
$X_8$ is C or absent;

or $X_1$ is G or absent,
$X_2$ is C or absent,
$X_3$ is B or absent,
$X_4$ is absent,
$X_5$ is absent,
$X_6$ is V or absent,
$X_7$ is G or absent,
$X_8$ is C or absent.

According to a seventh embodiment of the third subaspect which is also an embodiment of the sixth embodiment of the third subaspect, $X_1$ is G,
$X_2$ is C,
$X_3$ is B,
$X_4$ is absent,
$X_5$ is absent,
$X_6$ is V,
$X_7$ is G,
$X_8$ is C.

According to an eighth embodiment of the third subaspect which is also an embodiment of the sixth and seventh embodiment of the third subaspect, the first stretch of nucleotides comprise a nucleotide sequence of 5' GGGGC 3' and the third stretch of nucleotides comprise a nucleotide sequence of 5' GCCCC 3'.

According to a ninth embodiment of the third subaspect which is also an embodiment of any of the first to the eighth embodiment of the third subaspect, the second stretch comprises a nucleotide sequence of GUGUUUACUUGCUUAAUAGGGG (SEQ ID NO: 60).

According to a tenth embodiment of the third subaspect which is also an embodiment of any of the first to the ninth embodiment of the third subaspect, the nucleic acid comprises a nucleic acid sequence according to SEQ.ID.No 49, 65, 170 and 171.

According to a first embodiment of the fourth subaspect, the type D nucleic acid comprises in 5'->3' direction a first stretch, a second stretch and a third stretch, whereby

- the first stretch and the third stretch optionally hybridize with each other, whereby upon hybridization a double-stranded structure is formed,
- the first stretch comprises seven nucleotides,
- the second stretch comprises a nucleotide sequence of GUUCGGACGUGGCAUGUUCCUUGAYAAACGGUUG (SEQ ID NO: 72),
- the third stretch comprises seven nucleotides.

According to a second embodiment of the fourth subaspect which is also an embodiment of the first embodiment of the fourth subaspect, the type D nucleic acid comprises in 5'->3' direction a third stretch, a second stretch and a first stretch

- the first stretch and the third stretch optionally hybridize with each other, whereby upon hybridization a double-stranded structure is formed,
- the first stretch comprises seven nucleotides, the second stretch comprises a nucleotide sequence of GUUCGGACGUGGCAUGUUCCU-UGAYAAACGGUUG (SEQ ID NO: 72), the third stretch comprises seven nucleotides.

According to a third embodiment of the fourth subaspect which is also an embodiment of the first and second embodiment of the fourth subaspect, the second stretch is essential for bindung to C5a and/or C5.

According to a fourth embodiment of the fourth subaspect which is also an embodiment of the first, second and third embodiment of the fourth subaspect, the double-stranded structure consists of seven basepairs.

According to a fifth embodiment of the fourth subaspect which is also an embodiment of the fourth embodiment of the fourth subaspect, the second stretch comprises a nucleotide sequence of GUUCGGACGUGGCAUGUUCCUUGA-CAAACGGUUG (SEQ ID NO: 218).

According to a sixth embodiment of the fourth subaspect which is also an embodiment of any of the first to the fifth embodiment of the fourth subaspect, the nucleic acid comprises a nucleic acid sequence according to SEQ.ID.No 69 to 71.

In an embodiment of the first, second, third, fourth and fifth subaspect of the first aspect, the nucleic acid is capable of binding C5a and C5, preferably glycosylated C5a and glycosylated C5.

In a further embodiment of the first, second, third, fourth and fifth subaspect of the first aspect, the nucleic acid is capable of binding C5 and/or C5a, whereby the C5 and/or C5a is human, monkey, horse, rabbit, bovine, canine, poraine C5 and/or C5a, preferably human C5 and/or human C5a.

In an embodiment of the first, second, third, fourth and fifth subaspect of the first aspect, the C5a has an amino acid sequence according to SEQ ID No. 1.

In an embodiment of the first, second, third, fourth and fifth subaspect of the first aspect, the C5 has two chains, an alpha and a beta chain, and the nucleic acid is capable of binding the alpha chain of C5 whereby the alpha chain of C5 has an amino acid sequence according to SEQ ID No. 171.

In an embodiment of the first, second, third, fourth and fifth subaspect of the first aspect, the nucleic acid comprises a modification group, whereby the modification group is preferably a high molecular weight moiety and/or whereby the modification group preferably allows to modify the characteristics of the nucleic acid according to the any embodiment of the first, second, third, fourth and fifth subaspect of the first aspect in terms of residence time in the animal or human body, preferably the human body.

In a preferred embodiment such modification group is selected from the group comprising a HES moiety and a PEG moiety or biodegradable modifications.

In a more preferred embodiment the modification group is a PEG moiety consisting of a straight or branched PEG, whereby the molecular weight of the PEG moiety is preferably from about 20,000 to 120,000 Da, more preferably from about 30,000 to 80,000 Da and most preferably about 40,000 Da.

In an alternative more preferred embodiment the modification group is a HES moiety, whereby preferably the molecular weight of the HES moiety is from about 10,000 to 200,000 Da, more preferably from about 30,000 to 170.000 Da and most preferably about 150,000 Da.

In a still further embodiment the modification is coupled to the nucleic acid via a linker, whereby the linker is linker or a biodegradable linker.

In an embodiment the modification group is coupled to the nucleic acid the 5'-terminal nucleotide and/or the 3'-terminal nucleotide of the nucleic acid and/or to a nucleotide of the nucleic acid between the 5'-terminal nucleotide of the nucleic acid and the 3'-terminal nucleotide of the nucleic acid.

In an embodiment the nucleotides of or the nucleotides forming the nucleic acid are L-nucleotides.

In an embodiment of the first, second, third, fourth and fifth subaspect of the first aspect, the nucleic acid is an L-nucleic acid.

In a preferred embodiment the nucleic acid comprises at least one moiety which is capable of binding C5a, whereby such moiety consists of L-nucleotides.

The problem underlying the present invention is solved in a second aspect which is also a first embodiment of the second aspect, by a nucleic acid according to any embodiment of the first, second, third, fourth and fifth subaspect of the first aspect for the manufacture of a medicament for the treatment and/or prevention of a disease or for use in a method for the treatment and/or prevention of a diseases, more preferably a disease or condition described herein in connection with other aspects of the instant invention.

The problem underlying the present invention is solved in a third aspect which is also a first embodiment of the third aspect, by a pharmaceutical composition comprising a nucleic acid according to any embodiment of the first, second, third, fourth and fifth subaspect of the first aspect and optionally a further constituent, whereby the further constituent is selected from the group comprising pharmaceutically acceptable excipients, pharmaceutically acceptable carriers and pharmaceutically active agents.

In a second embodiment of the third aspect which is also an embodiment of the first embodiment of the third aspect, the pharmaceutical composition comprises a nucleic acid according to any embodiment of the first and second aspect and a pharmaceutically acceptable carrier.

The problem underlying the present invention is solved in a fourth aspect which is also a first embodiment of the fourth aspect by the use of a nucleic acid according to any of embodiment of the first and second aspect for the manufacture of a medicament.

In a second embodiment of the fourth aspect which is also an embodiment of the first embodiment of the fourth aspect, the medicament is for use in human medicine or for use in veterinary medicine.

The problem underlying the present invention is solved in a fifth aspect which is also a first embodiment of the fifth aspect by the use of a nucleic acid according to any of embodiment of the first and second aspect for the manufacture of a diagnostic means.

In a third embodiment of the fourth aspect which is also an embodiment of the first embodiment of the fourth aspect, the medicament is for the treatment and/or prevention of a disease or disorder selected from the group comprising autoimmune diseases, inflammatory diseases, infectious diseases, immune complex associated diseases, disease of the eye, local inflammations, shock, sarcoidosis, septic shock, haemorrhagic shock, anaphylactic shock, systemic inflammatory response syndrome, multiple organ failure, asthma, allergy, vasculitides, whereby such vasculitis is preferably arteritis temporalis, vasculitis, vascular leakage, and atherosclerosis; myocarditis, dermatomyositis, acute respiratory insufficiency, stroke, myocardial infarction, burn, local manifestations of systemic diseases, type 1 and 2 diabetes, the manifestations of diabetes, thromboembolism, glomerulonephritis, immune complex disorders, fetal rejection, adult respiratory distress syndrome, chronic obstructive pulmonary disease, pancreatitis, peritonitis, gingivitis and the secondary damages of trauma, systemic inflammatory response syndrome, multiorgan failure, neurodegeneration and inflammation such as in Alzheimer's disease, neurocognitive dysfunction, acute injuries of the central nervous system.

In a fourth embodiment of the fourth aspect which is also an embodiment of the third embodiment of the fourth aspect, the disease is an autoimmune disease selected from the group comprising rheumatoid arthritis, ankylosing spodylitis, systemic lupus erythematosus, multiple sclerosis, psoriasis, urticaria, alopecia greata, warm and cold autoimmune hemolytic anemia, pernicious anemia, autoimmune adrenalitis, autoimmune neurodegeneration, such as chronic inflammatory demyelinating polyneuropathy and multiple sclerosis; Churg-Strauss syndrome, Cogan syndrome, CREST syndrome, pemphigus vulgaris and pemphigus foliaceus, bullous pemphigoid, polymyalgia rheumatica, polymyositis, primary biliary cirrhosis, psoriatic arthritis, rheumatic fever, sarcoidosis, Sjörgensen syndrome, scleroderma, celiac disease, stiff-man syndrome, Takayasu arteritis, transient gluten intolerance, autoimmune uveitis, vitiligo, polychondritis, dermatitis herpetiformis or Duhring's disease, fibromyalgia, Goodpasture syndrome, Guillain-Barré syndrome, Hashimoto thyroiditis, autoimmune hepatitis, inflammatory bowel disease auch asCrohn's disease, colitis ulcerosa; myasthenia gravis, glomerulonephritis, renal fibrosis, polyarteritis nodosa, anti-phospholipid syndrome, polyglandular autoimmune syndrome, idiopatic pulmonar fibrosis, idiopathic thrombocytopenic purpura, autoimmune infertility, juvenile rheumatoid arthritis, autoimmune cardiomyopathy, rheumatic disease in the eye, rheumatic disease in the brain, rheumatic disease in the vasculature, rheumatic disease in the heart, rheumatic disease in the lung, rheumatic disease in the kidneys, rheumatic disease in the liver, rheumatic disease in the gastrointestinal tract, rheumatic disease in the spleen, rheumatic disease in the skin, rheumatic disease in the bones, rheumatic disease in the lymphatic system, rheumatic disease in the blood or other organ systems, Lambert-Eaton syndrome, lichen sclerosis, Lyme disease, Graves disease, Behçet's disease, Ménière's disease, reactive arthritis.

In a fifth embodiment of the fourth aspect which is also an embodiment of the third embodiment of the fourth aspect, the disease is an inflammatory disease selected from the group of inflammatory diseases of the eye and inflammatory diseases of the vasculature.

In a sixth embodiment of the fourth aspect which is also an embodiment of the third embodiment of the fourth aspect, the disease is an infectious disease caused by or associated with viruses, preferably HIV, HBV, HCV, CMV, or intracellular parasites, preferably *Leishmania, Rickettsia, Chlamydia, Coxiella, Plasmodium, Brucella*, mycobacteria, *Listeria, Toxoplasma* and *Trypanosoma*.

In a seventh embodiment of the fourth aspect which is also an embodiment of the third embodiment of the fourth aspect, the disease is an immune complex associated disease selected from the group of immune-complex-mediated renal diseases such as a complication of systemic erythematosus.

In an eighth embodiment of the fourth aspect which is also an embodiment of the third embodiment of the fourth aspect, the disease is a disease of the eye selected from the group comprising uveitis, age-related macular degeneration (AMD), diabetic retinopathy, diabetic macular edema, retinal vessel occlusion, choroidal neovacularization, glaucoma ocular pemphigoid, keratoconjunctivitis, Stevens-Johnson syndrome, and Graves ophthalmopathy.

In a ninth embodiment of the fourth aspect which is also an embodiment of the first embodiment of the fourth aspect, the medicament is for the prevention and/or support and/or post-operative treatment during and/or after surgery, prefereably during and/or aftercoronary artery bypass graft, off-pump coronary artery bypass graft, minimally invasive direct coronary artery bypass graft, percutaneous transluminal coronary angioplasty, thrombolysis, organ transplantation, brain and spinal cord surgery, reconstructive surgery and vessel clamping surgery.

The problem underlying the present invention is solved in a sixth aspect which is also a first embodiment of the sixth aspect, by the use of a nucleic acid according to any embodiment of the first and the second aspect for the prevention of organ damage of a transplanted organ or of an organ to be transplanted or for use of prevention of treatment of transplant rejection for a transplanted organ, whereby such organ is preferably selected from the group comprising liver, kidney, intestine, lung, heart, skin, limb, cornea, Langerhans islet, bone marrow, blood vessels and pancreas.

The problem underlying the present invention is solved in a seventh aspect which is also a first embodiment of the seventh aspect, by the use of a nucleic acid according to any embodiment of the first and the second aspect for the prevention of reperfusion injury of organs such as heart, spleen, bladder, pancreas, stomach, lung, liver, kidney, limbs, brain, sceletal muscle or intestine and of delayed graft function.

The problem underlying the present invention is solved in an eighth aspect which is also a first embodiment of the eighth aspect, by a storage solution and/or a transport solution, preferably for storage of an organ or transport of an organ, comprising a nucleic acid according to any embodiment of the first and second aspect.

The problem underlying the present invention is solved in a ninth aspect which is also a first embodiment of the ninth aspect, by a complex comprising a nucleic acid according to any embodiment of the first and second aspect, whereby preferably the complex is a crystalline complex.

In a second embodiment of the ninth aspect which is also an embodiment of the first embodiment of the ninth aspect, the C5a is selected from the group comprising human C5a, monkey C5a, horse C5a, rabbit C5a, bovine C5a, canine C5a and porcine C5a, more preferably C5a is human C5a.

In a third embodiment of the ninth aspect which is also an embodiment of the first embodiment of the ninth aspect, the C5 is selected from the group comprising human C5, monkey C5, horse C5, rabbit C5, bovine C5, canine C5 and porcine C5, more preferably C5 is human C5.

The problem underlying the present invention is solved in a tenth eighth aspect which is also a first embodiment of the tenth aspect, by the use of nucleic acid according to any embodiment of the first and second aspect for the detection of C5 and/or C5a.

In a second embodiment of the tenth aspect which is also an embodiment of the first embodiment of the tenth aspect, the C5a is selected from the group comprising human C5a, monkey C5a, horse C5a, rabbit C5a, bovine C5a, canine C5a and porcine C5a, more preferably C5a is human C5a.

In a third embodiment of the tenth aspect which is also an embodiment of the first embodiment of the tenth aspect, the C5 is selected from the group comprising human C5, monkey C5, horse C5, rabbit C5, bovine C5, canine C5 and porcine C5, more preferably C5 is human C5.

The problem underlying the present invention is solved in an eleventh aspect which is also a first embodiment of the eleventh aspect, by a method for the screening of an antagonist or a agonist of the proteins of the complement system comprising the following steps:

providing a candidate antagonist and/or a candidate agonist of the proteins of the complement system, providing a nucleic acid according to any embodiment of the first and second aspect, providing a test system which provides a signal in the presence of a antagonist and/or a agonist of the proteins of the complement system, and determining whether the candidate antagonist is a antagonist of the proteins of the complement system and/or whether the candidate agonist is a agonist of the proteins of the complement system, whereby the proteins of the complement system are selected from the group comprising C5a and C5.

In a second embodiment of the eleventh aspect which is also an embodiment of the first embodiment of the eleventh aspect, the proteins of the complement system are selected from the group comprising human C5a and human C5.

In a third embodiment of the eleventh aspect which is also an embodiment of the first and the second embodiment of the eleventh aspect, one or the protein of the complement system is C5a, whereby C5a is preferably selected from the group comprising human C5a, monkey C5a, horse C5a, rabbit C5a, bovine C5a, canine C5a and porcine C5a, more preferably C5a is human C5a.

In a fourth embodiment of the eleventh aspect which is also an embodiment of the first and the second embodiment of the eleventh aspect, the one or the protein of the complement system is C5, whereby C5 is preferably selected from the group comprising human C5, monkey C5, horse C5, rabbit C5, bovine C5, canine C5 and porcine C5, more preferably C5 is human C5.

The problem underlying the present invention is solved in a twelfth aspect which is also a first embodiment of the twelfth aspect, by a method for the screening of a agonist and/or a antagonist of the proteins of the complement system comprising the following steps:

providing a protein of the complement system immobilised to a phase, preferably a solid phase, providing a nucleic acid according to any embodiment of the first and second aspect, whereby such nucleic acid is preferably labelled, adding a candidate agonist and/or a chemokine antagonist of the proteins of the complement system, and determining whether the candidate agonist is a agonist and/or whether the candidate antagonist is a antagonist of the proteins of the complement system, whereby the proteins of the complement system are selected from the group comprising C5a and C5.

In a second embodiment of the twelfth aspect which is also an embodiment of the first embodiment of the twelfth aspect, the determination is carried out such that it is assessed whether the nucleic acid is replaced by the candidate agonist or by a candidate antagonist of the proteins of the complement system.

In a third embodiment of the twelfth aspect which is also an embodiment of the first and the second embodiment of the twelfth aspect, the proteins of the complement system are selected from the group comprising human C5a and C5.

In a fourth embodiment of the twelfth aspect which is also an embodiment of the first and the second embodiment of the twelfth aspect, one or the protein of the complement system is C5a, whereby C5a is preferably selected from the group comprising human C5a, monkey C5a, horse C5a, rabbit C5a, bovine C5a, canine C5a and porcine C5a, more preferably C5a is human C5a.

In a fifth embodiment of the twelfth aspect which is also an embodiment of the first and the second embodiment of the twelfth aspect, one or the protein of the complement system is C5, whereby C5 is preferably selected from the group comprising human C5, monkey C5, horse C5, rabbit C5, bovine C5, canine C5 and porcine C5, more preferably C5 is human C5.

The problem underlying the present invention is solved in a $13^{th}$ aspect which is also a first embodiment of the $13^{th}$ aspect, by a kit for the detection of C5 and/or C5a comprising a nucleic acid according to any embodiment of the first and the second aspect.

In a second embodiment of the $13^{th}$ aspect which is also an embodiment of the first embodiment of the 13th aspect, the C5 and/or C5a is human C5 and/or human C5a.

The problem underlying the present invention is solved in a $14^{th}$ aspect which is also a first embodiment of the $14^{th}$ aspect, by an antagonist of the proteins of the complement system obtainable by the method according to any embodiment of the twelfth aspect, whereby the proteins of the complement system are selected from the group comprising C5a and C5.

In a second embodiment of the $14^{th}$ aspect which is also an embodiment of the first embodiment of the $14^{th}$ aspect, one or the proteins of the complement system selected from the group comprising human C5a and human C5.

In a third embodiment of the $14^{th}$ aspect which is also an embodiment of the first and second embodiment of the $14^{th}$ aspect, one or the protein of the complement system is C5a, whereby C5a is preferably selected from the group comprising human C5a, monkey C5a, horse C5a, rabbit C5a, bovine C5a, canine C5a and porcine C5a, more preferably C5a is human C5a.

In a fourth embodiment of the $14^{th}$ aspect which is also an embodiment of the first and second embodiment of the $14^{th}$ aspect, one or the protein of the complement system is C5, whereby C5 is preferably selected from the group comprising human C5, monkey C5, horse C5, rabbit C5, bovine C5, canine C5 and porcine C5, more preferably C5 is human C5.

The problem underlying the present invention is solved in a $15^{th}$ aspect which is also a first embodiment of the $15^{th}$ aspect, by an agonist of the proteins of the complement system obtainable by the method according to any embodiment of the twelfth aspect, whereby the proteins of the complement system are selected from the group comprising C5a and C5.

In a second embodiment of the $15^{th}$ aspect which is also an embodiment of the first embodiment of the $15^{th}$ aspect, the proteins of the complement system are selected from the group comprising human C5a and human C5.

In a third embodiment of the $15^{th}$ aspect which is also an embodiment of the first and second embodiment of the $15^{th}$ aspect, one or the protein of the complement system is C5a, whereby C5a is preferably selected from the group comprising human C5a, monkey C5a, horse C5a, rabbit C5a, bovine C5a, canine C5a and porcine C5a, more preferably C5a is human C5a.

In a fourth embodiment of the $15^{th}$ aspect which is also an embodiment of the first and second embodiment of the $15^{th}$ aspect, one or the protein of the complement system is C5, whereby C5 is preferably selected from the group comprising human C5, monkey C5, horse C5, rabbit C5, bovine C5, canine C5 and porcine C5, more preferably C5 is human C5.

The problem underlying the present invention is solved in a $16^{th}$ aspect which is also a first embodiment of the $16^{th}$ aspect, by a method for the detection of the nucleic acid according to any of the embodiments of the first and second aspect in a sample, whereby the method comprises the steps of:

a) providing a sample containing the nucleic acid according to the present invention;

b) providing a capture probe, whereby the capture probe is at least partially complementary to a first part of the nucleic acid according to any embodiment of the first and second aspect, and a detection probe, whereby the detection probe is at least partially complementary to a second part of the nucleic acid according to any embodiment of the first and second aspect, or, alternatively, the capture probe is at least partially complementary to a second part of the nucleic acid according to any embodiment of the first and the second aspect and the detection probe is at least partially complementary to the first part of the nucleic acid according to any embodiment of the first and the second aspect;

c) allowing the capture probe and the detection probe to react either simultaneously or in any order sequentially with the nucleic acid according to any embodiment of the first and the second aspect or part thereof;

d) optionally detecting whether or not the capture probe is hybridized to the nucleic acid according to the nucleic acid according to any embodiment of the first and the second aspect provided in step a); and e) detecting the complex formed in step c) consisting of the nucleic acid according to any embodiment of the first and the second aspect, and the capture probe and the detection probe.

In a second embodiment of the $16^{th}$ aspect which is also an embodiment of the first embodiment of the $16^{th}$ aspect, the detection probe comprises a detection means, and/or whereby the capture probe can be immobilized to a support, preferably a solid support.

In a third embodiment of the $16^{th}$ aspect which is also an embodiment of the first and second embodiment of the $16^{th}$ aspect, any detection probe which is not part of the complex is removed from the reaction so that in step e) only a detection probe which is part of the complex, is detected.

In a fourth embodiment of the $16^{th}$ aspect which is also an embodiment of the first, second and third embodiment of the $16^{th}$ aspect, step e) comprises the step of comparing the signal generated by the detection means when the capture probe and the detection probe are hybridized in the presence of the nucleic acid according to any embodiment of the first and second aspect or part thereof, and in the absence of said nucleic acid or part thereof.

In a further aspect the present invention is related to a medicament comprising a nucleic acid according to the present invention. In a preferred embodiment, the medicament is for the treatment of a disease, whereby such disease is any disease disclosed herein, preferably any disease for the treatment and/or prevention of which the nucleic acids according to the present invention can be used.

It is also within the present invention that the storage solution according to the present invention is used for storing, keeping or transporting an explanted tissue, organ or organ system. Finally such solution may, in an embodiment, be administered to the recipient of such explanted tissue organ or organ system. Such administration may occur prior, concommittantly and/or after the implantation of such explanted tissue, organ or organ system.

The present invention is based on the surprising finding that it is possible to generate nucleic acids binding specifically and with high affinity to C5a. Such nucleic acids are preferably also referred to herein as the nucleic acid molecules according to the present invention, the nucleic acids according to the present invention, the inventive nucleic acids or the inventive nucleic acid molecules.

The features of the nucleic acid according to the present invention as described herein can be realised in any aspect of the present invention where the nucleic acid is used, either alone or in any combination.

Human C5a is a basic protein having the amino acid sequence according to SEQ. ID. Nos. 1.

The finding that short high affinity binding nucleic acids to human C5a could be identified, is insofar surprising as Eaton et al. (1997) observed that the generation of aptamers, i.e. D-nucleic acids binding to a target molecule, directed to a basic protein is in general very difficult because this kind of target produces a high but non-specific signal-to-noise ratio. This high signal-to-noise ratio results from the high non-specific affinity shown by nucleic acids for basic targets such as human C5a.

As outlined in more detail in the claims and example 1, the present inventors could more surprisingly identify a number of different human C5a binding nucleic acid molecules, whereby most of the nucleic acids could be characterised in terms of stretches of nucleotide which are also referred to herein as Boxes. The various human C5a binding nucleic acid molecules can be categorised based on said Boxes and some structural features and elements, respectively. The various categories thus defined are also referred to herein as types and more specifically as Type A, Type B, Type C and Type D.

It is within the present invention that the nucleic acids according to the present invention or stretches thereof or any part(s) thereof can, in principle, hybridise with each other. Upon such hybridisation a double-stranded structure is formed. It will be acknowledged by the ones skilled in the art that such hybridisation may or may not occur, particularly under in vitro and/or in vivo conditions. Also, in case of such hybridisation, it is not necessarily the case that the hybridisation occurs over the entire length of the two stretches where, at least based on the rules for base pairing, such hybridisation and thus formation of a double-stranded structure may, in principle, occur. As preferably used herein, a double-stranded structure is a part of a molecule or a structure formed by two or more separate strands or two spatially separaten stretches of a single strand, whereby at least one, preferably two or more base pairs exist which are base pairing preferably in accordance with the Watson-Crick base pairing rules. It will also be acknowledged by the one skilled in the art that other base pairing such as Hoogsten base pairing may exist in or form such double-stranded structure.

In a preferred embodiment the term arrangement as used herein, means the order or sequence of structural or functional feature or elements described herein in connection with the nucleic acids disclosed herein.

It will be acknowledged by the person skilled in the art that the nucleic acids according to the present invention are capable of binding to both C5a and C5. This binding characteristic arises from the fact that for the identification of the nucleic acids a moiety of C5a was used which is present in both C5a and C5. Accordingly, the nucleic acids according to the present invention are suitable for the detection of either C5a, C5 or both. Also, it will be acknowledged by the person skilled in the art that the nucleic acids according to the present invention are antagonists to both C5 and C5a. Because of this the nucleic acids according to the present invention are suitable for the treatment and prevention, respecticely, of any disease which is associated with or caused by either C5a or C5 or both. The scientific rational may be taken from the prior art which establishes that C5a and C5, respectively, are involved or associated with a variety of diseases and conditions, respectively, and which is incoroporated herein by reference.

It is within the present invention that the nucleic acid according to the present invention is a nucleic acid molecule. Insofar the terms nucleic acid and nucleic acid molecule are used herein in a synonymous manner if not indicated to the contrary. In one embodiment of the present application the nucleic acid and thus the nucleic acid molecule comprises a nucleic acid molecule which is characterized in that all of the consecutive nucleotides forming the nucleic acid molecule are linked with or connected to each other by one or more than one covalent bond. More specifically, each of such nucleotides is linked with or connected to two other nucleotides, preferably through phosphodiester bonds or other bonds, forming a stretch of consecutive nucleotides. In such arrangement, however, the two terminal nucleotides, i.e. preferably the nucleotide at the 5' end and at the 3' end, are each linked to a single nucleotide only under the proviso that such arrangement is a linear and not a circular arrangement and thus a linear rather than a circular molecule.

In another embodiment of the present application the nucleic acid and thus the nucleic acid molecule comprises at least two groups of consecutive nucleotides, whereby within each group of consecutive nucleotides each nucleotide is linked with or connected to two other nucleotides, preferably through phosphodiester bonds or other bonds, forming a stretch of consecutive nucleotides. In such arrangement, however, the two terminal nucleotides, i.e. preferably the nucleotide at the 5' end and at the 3' end, are each linked to a single nucleotide only. In such embodiment, the two groups of consecutive nucleotides, however, are not linked with or connected to each other through a covalent bond which links one nucleotide of one group and one nucleotide of another or the other group through a covalent bond, preferably a covalent bond formed between a sugar moiety of one of said two nucleotides and a phosphor moiety of the other of said two nucleotides or nucleosides. In an alternative embodiment, the two groups of consecutive nucleotides, however, are linked with or connected to each other through a covalent bond which links one nucleotide of one group and one nucleotide of another or the other group through a covalent bond, preferably a covalent bond formed between a sugar moiety of one of said two nucleotides and a phosphor moiety of the other of said two nucleotides or nucleosides. Preferably, the at least two groups of consecutive nucleotides are not linked through any covalent bond. In another preferred embodiment, the at least two groups are linked through a covalent bond which is different from a phosphodiester bond. In still another embodiment, the at least two groups are linked through a covalent bond which is a phosphodiester bond.

The nucleic acids according to the present invention shall also comprise nucleic acids which are essentially homologous to the particular sequences disclosed herein. The term substantially homologous shall be understood such that the homology is at least 75%, preferably 85%, more preferably 90% and most preferably more than 95%, 96%, 97%, 98% or 99%.

The actual percentage of homologous nucleotides present in the nucleic acid according to the present invention will depend on the total number of nucleotides present in the nucleic acid. The percent modification can be based upon the total number of nucleotides present in the nucleic acid.

The homology can be determined as known to the person skilled in the art. More specifically, a sequence comparison algorithm then calculates the percent sequence identity for the test sequence(s) relative to the reference sequence, based on the designated program parameters. The test sequence is preferably the sequence or nucleic acid molecule which is said to be or to be tested whether it is homologous, and if so, to what extent, to another nucleic acid molecule, whereby such another nucleic acid molecule is also referred to as the reference sequence. In an embodiment, the reference sequence is a nucleic acid molecule as described herein, more preferably a nucleic acid molecule having a sequence according to any of SEQ. ID. NOs. 3 to 40, SEQ. ID. NOs. 43 to 79, SEQ. ID. NOs. 168-171, SEQ. ID. NOs. 174 to 179, and SEQ ID NOS 192-207. Optimal alignment of sequences for comparison can be conducted, e.g., by the local homology algorithm of Smith & Waterman (Smith & Waterman, 1981) by the homology alignment algorithm of Needleman & Wunsch (Needleman & Wunsch, 1970) by the search for similarity method of Pearson & Lipman (Pearson & Lipman, 1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

One example of an algorithm that is suitable for determining percent sequence identity is the algorithm used in the basic local alignment search tool (hereinafter "BLAST"), see, e.g. Altschul et al (Altschul et al. 1990 and Altschul et al, 1997). Software for performing BLAST analyses is publicly available through the National Center for Biotechnology Information (hereinafter "NCBI"). The default parameters used in determining sequence identity using the software available from NCBI, e.g., BLASTN (for nucleotide sequences) and BLASTP (for amino acid sequences) are described in McGinnis et al (McGinnis et al, 2004).

The term inventive nucleic acid or nucleic acid according to the present invention shall also comprise those nucleic acids comprising the nucleic acids sequences disclosed herein or part thereof, preferably to the extent that the nucleic acids or said parts are involved in the binding to human C5a. Such nucleic acid is, in an embodiment, one of the nucleic acid molecules described herein, or a derivative and/or a metabolite thereof, whereby such derivative and/or metabolite are preferably a truncated nucleic acid compared to the nucleic acid molecules described herein. Truncation may be related to either or both of the ends of the nucleic acids as disclosed herein. Also, truncation may be related to the inner sequence of nucleotides of the nucleic acid, i.e. it may be related to the nucleotide(s) between the 5' and the 3' terminal nucleotide, respectively. Moreover, truncation shall comprise the deletion of as little as a single nucleotide from the sequence of the nucleic acids disclosed herein. Truncation may also be related to more than one stretch of the inventive nucleic acid(s), whereby the stretch can be as little as one nucleotide long. The binding of a nucleic acid according to the present invention can be determined by the ones skilled in the art using routine experiments or by using or adopting a method as described herein, preferably as described herein in the example part.

The nucleic acids according to the present invention may be either D-nucleic acids or L-nucleic acids. Preferably, the inventive nucleic acids are L-nucleic acids. In addition it is possible that one or several parts of the nucleic acid are present as D-nucleic acids or at least one or several parts of the nucleic acids are L-nucleic acids. The term "part" of the nucleic acids shall mean as little as one nucleotide. Such nucleic acids are generally referred to herein as D- and L-nucleic acids, respectively. Therefore, in a particularly preferred embodiment, the nucleic acids according to the present invention consist of L-nucleotides and comprise at least one D-nucleotide. Such D-nucleotide is preferably attached to a part different from the stretches defining the nucleic acids according to the present invention, preferably those parts thereof, where an interaction with other parts of the nucleic acid is involved. Preferably, such D-nucleotide is attached at a terminus of any of the stretches and of any nucleic acid according to the present invention, respectively. In a further preferred embodiment, such D-nucleotides may act as a spacer or a linker, preferably attaching modifications such as PEG and HES to the nucleic acids according to the present invention.

It is also within an embodiment of the present invention that each and any of the nucleic acid molecules described herein in their entirety in terms of their nucleic acid sequence(s) are limited to the particular nucleotide sequence(s). In other words, the terms "comprising" or "comprise(s)" shall be interpreted in such embodiment in the meaning of containing or consisting of.

It is also within the present invention that the nucleic acids according to the present invention are part of a longer nucleic acid whereby this longer nucleic acid comprises several parts whereby at least one such part is a nucleic acid according to the present invention, or a part thereof. The other part(s) of these longer nucleic acids can be either one or several D-nucleic acid(s) or one or several L-nucleic acid(s). Any combination may be used in connection with the present invention. These other part(s) of the longer nucleic acid either alone or taken together, either in their entirety or in a particular combination, can exhibit a function which is different from binding, preferably from binding to C5a. One possible function is to allow interaction with other molecules, whereby such other molecules preferably are different from C5a, such as, e.g., for immobilization, cross-linking, detection or amplification. In a further embodiment of the present invention the nucleic acids according to the invention comprise, as individual or combined moieties, several of the nucleic acids of the present invention. Such nucleic acid comprising several of the nucleic acids of the present invention is also encompassed by the term longer nucleic acid.

L-nucleic acids as used herein are nucleic acids consisting of L-nucleotides, preferably consisting completely of L-nucleotides.

D-nucleic acids as used herein are nucleic acids consisting of D-nucleotides, preferably consisting completely of D-nucleotides.

The terms nucleic acid and nucleic acid molecule are used herein in an interchangeable manner if not explicitly indicated to the contrary.

Also, if not indicated to the contrary, any nucleotide sequence is set forth herein in 5'→3' direction.

As preferably used herein any position of a nucleotide is determined or referred to relative to the 5' end of a sequence, a stretch or a substretch. Accordingly, a second nucleotide is the second nucleotide counted from the 5' end of the sequence, stretch and substretch, respectively. Also, in accordance therewith, a penultimate nucleotide is the seond nucleotide counted from the 3' end of a sequence, stretch and substretch, respectively.

Irrespective of whether the inventive nucleic acid consists of D-nucleotides, L-nucleotides or a combination of both with the combination being e.g. a random combination or a defined sequence of stretches consisting of at least one L-nucleotide and at least one D-nucleic acid, the nucleic acid may consist of desoxyribonucleotide(s), ribonucleotide(s) or combinations thereof.

Designing the inventive nucleic acids as L-nucleic acid is advantageous for several reasons. L-nucleic acids are enantiomers of naturally occurring nucleic acids. D-nucleic acids, however, are not very stable in aqueous solutions and particularly in biological systems or biological samples due to the widespread presence of nucleases. Naturally occurring nucleases, particularly nucleases from animal cells are not capable of degrading L-nucleic acids. Because of this the biological half-life of the L-nucleic acid is significantly increased in such a system, including the animal and human body. Due to the lacking degradability of L-nucleic acid no nuclease degradation products are generated and thus no side effects arising therefrom observed. This aspect delimits the L-nucleic acid of factually all other compounds which are used in the therapy of diseases and/or disorders involving the presence of C5a. L-nucleic acids which specifically bind to a target molecule through a mechanism different from Watson Crick base pairing, or aptamers which consists partially or completely of L-nucleotides, particularly with those parts of the aptamer being involved in the binding of the aptamer to the target molecule, are also called spiegelmers.

It is also within the present invention that the inventive nucleic acids, also referred to herein as nucleic acids according to the invention, regardless whether they are present as D-nucleic acids, L-nucleic acids or D, L-nucleic acids or whether they are DNA or RNA, may be present as single-stranded or double-stranded nucleic acids. Typically, the inventive nucleic acids are single-stranded nucleic acids which exhibit defined secondary structures due to the primary sequence and may thus also form tertiary structures. The inventive nucleic acids, however, may also be double-stranded in the meaning that two strands which are complementary or partially complementary to each other are hybridised to each other. This confers stability to the nucleic acid which, in particular, will be advantageous if the nucleic acid is present in the naturally occurring D-form rather than the L-form.

In one embodiment, one or more nucleotide(s) of the nucleic acid according to the present invention can be replaced by linker or spacer molecule. In a preferred embodiment such linker or spacer is a separating stretch as defined herein. Such linker or spacer molecule is preferably a hydrophilic spacer comprising at least one, preferably a multitude of ethylene glycol moieties. Various linkers and spacers, respectively, are known to the ones skilled in the art and can be selected using the following criteria as described, e.g., by Pils and Micura (Pils and Micura, 2000). The linkers should or do not interfere with the base pairs themselves. Linker types that contain aromatic carbocycles stack on the terminal base pair and therefore are not suitable (Lewis et al., 1999). However, eythylene gylcol based or ethylene glycol derived linkers meet these requirements as they have the advantage of good water solubility and high conformational flexibility (Thomson et al, 1993; Ma et al., 1993; Durand et al. 1990). Preferably, the spacer comprises or consists of one or several ethylene glycol moieties, whereby the oxygen is replaced or substituted by a $CH_2$, a phosphate or sulfur.

The inventive nucleic acids may be modified. Such modifications may be related to the single nucleotide of the nucleic acid and are well known in the art. Examples for such modification are described in, among others, Venkatesan (2003); Kusser (2000); Aurup (1994); Cummins (1995); Eaton (1995); Green (1995); Kawasaki (1993); Lesnik (1993); and Miller (1993). Such modification can be a H atom, a F atom or O—CH3 group or NH2-group at the 2' position of the individual nucleotide of which the nucleic acid consists. Also, the nucleic acid according to the present invention can comprises at least one LNA nucleotide. In an embodiment the nucleic acid according to the present invention consists of LNA nucleotides.

In an embodiment, the nucleic acids according to the present invention may be a multipartite nucleic acid. A multipartite nucleic acid as used herein, is a nucleic acid which consists of at least two nucleic acid strands. These at least two nucleic acid strands form a functional unit whereby the functional unit is a ligand to a target molecule. The at least two nucleic acid strands may be derived from any of the inventive nucleic acids by either cleaving the nucleic acid to generate two strands or by synthesising one nucleic acid corresponding to a first part of the inventive, i.e. overall nucleic acid and another nucleic acid corresponding to the second part of the overall nucleic acid. It is to be acknowledged that both the cleavage and the synthesis may be applied to generate a multipartite nucleic acid where there are more than two strands as exemplified above. In other words, the at least two nucleic acid strands are typically different from two strands being complementary and hybridising to each other although a certain extent of complementarity between the various nucleic acid parts may exist.

Finally it is also within the present invention that a fully closed, i.e. circular structure for the nucleic acids according to the present invention is realized, i.e. that the nucleic acids according to the present invention are closed, preferably through a covalent linkage, whereby more preferably such covalent linkage is made between the 5' end and the 3' end of the nucleic acid sequences as disclosed herein.

The present inventors have discovered that the nucleic acids according to the present invention exhibit a very favourable $K_D$ value range.

A possibility to determine the binding constants of the nucleic acid molecules according to the present invention is the use of the "pull-down assay" as described in the examples. An appropriate measure in order to express the intensity of the binding between the individual nucleic acid molecule and to the target which is in the present case C5a, is the so-called $K_D$ value which as such as well the method for its determination are known to the one skilled in the art.

The nucleic acids according to the present invention are characterized by a certain $K_D$ value. Preferably, the $K_D$ value shown by the nucleic acids according to the present invention is below 1 μM. A $K_D$ value of about 1 μM is said to be characteristic for a non-specific binding of a nucleic acid to a target. As will be acknowledged by the ones in the art, the $K_D$ value of a group of compounds such as the nucleic acids according to the present invention are within a certain range. The above-mentioned $K_D$ of about 1 μM is a preferred upper limit for the $K_D$ value. The preferred lower limit for the $K_D$ of target binding nucleic acids can be about 10 picomolar or higher. It is within the present invention that the $K_D$ values of individual nucleic acids binding to C5a is preferably within this range. Preferred ranges can be defined by choosing any first number within this range and any second number within this range. Preferred upper values are 250 nM and 100 nM, preferred lower values are 50 nM, 10 nM, 1 nM, 100 pM and 10 pM.

The nucleic acid molecules according to the present invention may have any length provided that they are still able to bind to the target molecule. It will be acknowledged in the art that there are preferred lengths of the nucleic acids according to the present inventions. Typically, the length is between 15 and 120 nucleotides. It will be acknowledged by the ones skilled in the art that any integer between 15 and 120 is a possible length for the nucleic acids according to the present invention. More preferred ranges for the length of the nucleic acids according to the present invention are lengths of about 20 to 100 nucleotides, about 20 to 80 nucleotides, about 20 to 60 nucleotides, about 20 to 50 nucleotides and about 30 to 50 nucleotides.

It is within the present invention that the nucleic acids disclosed herein comprise a moiety which preferably is a high molecular weight moiety and/or which preferably allows to modify the characteristics of the nucleic acid in terms of, among others, residence time in the animal body, preferably the human body. A particularly preferred embodiment of such modification is PEGylation and HESylation of the nucleic acids according to the present invention. As used herein PEG stands for poly(ethylene glycole) and HES for hydroxyethly starch. PEGylation as preferably used herein is the modification of a nucleic acid according to the present invention whereby such modification consists of a PEG moiety which is attached to a nucleic acid according to the present invention. HESylation as preferably used herein is the modification of a nucleic acid according to the present invention whereby such modification consists of a HES moiety which is attached to a nucleic acid according to the present invention. These modifications as well as the process of modifying a nucleic acid using such modifications, is described in European patent application EP 1 306 382, the disclosure of which is herewith incorporated in its entirety by reference.

Preferably, the molecular weight of a modification consisting of or comprising a high molecular weight moiety is about from 2,000 to 250,000 Da, preferably 20,000 to 200,000 Da. In the case of PEG being such high molecular weight moiety the molecular weight is preferably 20,000 to 120,000 Da, more preferably 40,000 to 80,000 Da. In the case of HES being such high molecular weight moiety the molecular weight is preferably 20,000 to 200,000 Da, more preferably 40,000 to 150,000 Da. The process of HES modification is, e.g., described in German patent application DE 1 2004 006 249.8 the disclosure of which is herewith incorporated in its entirety by reference.

It is within the present invention that either of PEG and HES may be used as either a linear or branched from as further described in the patent applications WO2005074993 and PCT/EP02/11950. Such modification can, in principle, be made to the nucleic acid molecules of the present invention at any position thereof. Preferably such modification is made either to the 5'-terminal nucleotide, the 3'-terminal nucleotide and/or any nucleotide between the 5' nucleotide and the 3' nucleotide of the nucleic acid molecule.

The modification and preferably the PEG and/or HES moiety can be attached to the nucleic acid molecule of the present invention either directly or through a linker. It is also within the present invention that the nucleic acid molecule according to the present invention comprises one or more modifications, preferably one or more PEG and/or HES moiety. In an embodiment the individual linker molecule attaches more than one PEG moiety or HES moiety to a nucleic acid molecule according to the present invention. The linker used in connection with the present invention can itself be either linear or branched. This kind of linkers are known to the ones skilled in the art and are further described in the patent applications WO2005074993 and PCT/EP02/11950.

In a preferred embodiment the linker is a biodegradable linker. The biodegradable linker allows to modify the characteristics of the nucleic acid according to the present invention in terms of, among other, residence time in the animal body, preferably in the human body, due to release of the modification from the nucleic acid according to the present invention. Usage of a biodegradable linker may allow a better control of the residence time of the nucleic acid according to the present invention. A preferably embodiment of such biodegradable linker are biodegradable linker as described in but not limited to the international patent applications WO2006/052790, WO2008/034122, WO2004/092191 and WO2005/099768, whereby in the international patent applications WO2004/092191 and WO2005/099768, the linker is part of a polymeric oligonucleotide prodrug that consists of one or two modifications as described herein, a nucleic acid molecule and the biodegradable linker in between.

It is within the present invention that the modification is a biodegradable modification, whereby the biodegradable modification can be attached to the nucleic acid molecule of the present invention either directly or through a linker. The biodegradable modification allows to modify the characteristics of the nucleic acid according to the present invention in terms of, among other, residence time in the animal body, preferably in the human body, due to release of the modification from the nucleic acid according to the present invention. Usage of biodegradable modification may allow a better control of the residence time of the nucleic acid according to the present invention. A preferably embodiment of such biodegradable modification is biodegradable as described in but not restricted to the international patent applications WO2002/065963, WO2003/070823, WO2004/113394 and WO2000/41647, in WO2000/41647 preferably page 18, line 4 to 24.

Without wishing to be bound by any theory, it seems that by modifying the nucleic acids according to the present invention with high molecular weight moiety such as a polymer and more particularly the polymers disclosed herein, which are preferably physiologically acceptable, the excretion kinetic is changed. More particularly, it seems that due to the increased molecular weight of such modified inventive nucleic acids and due to the nucleic acids not being subject to metabolism particularly when in the L form, excretion from an animal body, preferably from a mammalian body and more preferably from a human body is decreased. As excretion typically occurs via the kidneys, the present inventors assume that the glomerular filtration rate of the thus modified nucleic acid is significantly reduced compared to the nucleic acids not having this kind of high molecular weight modification which results in an increase in the residence time in the body. In connection therewith it is particularly noteworthy that, despite such high molecular weight modification the specificity of the nucleic acid according to the present invention is not affected in a detrimental manner. Insofar, the nucleic acids according to the present invention have surprising characteristics—which normally cannot be expected from pharmaceutically active compounds—such that a pharmaceutical formulation providing for a sustained release is not necessarily required to provide for a sustained release. Rather the nucleic acids according to the present invention in their modified form comprising a high molecular weight moiety, can as such already be used as a sustained release-formulation. Insofar, the modification(s) of the nucleic acid molecules as disclosed herein and the thus modified nucleic acid molecules and any composition comprising the same may provide for a distinct, preferably controlled pharmacokinetics and biodistribution thereof. This also includes residence time in circulation and distribution to tissues. Such modifications are further described in the patent application PCT/EP02/11950.

However, it is also within the present invention that the nucleic acids disclosed herein do not comprise any modification and particularly no high molecular weight modification such as PEGylation or HESylation. Such embodiment is particularly preferred when the nucleic acid shows preferential distribution to any target organ or tissue in the body or when a fast clearance of the nucleic acids from the body after administration is desired. Nucleic acids as disclosed herein with a preferential distribution profile to any target organ or tissue in the body would allow establishment of effective local concentrations in the target tissue while keeping systemic concentration of the nucleic acids low. This would allow the use of low doses which is not only beneficial from an economic point of view, but also reduces unnecessary exposure of other tissues to the nucleic acid agent, thus reducing the potential risk of side effects. Fast clearance of the nucleic acids as disclosed herein from the body after administration might be desired in case of in vivo imaging or specific therapeutic dosing requirements using the nucleic acids or medicaments comprising the same, each according to the present invention.

The inventive nucleic acids, which are also referred to herein as the nucleic acids according to the present invention, and/or the antagonists according to the present invention may be used for the generation or manufacture of a medicament. Such medicament or a pharmaceutical composition according to the present invention contains at least one of the inventive nucleic acids, optionally together with further pharmaceutically active compounds, whereby the inventive nucleic acid preferably acts as pharmaceutically active compound itself. Such medicaments comprise in preferred embodiments at least a pharmaceutically acceptable carrier. Such carrier may be, e.g., water, buffer, PBS, glucose solution, preferably a 5% glucose salt balanced solution, starch, sugar, gelatine or any other acceptable carrier substance. Such carriers are generally known to the one skilled in the art. It will be acknowledged by the person skilled in the art that any embodiments, use and aspects of or related to the medicament of the present invention is also applicable to the pharmaceutical composition of the present invention and vice versa.

The indication, diseases and disorders for the treatment and/or prevention of which the nucleic acids, the pharmaceutical compositions and medicaments in accordance with or prepared in accordance with the present invention result from the involvement, either direct or indirect, of C5a in the respective pathogenetic mechanism.

The local release of C5a at sites of inflammation results in powerful pro-inflammatory stimuli. Thus, neutralization of C5a might be beneficial in many acute or chronic conditions, such as immune complex associated diseases in general (Heller et al., 1999); neurodegeneration and inflammation, e.g. in Alzheimer's disease (Bonifati & Kishore, 2007), asthma (Kohl, 2001); secondary damages of trauma (Yao et al. 1998); septic shock (Huber-Lang et al., 2001); systemic inflammtory response syndrome (SIRS); multiorgan failure (MOF); acute respiratory distress syndrome (ARDS); inflammatory bowel syndrome (IBD) (Woodruff et al., 2003); immune-complex-mediated renal disease (Wang, 2006), e.g. as a complication of systemic erythematosus (Manderson et al, 2004); infections; severe burns (Piccolo et al., 1999); reperfusion injury of organs such as heart, spleen, bladder, pancreas, stomach, lung, liver, kidney, limbs, brain, sceletal muscle or intestine (Riley et al., 2000) that may lead amongst others to delayed graft function (Lewis et al, 2008); psoriasis (Bergh et al., 1993); myocarditis; multiple sclerosis (Muller-Ladner et al., 1996); paroxysmal nocturnal hemoglobinuria (PNH), hemolysis, thromboembolism (Hillmern et al. 2007) and rheumatoid arthritis (RA) (Woodruff et al., 2002). Complement C5a has also been found in elevated amounts in drusen in age-related macular degeneration and it has been shown to lead to increased VEGF-expression and to promote choroidal neovascularization that may lead to vision impairment and loss (Nozaki et al, 2006).

An expert review on possible and already pursued complement-targeted therapies recently appeared in Nature biotechnology (Ricklin & Lambris, 2007).

Of course, because the C5a binding nucleic acids according to the present invention interact with or bind to human C5a, a skilled person will generally understand that the C5a binding nucleic acids according to the present invention can easily be used for the treatment, prevention and/or diagnosis of any disease of humans and animals as described herein. In connection therewith, it is to be acknowledged that the nucleic acid molecules according to the present invention can be used for the treatment and prevention of any of the diseases, disorder or condition described herein, irrespective of the mode of action underlying such disease, disorder and condition.

In the following, and without wishing to be bound by any theory, the rational for the use of the nucleic acid molecules according to the present invention in connection with the various diseases, disorders and conditions is provided, thus rendering the claimed therapeutic, preventive and diagnostic applicability of the nucleic acid molecules according to the present invention plausible. In order to avoid any unnecessary repetition, it should be acknowledged that due to the involvement of the C5a-SDF-1 receptor axis as outlined in connection therewith said axis may be addressed by the nucleic acid molecules according to the present invention such that the claimed therapeutic, preventive and diagnostic effect is achieved. It should furthermore be acknowledged that the particularities of the diseases, disorders and conditions, of the patients and any detail of the treatment regimen described in connection therewith, may be subject to preferred embodiments of the instant application.

Accordingly, disease and/or disorders and/or diseased conditions for the treatment and/or prevention of which the medicament according to the present invention may be used include, but are not limited to are autoimmune diseases such as rheumatoid arthritis (abbr. RA), ankylosing spodylitis (abbr. AS), systemic lupus erythematosus (abbr. SLE), multiple sclerosis (abbr. MS), psoriasis, alopecia greata, warm and cold autoimmune hemolytic anemia (abbr. AIHA), pernicious anemia, acute inflammatory diseases, autoimmune adrenalitis, chronic inflammatory demyelinating polyneuropathy (abbr. CIDP), Churg-Strauss syndrome, Cogan syndrome, CREST syndrome, pemphigus vulgaris and pemphigus foliaceus, bullous pemphigoid, polymyalgia rheumatica, polymyositis, primary biliary cirrhosis, pancreatitis, peritonitis, psoriatic arthritis, rheumatic fever, sarcoidosis, Sjörgensen syndrome, scleroderma, celiac disease, stiff-man syndrome, Takayasu arteritis, transient gluten intolerance, autoimmune uveitis, vitiligo, polychondritis, dermatitis herpetiformis (abbr. DH) or Duhring's disease, fibromyalgia, Goodpasture syndrome, Guillain-Barré syndrome, Hashimoto thyroiditis, autoimmune hepatitis, inflammatory bowel disease (abbr. IBD), Crohn's disease, colitis ulcerosa, myasthenia gravis, immune complex disorders, glomerulonephritis, polyarteritis nodosa, anti-phospholipid syndrome, polyglandular autoimmune syndrome, idiopatic pulmonar fibrosis, idiopathic thrombocytopenic purpura (abbr. ITP), urticaria, autoimmune infertility, juvenile rheumatoid arthritis, sarcoidosis, autoimmune cardiomyopathy, Lambert-Eaton syndrome, lichen sclerosis, Lyme disease, Graves disease, Behçet's disease, Ménière's disease, reactive arthritis (Reiter's syndrome); infections with viruses such as HIV, HBV, HCV, CMV or intracellular parasites such as *Leishmania, Rickettsia, Chlamydia, Coxiella, Plasmodium, Brucella*, mycobacteria, *Listeria, Toxoplasma* and *Trypanosoma*; secondary damages of trauma; local inflammation, shock, anaphylactic shock, burn, septic shock, haemorrhagic shock, systemic inflammatory response syndrome (abbr. SIRS), multiple organ failure (abbr. MOF), asthma and allergy, vasculitides such as arteritis temporalis, vasculitis, vascular leakage, and atherosclerosis; acute injuries of the central nervous system, myocarditis, dermatomyositis, gingivitis, acute respiratory insufficiency, chronic obstructive pulmonary disease, stroke, myocardial infarction, reperfusion injury, neurocognitive dysfunction, burn, inflammatory diseases of the eye such as uveitis, age-related macular degeneration (abbr. AMD), diabetic retinopathy (abbr. DR), diabetic macular edema (abbr. DME), ocular pemphigoid, keratoconjunctivitis, Stevens-Johnson syndrome, and Graves ophthalmopathy; local manifestations of systemic diseases, inflammatory diseases of the vasculature, acute injuries of the central nervous system, type 1 and 2 diabetes, the manifestations of diabetes, SLE, and rheumatic disease in the eye, brain, vasculature, heart, lung, kidneys, liver, gastrointestinal tract, spleen, skin, bones, lymphatic system, blood or other organ systems, for the prevention and/or support and/or post-operative treatment of coronary artery bypass graft (abbr. CABG), off-pump coronary artery bypass graft (abbr. OPCABG), minimally invasive direct coronary artery bypass graft (abbr. MIDCAB), percutaneous transluminal coronary angioplasty (abbr. PTCA), thrombolysis, organ transplantation, and vessel clamping surgery; for the prevention of organ damage of a transplanted organ or of an organ to be transplanted or for use of treatment of transplant rejection for transplanted organs such as liver, kidney, intestine, lung, heart, skin, limb, cornea, Langerhans islet, bone marrow, blood vessels and pancreas; fetal rejection.

The various diseases and disorders for the treatment and/or prevention of which the nucleic acids can be used, may be grouped as follows:

Autoimmune/Inflammatory Diseases

A subgroup of autoimmune and/or inflammatory diseases are systemic autoimmune and/or inflammatory diseases. Such systemic diseases comprise

- allergy
- septic shock,
- secondary damages of trauma
- warm and cold autoimmune hemolytic anemia (abbr. AIHA),
- systemic inflammatory response syndrome (abbr. SIRS),
- hemorrhagic shock,
- diabetes type 1,
- diabetes type 2, the manifestations of diabetes,
- diffuse scleroderma,
- polychondritis,
- polyglandular autoimmune syndrome,
- rheumatoid arthritis,
- systemic lupus erythematosus (abbr. SLE) and manifestations thereof,
- reactive arthritis (also known as Reiter's syndrome).

A subgroup of autoimmune and/or inflammatory diseases are autoimmune and/or inflammatory diseases of the gastro-intestinal tract. Such diseases of the gastro-intestinal tract comprise

- Crohn's disease,
- colitis ulcerosa,
- celiac disease,
- transient gluten intolerance,
- inflammatory bowel disease (abbr. IBD)
- pancreatitis A subgroup of autoimmune and/or inflammatory diseases are autoimmune and/or inflammatory diseases of the skin Such diseases of the skin comprise

- psoriasis,
- urticaria,
- dermatomyositis,
- pemphigus vulgaris,
- pemphigus foliaceus,
- bullous pemphigoid,
- Morphea/linear scleroderma, vitiligo, dermatitis herpetiformis (abbr. DH) or Duhring's disease, lichen sclerosis.

A subgroup of autoimmune and/or inflammatory diseases are autoimmune and/or inflammatory diseases of the vasculature. Such diseases of the vasculature comprise vasculitides (preferably arteritis temporalis), vasculitis, vascular leakage, polymyalgia rheumatica atherosclerosis Churg-Strauss syndrome Takayasu arteritis Goodpasture syndrome (mostly affecting the kidneys (glomeruli and the lungs)

glomerulonephritis polyarteritis nodosa,

Behçet's disease

A subgroup of autoimmune and/or inflammatory diseases are autoimmune and/or inflammatory diseases of the nervous system. Such diseases of the nervous system comprise multiple sclerosis (abbr. MS), chronic inflammatory demyelinating polyneuropathy (abbr. CIDP), neurocognitive dysfunction, stiff-man syndrome, Guillain-Barré syndrome, myasthenia gravis, Lambert-Eaton syndrome.

A subgroup of autoimmune and/or inflammatory diseases are muscular skeletal autoimmune and/or inflammatory diseases. Such muscular skeletal diseases comprise rheumatoid arthritis, rheumatic disease in the eye, brain, lung, kidneys, heart, liver, gastrointestinal tract, spleen, skin, bones, lymphatic system, blood or other organs, ankylosing spodylitis (abbr. AS), sarcoidosis, polymyalgia rheumatica, polymyositis, psoriatic arthritis, rheumatic fever, polychondritis, fibromyalgia, juvenile rheumatoid arthritis, Lyme disease, reactive arthritis (also known as Reiter's syndrome).

A subgroup of autoimmune and/or inflammatory diseases are other autoimmune and/or inflammatory diseases. Such other diseases comprise Cogan syndrome (autoimmune eye-inflammation and hearing loss), autoimmune adrenalitis, immune complex disordes, Ménière's disease, local inflammations, alopecia greata, acute inflammatory diseases, primary biliary cirrhosis, Sjörgen's syndrome, scleroderma, diffuse scleroderma, CREST syndrome, Morphea/linear scleroderma, autoimmune uveitis, Hashimoto thyroiditis (autoimmune thyroid destruction), Graves disease, autoimmune hepatitis, glomerulonephritis, peritonitis, anti-phospholipid syndrome, idiopathic pulmonary fibrosis, renal fibrosis autoimmune infertility, fetal rejection.

A subgroup of autoimmune and/or inflammatory diseases are haematological disorders. Such haematological disorders comprise pernicious anemia (observed as a secondary damage of crohn's disease or the autoimmune destruction of intrinsic factor producing parietal cells of the stomach mucosa), warm and cold autoimmune hemolytic anemia (abbr. AIHA), anti-phospholipid syndrome, idiopathic thrombocytopenic purpura (abbr. ITP).

Diseases of the Eye

Such diseases of the eye comprise uveitis, age-related macular degeneration (abbr. AMD), diabetic retinopathy (abbr. DR), diabetic macular edema (abbr. DME), retinal vessel occlusion, glaucoma, ocular pemphigoid, keratoconjunctivitis, Stevens-Johnson syndrome, and Graves ophthalmopathy.

Reperfusion Injuries, Delayed Graft Function and Transplant Rejections

Such reperfusion injuries and transplant rejections comprise stroke, myocardial infarction, reperfusion injuries or organ damage to transplanted organs, such as liver, kidney, intestine, lung, heart, skin, limb, cornea, islets of Langerhans, bone marrow, blood vessels and pancreas kidney damage after organ or bone marrow transplantation.

Prevention of Transplant Rejection

Such prevention of transplant rejection comprises transplant rejection of transplanted organs, such as liver, kidney, intestine, lung, heart, skin, limb, cornea, islets of Langerhans, bone marrow, blood vessels and pancreas.

Cardiovascular Diseases

Such cardiovascular diseases comprise atherosclerosis, myocarditis, myocardial infarction, stroke, Inflammatory diseases of the vasculature, vasculitides, preferably arteritis temporalis, vasculitis, vascular leakage, the manifestations of diabetes, pre-eclempsia, autoimmune cardiomyopathy, for the prevention and/or support and/or post-operative treatment of coronary artery bypass graft (abbr. CABG).

Respiratory Diseases

Such respiratory diseases comprise asthma, acute respiratory insufficiency, adult respiratory distress syndrome.

chronic obstructive pulmonary disease

Inflammatory Diseases

Such inflammatory diseases comprise
- inflammatory disease of the eye,
- autoimmune uveitis,
- local manifestations of systemic diseases.

Acute Reactions

Such acute reactions comprise
- secondary damages of trauma,
- shock,
- burn,
- anaphylactic shock,
- hemorrhagic shock,
- multiple organ failure (abbr. MOF),
- acute injuries of the central nervous system,
- acute injuries of the central nervous system.

Infectious Diseases

Such infectious diseases comprise
- Bacterial infections, preferably
- meningitis,
- Lyme disease,
- reactive arthritis (also known as Reiter's syndrome),
- sepsis and its complications such as organ failure, cardiac dysfunction, systemic hypoperfusion, acidosis, adult respiratory distress syndrome,
- viral infections, preferably
- HIV,
- HBV,
- HCV,
- CMV,
- viral meningitis or
- intracellular parasites, preferably
- *Leishmania,*
- *Rickettsia,*
- *Chlamydia,*
- *Coxiella,*
- *Plasmodium,*
- *Brucella,*
- mycobacteria,
- *Listeria,*
- *Toxoplasma* and
- *Trypanosoma.*

The nucleic acids according to the present invention may also be used in an intra-operative manner to avoid deleterious effects of the patient's immune system, more preferably
- for the prevention and/or support and/or post-operative treatment of coronary artery bypass graft (abbr. CABG),
- off-pump coronary artery bypass graft (abbr. OPCABG),
- minimally invasive direct coronary artery bypass graft (abbr. MIDCAB),
- percutaneous transluminal coronary angioplasty (abbr. PTCA),
- thrombolysis,
- organ transplantation,
- brain and spinal cord surgery,
- reconstructive surgery
- and vessel clamping surgery;
- for the prevention of organ damage of a transplanted organ or of an organ to be transplanted or
- for use of treatment of transplant rejection and reperfusion injury for transplanted organs, such as liver, kidney, intestine, lung, heart, skin, limb, cornea, islets of Langerhans, bone marrow, blood vessels and pancreas.

It is within the present invention that the medicament and pharmaceutical composition, resepectively, containing a nucleic acid according to the present inventors may be used for the treatment in such way.

In a further embodiment, the medicament comprises a further pharmaceutically active agent. Such further pharmaceutically active compounds are, among others but not limited thereto, those known to suppress the immune system such as calcineurin inhibitors, cyclosporin A, methotrexate, azathioprin, tacrolimus, rapamycin, chlorambucil, leflunomide, mycophenolate mofetil, brequinar, mizoribin, thalidomide, or deoxyspergualin. The further pharmaceutically active compound can be, in a further embodiment, also one of those compounds which reduce histamine production such as meclozin, clemastin, dimetinden, bamipin, ketotifen, cetirizin, lovecetirizin, cesloratadin, azelastin, mizolastin, levocabastin, terfenadin, fexofenadin, or ebastin. Such compounds can also be, but are not limited to, steroids and are preferably selected from the group comprising corticosteroids like prednisone, methylprednisolone, hydrocortisone, dexamethasone, triamcinolone, betamethasone, effervescent, or budesonide. Further, such compound can be one or several antibiotics such as, but not restricted to, aminoglycosides, β-lactam antibiotics, gyrase inhibitors, glycopeptide antibiotics, lincosamide, macrolide antibiotics, nitroimidazole derivatives, polypeptide antibiotics, sulfonamides, trimethoprim and tetracycline. Additionally, more specific anti-inflammatory or anti-angiogenic biologics can be used in combination such as IL-10, erlizumab, tolermab, rituximab, gomiliximab, basiliximab, daclizumab, HuMax-TAC, visilizumab, HuMaxCD4, clenoliximab, MAX 16H5, TNX 100, toralizumab, alemtuzumab, CY 1788, galiximab, pexelizumab, eculizumab, PMX-53, ETI 104, FG 3019, bertilimumab, 249417 (anti-factor IX) abciximab, YM 337, omalizumab, talizumab, fontolizumab, J695 (anti-IL12), HuMaxIL-15, mepolizumab, elsilimomab, HuDREG, anakinra, Xoma-052, adalimumab, infliximab, certolizumab, afelimomab, CytoFab, AME 527, Vapaliximab, bevacizumab, ranibizumab, vitaxin, belimumab, MLN 1202, volociximab, F200 (anti-α5β1), efalizumab, m60.11 (anti.CD11 b), etanercept, onercept, natalizumab, or siplizumab, tocilizumab, ustekinumab, ABT-874. Finally, the further pharmaceutically active agent may be a modulator of the activity of any other chemokine which can be a chemokine agonist or antagonist or a chemokine receptor agonist or antagonist. Alternatively, or additionally, such further pharmaceutically active agent is a further nucleic acid according to the present invention. Alternatively, the medicament comprises at least one more nucleic acid which binds to a target molecule different from C5a or exhibits a function which is different from the one of the nucleic acids according to the present invention.

In general the C5a antagonist can be combined with inhibitors of other proinflammatory molecules or their receptors. Examples for proinflammatory molecules whose action can be attenuated in combination with the C5a antagonist are IL-1, IL-2, IL-5, IL-6, IL-8, IL-10, IL-12, IL-13, IL-15, IL-16, IL-17, IL-18, IL-23, TNF, α4β7, α5β1, BlyS, cadherin, CCR2, CD11a, CD11b, CD125, CD130, CD16, CD18, CD2, CD20, CD22, CD23, CD25, CD28, CD3, CD30, CD4, CD40, CD40L, CD44, CD45R, CD54, CD62E, CD62L, CD68, CD8, CD80, CD86, CD95, CEP, gastrin-R, C1, C1-esterase, C5, factor D, MBL, complement receptor 1, CRTH2-receptor, CTGF, E- and P-selectin, eotaxin, factor IX, FGF-20, Fgl-2, GM-CSF, GP IIb/IIIa receptor, HMG1, ICAM-1, IgE, thymocytes, IFNγ, IFNr, IP-10, MCP-1, M-CSF receptor, MIF, MMP9, PDGF-D, SDF-1, TGFβ1, tissue factor, tyrosine kinase receptor, VAP-1, VCAM-1, VEGF, VLA1, and von Willebrandt factor.

It is within the present invention that the medicament is alternatively or additionally used, in principle, for the prevention of any of the diseases disclosed in connection with the use of the medicament for the treatment of said diseases. Respective markers therefore, i.e. for the respective diseases are known to the ones skilled in the art. Preferably, the respective marker is C5a.

In one embodiment of the medicament of the present invention, such medicament is for use in combination with other treatments for any of the diseases disclosed herein, particularly those for which the medicament of the present invention is to be used.

"Combination therapy" (or "co-therapy") includes the administration of a medicament of the invention and at least a second agent as part of a specific treatment regimen intended to provide the beneficial effect from the co-action of these therapeutic agents, i.e. the medicament of the present invention and said second agent. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected).

"Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to a subject a single capsule having a fixed ratio of each therapeutic agent or in multiple, single capsules for each of the therapeutic agents.

Sequential or substantially simultaneous administration of each therapeutic agent can be effected by any appropriate route including, but not limited to, topical routes, oral routes, intravenous routes, intramuscular routes, and direct absorption through mucous membrane tissues. The therapeutic agents can be administered by the same route or by different routes. For example, a first therapeutic agent of the combination selected may be administered by injection while the other therapeutic agents of the combination may be administered topically.

Alternatively, for example, all therapeutic agents may be administered topically or all therapeutic agents may be administered by injection. The sequence in which the therapeutic agents are administered is not narrowly critical unless noted otherwise. "Combination therapy" also can embrace the administration of the therapeutic agents as described above in further combination with other biologically active ingredients. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

As outlined in general terms above, the medicament according to the present invention can be administered, in principle, in any form known to the ones skilled in the art. A preferred route of administration is systemic administration, more preferably by parenteral administration, preferably by injection. Alternatively, the medicament may be administered locally. Other routes of administration comprise intramuscular, intraperitoneal, and subcutaneous, per orum, intranasal, intratracheal or pulmonary with preference given to the route of administration that is the least invasive, while ensuring efficiancy.

Parenteral administration is generally used for subcutaneous, intramuscular or intravenous injections and infusions. Additionally, one approach for parenteral administration employs the implantation of a slow-release or sustained-released systems, which assures that a constant level of dosage is maintained, that are well known to the ordinary skill in the art.

Furthermore, preferred medicaments of the present invention can be administered in intranasal form via topical use of suitable intranasal vehicles, inhalants, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels, wherein the concentration of active ingredient would typically range from 0.01% to 15%, w/w or w/v.

The medicament of the present invention will generally comprise an effective amount of the active component(s) of the therapy, including, but not limited to, a nucleic acid molecule of the present invention, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the medicament of the present invention.

In a further aspect the present invention is related to a pharmaceutical composition. Such pharmaceutical composition comprises at least one of the nucleic acids according to the present invention and preferably a pharmaceutically acceptable vehicle. Such vehicle can be any vehicle or any binder used and/or known in the art. More particularly such binder or vehicle is any binder or vehicle as discussed in connection with the manufacture of the medicament disclosed herein. In a further embodiment, the pharmaceutical composition comprises a further pharmaceutically active agent.

The preparation of a medicament and a pharmaceutical composition will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including eye drops, creams, lotions, salves, inhalants and the like. The use of sterile formulations, such as saline-based washes, by surgeons, physicians or health care workers to treat a particular area in the operating field may also be particularly useful. Compositions may also be delivered via microdevice, microparticle or sponge.

Upon formulation, a medicament will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the individual or the subject to be treated. Specific amounts of active compound required for administration depend on the judgment of the practitioner and are peculiar to each individual.

A minimal volume of a medicament required to disperse the active compounds is typically utilized. Suitable regimes for administration are also variable, but would be typified by initially administering the compound and monitoring the results and then giving further controlled doses at further intervals.

For instance, for oral administration in the form of a tablet or capsule (e.g., a gelatin capsule), the active drug component, i.e. a nucleic acid molecule of the present invention and/or any further pharmaceutically active agent, also referred to herein as therapeutic agent(s) or active compound(s) can be combined with an oral, non-toxic, pharmaceutically acceptable inert carrier such as ethanol, glycerol, water and the like. Moreover, when desired or necessary, suitable binders, lubricants, disintegrating agents, and coloring agents can also be incorporated into the mixture. Suitable binders include starch, magnesium aluminum silicate, starch paste, gelatin, methylcellulose, sodium carboxymethylcellulose and/or polyvinylpyrrolidone, natural sugars such as glucose or beta-lactose, corn sweeteners, natural and synthetic gums such as acacia, tragacanth or sodium alginate, polyethylene glycol, waxes, and the like. Lubricants used in these dosage forms include sodium oleate, sodium stearate, magnesium stearate, sodium benzoate, sodium acetate, sodium chloride, silica, talcum, stearic acid, its magnesium or calcium salt and/or polyethyleneglycol, and the like. Disintegrators include, without limitation, starch, methyl cellulose, agar, bentonite, xanthan gum starches, agar, alginic acid or its sodium salt, or effervescent mixtures, and the like. Diluents, include, e.g., lactose, dextrose, sucrose, mannitol, sorbitol, cellulose and/or glycine.

The medicament of the invention can also be administered in such oral dosage forms as timed release and sustained release tablets or capsules, pills, powders, granules, elixirs, tinctures, suspensions, syrups and emulsions. Suppositories are advantageously prepared from fatty emulsions or suspensions.

The pharmaceutical composition or medicament may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating, or coating methods, and typically contain about 0.1% to 75%, preferably about 1% to 50%, of the active ingredient.

Liquid, particularly injectable compositions can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form the injectable solution or suspension. Additionally, solid forms suitable for dissolving in liquid prior to injection can be formulated.

For solid compositions, excipients include pharmaceutical grades of mannitol, lactose, starch, magnesium stearate, sodium saccharin, talcum, cellulose, glucose, sucrose, magnesium carbonate, and the like. The active compound defined above, may be also formulated as suppositories, using for example, polyalkylene glycols, for example, propylene glycol, as the carrier. In some embodiments, suppositories are advantageously prepared from fatty emulsions or suspensions.

The medicaments and nucleic acid molecules, respectively, of the present invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, what is well known to the ordinary skill in the art. For example, the nucleic acid molecules described herein can be provided as a complex with a lipophilic compound or non-immunogenic, high molecular weight compound constructed using methods known in the art. Additionally, liposomes may bear such nucleic acid molecules on their surface for targeting and carrying cytotoxic agents internally to mediate cell killing. An example of nucleic-acid associated complexes is provided in U.S. Pat. No. 6,011,020.

The medicaments and nucleic acid molecules, respectively, of the present invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxidepolylysine substituted with palmitoyl residues. Furthermore, the medicaments and nucleic acid molecules, respectively, of the present invention may be coupled to a class of biodegradable polymers useful in achieving controlled release of a drag, for example, polylactic acid, polyepsilon capro lactone, polyhydroxy butyric acid, polyorthoesters, polyacetals, polydihydropyrans, polycyanoacrylates and cross-linked or amphipathic block copolymers of hydrogels.

If desired, the pharmaceutical composition and medicament, respectively, to be administered may also contain minor amounts of non-toxic auxiliary substances such as wetting or emulsifying agents, pH buffering agents, and other substances such as for example, sodium acetate, and triethanolamine oleate.

The dosage regimen utilizing the nucleic acid molecules and medicaments, respectively, of the present invention is selected in accordance with a variety of factors including type, species, age, weight, sex and medical condition of the patient; the severity of the condition to be treated; the route of administration; the renal and hepatic function of the patient; and the particular aptamer or salt thereof employed. An ordinarily skilled physician or veterinarian can readily determine and prescribe the effective amount of the drug required to prevent, counter or arrest the progress of the condition.

Effective plasma levels of the nucleic acid according to the present invention preferably range from 500 fM to 500 μM in the treatment of any of the diseases disclosed herein.

The nucleic acid molecules and medicaments, respectively, of the present invention may preferably be administered in a single daily dose, every second or third day, weekly, every second week, in a single monthly dose or every third month.

It is within the present invention that the medicament as described herein constitutes the pharmaceutical composition disclosed herein.

In a further aspect the present invention is related to a method for the treatment of a subject who is need of such treatment, whereby the method comprises the administration of a pharmaceutically active amount of at least one of the nucleic acids according to the present invention. In an embodiment, the subject suffers from a disease or is at risk to develop such disease, whereby the disease is any of those disclosed herein, particularly any of those diseases disclosed in connection with the use of any of the nucleic acids according to the present invention for the manufacture of a medicament.

It is to be understood that the nucleic acid as well as the antagonists according to the present invention can be used not only as a medicament or for the manufacture of a medicament, but also for cosmetic purposes, particularly with regard to the involvement of C5a in inflamed regional skin lesions. Therefore, a further condition or disease for the treatment or prevention of which the nucleic acid, the medicament and/or the pharmaceutical composition according to the present invention can be used, is inflamed regional skin lesions.

As preferably used herein a diagnostic or diagostic agent or diagnostic means is suitable to detect, either directly or indirectly C5a, preferably C5a as described herein and more preferably C5a as described herein in connection with the various disorders and diseases described herein. The diagnostic is suitable for the detection and/or follow-up of any of the disorders and diseases, respectively, described herein. Such detection is possible through the binding of the nucleic acids according to the present invention to C5a. Such binding can be either directly or indirectly be detected. The respective methods and means are known to the ones skilled in the art. Among others, the nucleic acids according to the present invention may comprise a label which allows the detection of the nucleic acids according to the present invention, preferably the nucleic acid bound to C5a. Such a label is preferably selected from the group comprising radioactive, enzymatic and fluorescent labels. In principle, all known assays developed for antibodies can be adopted for the nucleic acids according to the present invention whereas the target-binding antibody is substituted to a target-binding nucleic acid. In antibody-assays using unlabeled target-binding antibodies the detection is preferably done by a secondary antibody which is modified with radioactive, enzymatic and fluorescent labels and bind to the target-binding antibody at its Fc-fragment. In the case of a nucleic acid, preferably a nucleic acid according to the present invention, the nucleic acid is modified with such a label, whereby preferably such a label is selected from the group comprising biotin, Cy-3 and Cy-5, and such label is detected by an antibody directed against such label, e.g. an anti-biotin antibody, an anti-Cy3 antibody or an anti-Cy5 antibody, or—in the case that the label is biotin—the label is detected by streptavidin or avidin which naturally bind to biotin. Such antibody, streptavidin or avidin in turn is preferably modified with a respective label, e.g. a radioactive, enzymatic or fluorescent label (like an secondary antibody).

In a further embodiment the nucleic acid molecules according to the invention are detected or analysed by a second detection means, wherein the said detection means is a molecular beacon. The methodology of molecular beacon is known to persons skilled in the art. In brief, nucleic acids probes which are also referred to as molecular beacons, are a reverse complement to the nucleic acids sample to be detected and hybridise because of this to a part of the nucleic acid sample to be detected. Upon binding to the nucleic acid sample the fluorophoric groups of the molecular beacon are separated which results in a change of the fluorescence signal, preferably a change in intensity. This change correlates with the amount of nucleic acids sample present.

It will be acknowledged that the detection of C5a using the nucleic acids according to the present invention will particularly allow the detection of C5a as defined herein.

In connection with the detection of C5a a preferred method comprises the following steps:

(a) providing a sample which is to be tested for the presence of C5a, (b) providing a nucleic acid according to the present invention, (c) reacting the sample with the nucleic acid, preferably in a reaction vessel whereby step (a) can be performed prior to step (b), or step (b) can be preformed prior to step (a).

In a preferred embodiment a further step d) is provided, which consists in the detection of the reaction of the sample with the nucleic acid. Preferably, the nucleic acid of step b) is immobilised to a surface. The surface may be the surface of a reaction vessel such as a reaction tube, a well of a plate, or the surface of a device contained in such reaction vessel such as, for example, a bead. The immobilisation of the nucleic acid to the surface can be made by any means known to the ones skilled in the art including, but not limited to, non-covalent or covalent linkages. Preferably, the linkage is established via a covalent chemical bond between the surface and the nucleic acid. However, it is also within the present invention that the nucleic acid is indirectly immobilised to a surface, whereby such indirect immobilisation involves the use of a further component or a pair of interaction partners. Such further component is preferably a compound which specifically interacts with the nucleic acid to be immobilised which is also referred to as interaction partner, and thus mediates the attachment of the nucleic acid to the surface. The interaction partner is preferably selected from the group comprising nucleic acids, polypeptides, proteins and antibodies. Preferably, the interaction partner is an antibody, more preferably a monoclonal antibody. Alternatively, the interaction partner is a nucleic acid, preferably a functional nucleic acid. More preferably such functional nucleic acid is selected from the group comprising aptamers, spiegelmers, and nucleic acids which are at least partially complementary to the nucleic acid. In a further alternative embodiment, the binding of the nucleic acid to the surface is mediated by a multi-partite interaction partner. Such multi-partite interaction partner is preferably a pair of interaction partners or an interaction partner consisting of a first member and a second member, whereby the first member is comprised by or attached to the nucleic acid and the second member is attached to or comprised by the surface. The multi-partite interaction partner is preferably selected from the group of pairs of interaction partners comprising biotin and avidin, biotin and streptavidin, and biotin and neutravidin. Preferably, the first member of the pair of interaction partners is biotin.

A preferred result of such method is the formation of an immobilised complex of C5a and the nucleic acid, whereby more preferably said complex is detected. It is within an embodiment that from the complex the C5a is detected.

A respective detection means which is in compliance with this requirement is, for example, any detection means which is specific for that/those part(s) of the C5a. A particularly preferred detection means is a detection means which is selected from the group comprising nucleic acids, polypeptides, proteins and antibodies, the generation of which is known to the ones skilled in the art.

The method for the detection of C5a also comprises that the sample is removed from the reaction vessel which has preferably been used to perform step c).

The method comprises in a further embodiment also the step of immobilising an interaction partner of C5a on a surface, preferably a surface as defined above, whereby the interaction partner is defined as herein and preferably as above in connection with the respective method and more preferably comprises nucleic acids, polypeptides, proteins and antibodies in their various embodiments. In this embodiment, a particularly preferred detection means is a nucleic acid according to the present invention, whereby such nucleic acid may preferably be labelled or non-labelled. In case such nucleic acid is labelled it can directly or indirectly be detected. Such detection may also involve the use of a second detection means which is, preferably, also selected from the group comprising nucleic acids, polypeptides, proteins and embodiments in the various embodiments described herein. Such detection means are preferably specific for the nucleic acid according to the present invention. In a more preferred embodiment, the second detection means is a molecular beacon. Either the nucleic acid or the second detection means or both may comprise in a preferred embodiment a detection label. The detection label is preferably selected from the group comprising biotin, a bromo-desoxyuridine label, a digoxigenin label, a fluorescence label, a UV-label, a radio-label, and a chelator molecule. Alternatively, the second detection means interacts with the detection label which is preferably contained by, comprised by or attached to the nucleic acid. Particularly preferred combinations are as follows:

- the detection label is biotin and the second detection means is an antibody directed against biotin, or wherein
- the detection label is biotin and the second detection means is an avidin or an avidin carrying molecule, or wherein
- the detection label is biotin and the second detection means is a streptavidin or a stretavidin carrying molecule, or wherein
- the detection label is biotin and the second detection means is a neutravidin or a neutravidin carrying molecule, or
- wherein the detection label is a bromo-desoxyuridine and the second detection means is an antibody directed against bromo-desoxyuridine, or wherein
- the detection label is a digoxigenin and the second detection means is an antibody directed against digoxigenin, or wherein
- the detection label is a chelator and the second detection means is a radio-nuclide, whereby it is preferred that said detection label is attached to the nucleic acid. It is to be acknowledged that this kind of combination is also applicable to the embodiment where the nucleic acid is attached to the surface. In such embodiment it is preferred that the detection label is attached to the interaction partner.

Finally, it is also within the present invention that the second detection means is detected using a third detection means, preferably the third detection means is an enzyme, more preferably showing an enzymatic reaction upon detection of the second detection means, or the third detection means is a means for detecting radiation, more preferably radiation emitted by a radio-nuclide. Preferably, the third detection means is specifically detecting and/or interacting with the second detection means.

Also in the embodiment with an interaction partner of C5a being immobilised on a surface and the nucleic acid according to the present invention is preferably added to the complex formed between the interaction partner and the C5a, the sample can be removed from the reaction, more preferably from the reaction vessel where step c) and/or d) are preformed.

In an embodiment the nucleic acid according to the present invention comprises a fluorescence moiety and whereby the fluorescence of the fluorescence moiety is different upon complex formation between the nucleic acid and C5a and free C5a.

In a further embodiment the nucleic acid is a derivative of the nucleic acid according to the present invention, whereby the derivative of the nucleic acid comprises at least one fluorescent derivative of adenosine replacing adenosine. In a preferred embodiment the fluorescent derivative of adenosine is ethenoadenosine.

In a further embodiment the complex consisting of the derivative of the nucleic acid according to the present invention and the C5a is detected using fluorescence.

In an embodiment of the method a signal is created in step (c) or step (d) and preferably the signal is correlated with the concentration of C5a in the sample.

In a preferred aspect, the assays may be performed in 96-well plates, where components are immobilized in the reaction vessels as described above and the wells acting as reaction vessels.

The inventive nucleic acid may further be used as starting material for drug design. Basically there are two possible approaches. One approach is the screening of compound libraries whereas such compound libraries are preferably low molecular weight compound libraries. In an embodiment, the screening is a high throughput screening. Preferably, high throughput screening is the fast, efficient, trial-and-error evaluation of compounds in a target based assay. In best case the analysis are carried by a colorimetric measurement. Libraries as used in connection therewith are known to the one skilled in the art.

Alternatively, the nucleic acid according to the present invention may be used for rational design of drugs. Preferably, rational drug design is the design of a pharmaceutical lead structure. Starting from the 3-dimensional structure of the target which is typically identified by methods such as X-ray crystallography or nuclear magnetic resonance spectroscopy, computer programs are used to search through databases containing structures of many different chemical compounds. The selection is done by a computer, the identified compounds can subsequently be tested in the laboratory.

The rational design of drugs may start from any of the nucleic acid according to the present invention and involves a structure, preferably a three dimensional structure, which is similar to the structure of the inventive nucleic acids or identical to the binding mediating parts of the structure of the inventive nucleic acids. In any case such structure still shows the same or a similar binding characteristic as the inventive nucleic acids. In either a further step or as an alternative step in the rational design of drugs the preferably three dimensional structure of those parts of the nucleic acids binding to the neurotransmitter are mimicked by chemical groups which are different from nucleotides and nucleic acids. By this mimicry a compound different from the nucleic acids can be designed. Such compound is preferably a small molecule or a peptide.

In case of screening of compound libraries, such as by using a competitive assay which are known to the one skilled in the arts, appropriate C5a analogues, C5a agonists or C5a antagonists may be found. Such competitive assays may be set up as follows. The inventive nucleic acid, preferably a spiegelmer which is a target binding L-nucleic acid, is coupled to a solid phase. In order to identify C5a analogues labelled C5a may be added to the assay. A potential analogue would compete with the C5a molecules binding to the spiegelmer which would go along with a decrease in the signal obtained by the respective label. Screening for agonists or antagonists may involve the use of a cell culture assay as known to the ones skilled in the art.

The kit according to the present invention may comprise at least one or several of the inventive nucleic acids. Additionally, the kit may comprise at least one or several positive or negative controls. A positive control may, for example, be C5a, particularly the one against which the inventive nucleic acid is selected or to which it binds, preferably, in liquid form. A negative control may, e.g., be a peptide which is defined in terms of biophysical properties similar to C5a, but which is not recognized by the inventive nucleic acids. Furthermore, said kit may comprise one or several buffers. The various ingredients may be contained in the kit in dried or lyophilised form or solved in a liquid. The kit may comprise one or several containers which in turn may contain one or several ingredients of the kit. In a further embodiment, the kit comprises an instruction or instruction leaflet which provides to the user information on how to use the kit and its various ingredients.

The pharmaceutical and bioanalytical determination of the nucleic acid according to the present invention is elementarily for the assessment of its pharmacokinetic and biodynamic profile in several humours, tissues and organs of the human and non-human body. For such purpose, any of the detection methods disclosed herein or known to a person skilled in the art may be used. In a further aspect of the present invention a sandwich hybridisation assay for the detection of the nucleic acid according to the present invention is provided. Within the detection assay a capture probe and a detection probe are used. The capture probe is complementary to the first part and the detection probe to the second part of the nucleic acid according to the present invention. Both, capture and detection probe, can be formed by DNA nucleotides, modified DNA nucleotides, modified RNA nucleotides, RNA nucleotides, LNA nucleotides and/or PNA nucleotides.

Hence, the capture probe comprise a sequence stretch complementary to the 5'-end of the nucleic acid according to the present invention and the detection probe comprise a sequence stretch complementary to the 3'-end of the nucleic acid according to the present invention. In this case the capture probe is immobilised to a surface or matrix via its 5'-end whereby the capture probe can be immobilised directly at its 5'-end or via a linker between of its 5'-end and the surface or matrix. However, in principle the linker can be linked to each nucleotide of the capture probe. The linker can be formed by hydrophilic linkers of skilled in the art or by D-DNA nucleotides, modified D-DNA nucleotides, D-RNA nucleotides, modified D-RNA nucleotides, D-LNA nucleotides, PNA nucleotides, L-RNA nucleotides, L-DNA nucleotides, modified L-RNA nucleotides, modified L-DNA nucleotides and/or L-LNA nucleotides.

Alternatively, the capture probe comprises a sequence stretch complementary to the 3'-end of the nucleic acid according to the present invention and the detection probe comprise a sequence stretch complementary to the 5'-end of the nucleic acid according to the present invention. In this case the capture probe is immobilised to a surface or matrix via its 3'-end whereby the capture probe can be immobilised directly at its 3'-end or via a linker between of its 3'-end and the surface or matrix. However, in principle, the linker can be linked to each nucleotide of the sequence stretch that is complementary to the nucleic acid according to the present invention. The linker can be formed by hydrophilic linkers of skilled in the art or by D-DNA nucleotides, modified D-DNA nucleotides, D-RNA nucleotides, modified D-RNA nucleotides, D-LNA nucleotides, PNA nucleotides, L-RNA nucleotides, L-DNA nucleotides, modified L-RNA nucleotides, modified L-DNA nucleotides and/or L-LNA nucleotides.

The number of nucleotides of the capture and detection probe that may hybridise to the nucleic acid according to the present invention is variable and can be dependant from the number of nucleotides of the capture and/or the detection probe and/or the nucleic acid according to the present invention itself. The total number of nucleotides of the capture and the detection probe that may hybridise to the nucleic acid according to the present invention should be maximal the number of nucleotides that are comprised by the nucleic acid according to the present invention. The minimal number of nucleotides (2 to 10 nucleotides) of the detection and capture probe should allow hybridisation to the 5'-end or 3'-end, respectively, of the nucleic acid according to the present invention. In order to realize high specificity and selectivity between the nucleic acid according to the present invention and other nucleic acids occurring in samples that are analyzed the total number of nucleotides of the capture and detection probe should be or maximal the number of nucleotides that are comprised by the nucleic acid according to the present invention.

Moreover the detection probe preferably carries a marker molecule or label that can be detected as previously described herein. The label or marker molecule can in principle be linked to each nucleotide of the detection probe. Preferably, the label or marker is located at the 5'-end or 3'-end of the detection probe, whereby between the nucleotides within the detection probe that are complementary to the nucleic acid according to the present invention, and the label a linker can be inserted. The linker can be formed by hydrophilic linkers of skilled in the art or by D-DNA nucleotides, modified D-DNA nucleotides, D-RNA nucleotides, modified D-RNA nucleotides, D-LNA nucleotides, PNA nucleotides, L-RNA nucleotides, L-DNA nucleotides, modified L-RNA nucleotides, modified L-DNA nucleotides and/or L-LNA nucleotides.

The detection of the nucleic acid according to the present invention can be carried out as follows: The nucleic acid according to the present invention hybridises with one of its ends to the capture probe and with the other end to the detection probe. Afterwards unbound detection probe is removed by, e.g., one or several washing steps. The amount of bound detection probe which preferably carries a label or marker molecule, can be measured subsequently as, for example, outlined in more detail in WO/2008/052774 which is incorporated herein by reference.

As preferably used herein, the term treatment comprises in a preferred embodiment additionally or alternatively prevention and/or follow-up.

As preferably used herein, the terms disease and disorder shall be used in an interchangeable manner, if not indicated to the contrary.

As used herein, the term comprise is preferably not intended to limit the subject matter followed or described by such term. However, in an alternative embodiment the term comprises shall be understood in the meaning of containing and thus as limiting the subject matter followed or described by such term.

The various SEQ.ID. Nos., the chemical nature of the nucleic acid molecules according to the present invention and the target molecules C5a as used herein, the actual sequence thereof and the internal reference number is summarized in the following table.

| SEQ ID NO: | RNA/ Peptide | Sequence | Internal Reference |
|---|---|---|---|
| 1 | L-protein | TLQKKIEEIAAKYKHSVVKKCCYDGACVNNDETCEQRAARISLGPRCIKAFTECCVVAS QLRANISHKDMQLGR | human C5a |
| 2 | D-protein | TLQKKIEEIAAKYKHSVVKKCCYDGAAVNNDETCEQRAARISLGPRCIKAFTECCVVAS QLRAKISHKDMQLGR<br>\|<br>Biotin | biotinylated human D-C5a |
| 3 | L-RNA | 5'-AGCGUGCUUGUCCGAUUGGCGGCACCCUUGCGGGACUGGGGAGUACGCU | 172-D7-000 |
| 4 | L-RNA | 5'-CGUGCUUGUCCGAUUGGCGGCACCCUUGCGGGACUGGGGAGUACG | 172-D7-001 |
| 5 | L-RNA | 5'-GUGCUUGUCCGAUUGGCGGCACCCUUGCGGGACUGGGGAGUAC | 172-D7-002 |
| 6 | L-RNA | 5'-AGCGUGCUCGUCCGAUUGGCGGCACCCUUGCGGGACUGGGGAGUACGCU | 172-D7-003 |
| 7 and 221, respec-tively | L-RNA | 5'-AGCGUGCUUGUCCGA-Spacer-GCGGCACCCUUGCGGGACUGGGGAGUACGCU | 172-D7-004 |
| 8 and 222, respec-tively | L-RNA | 5'-AGCGUGCUUGUCCGAUUGGCGGCACCCU-Spacer-CGGGACUGGGGAGUACGCU | 172-D7-005 |
| 9 and 223, respec-tively | L-RNA | 5'-CGUGCUUGUCCGAUUGGCGGCACCCU-Spacer-CGGGACUGGGGAGUACG | 172-D7-008 |
| 10 and 224, respec-tively | L-RNA | 5'-CGUGCUUGUCCGAUUGGCGGCACCC-Spacer-GGGACUGGGGAGUACG | 172-D7-009 |
| 11 | L-RNA | 5'-CGCGCUUGUCCGAUUGGCGGCACCCUUGCGGGACUGGGGAGUGCG | 172-D7-010 |
| 12 | L-RNA | 5'-CGCGCUUGUCCGAUUGGCGGCACCCUUGCGGGACUGGGGAGCGCG | 172-D7-011 |
| 13 | L-RNA | 5'-GCGCUUGUCCGAUUGGCGGCACCCUUGCGGGACUGGGGAGCGC | 172-D7-012 |
| 14 and 225 | L-RNA | 5'-GCGCUUGUCCGAUUGGCGGCACCCU-Spacer-CGGGACUGGGGAGCGC | 172-D7-013 |
| 15 and 226 | L-RNA | 5'-GCGCUUGUCCGAUUGGCGGCACCC-Spacer-GGGACUGGGGAGCGC | 172-D7-014 |
| 16 and 227-228 | L-RNA | 5'-GCGCUUGUCCG-Spacer-UGGCGGCACCC-Spacer-GGGACUGGGGAGCGC | 172-D7-015 |
| 17 and 229 | L-RNA | 5'-GCGCUUGUCCGAUU-Spacer-CGGCACCC-Spacer-GGGACUGGGGAGCGC | 172-D7-016 |
| 18 and 230 | L-RNA | 5'-GCGCUGUCCGAUUGGCGGCACCC-Spacer-GGGACUGGGGGCGC | 172-D7-017 |
| 19 and 231 | L-RNA | 5'-GCGCUUGUCCGAUUGGCGGCACC-Spacer-GGACUGGGGAGCGC | 172-D7-018 |
| 20 | L-RNA | 5'-GUCCGAUUGGCGGCACCCUUGCGGGACUGGG | Type A Formula-1 |
| 21 | L-RNA | 5'-GUGCUGAACACGCCGCGUAGGACUUCAAUGGAGUAGAAUGGGCAGCAC | 179-A3 |
| 22 | L-RNA | 5'-GUGCUGCAACACGCCGAAUAGGUCCCGCGCGGAAGAAUGGGGCAGCAC | 179-C1 |
| 23 | L-RNA | 5'-GUGCCGCCAGACGCCGAACAGGUCGCAUCGCGAAGAAUCGGGCAGCAC | 179-D3 |
| 24 | L-RNA | 5'-GUGCUGCCAGACGCCGAACAGGUCGCAUCGCGAAGAAUCGGGUAGCAC | 179-E1 |
| 25 | L-RNA | 5'-GUGCUGCAAGACGCCGAACAGGUCCAGGAAGGGAAGAAUCGGGCAGCAC | 179-A4 |
| 26 | L-RNA | 5'-GUGCUGUCAGACGCCGAACAGGUCGCAUUGCGAAGAAUCGGGCAGCAC | 182-E6 |
| 27 | L-RNA | 5'-GUGCUGCUAAGACGCCGGAUAGGUCCUUUUAGGAAGAAUCGGAGCAC | 179-G1 |
| 28 | L-RNA | 5'-GUGCUGCAAGACGCCGAAUAGGACCGAAGUGUAGAAUCGUGCAGCAC | 182-D5 |
| 29 | L-RNA | 5'-GUGCUGAGACGCCGAACAGGACCAGCGAAAAUGGUAGAAUCGCAGCAC | 179-F2 |
| 30 | L-RNA | 5'-ASACGCCGVRYAGGWC | Type B Formula-1 |
| 31 | L-RNA | 5'-ASACGCCGMRYAGGWC | Type B Formula-2 |
| 32 | L-RNA | 5'-GWAGAAUSG | Type B Formula-3 |
| 33 | L-RNA | 5'-GGCUGAACACGCCGCGUAGGACUUCAAUGGAGUAGAAUGGGCAGCC | 179-A3-003 |
| 34 | L-RNA | 5'-GCUGAACACGCCGCGUAGGACUUCAAUGGAGUAGAAUGGGCAGC | 179-A3-007 |

-continued

| SEQ ID NO: | RNA/ Peptide | Sequence | Internal Reference |
|---|---|---|---|
| 35 | L-RNA | 5'-CUGAACACGCCGCGUAGGACUUCAAUGGAGUAGAAUGGGCAG | 179-A3-008 |
| 36 | L-RNA | 5'-GGCUGAACACGCCGCGUAGGACCCAAUGGGUAGAAUGGGCAGCC | 179-A3-014 |
| 37 and 232 | L-RNA | 5'-GGCUGAACACGCCGCGUAGGACCC-Spacer-GGGUAGAAUGGGCAGCC | 179-A3-042 |
| 38 | L-RNA | 5'-GCUGAACACGCCGCGUAGGACCCAAUGGGUAGAAUGGGCAGC | 179-A3-015 |
| 39 | L-RNA | 5'-GCGGAACACGCCGCGUAGGACCCAAUGGGUAGAAUGGGCCGC | 179-A3-020 |
| 40 | L-RNA | 5'-GCUGCACACGCCGCGUAGGACCCAAUGGGUAGAAUGGGCAGC | 179-A3-021 |
| 41 | L-protein | MLKKKIEEEAAKYRNAWVKKCCYDGAHRNDDETCEERAARIAIGPECIKAFKSC CAIASQFRADEHHKNMQLGR | bovine C5a |
| 42 | L-protein | MLQKKIEEEAAKYKYAMLKKCCYDGAYRNDDETCEERAARIKIGPKCVKAFKD CCYIANQVRAEQSHKNIQLGR | porcine C5a |
| 43 | L-RNA | 5'-GGCUAACACGCCGCGUAGGACCCAAUGGGUAGAAUGGGAGCC | 179-A3-024 |
| 44 | L-RNA | 5'-GGCCAACACGCCGCGUAGGACCCAAUGGGUAGAAUGGGGGCC | 179-A3-026 |
| 45 | L-RNA | 5'-GCCCAACACGCCGCGUAGGACCCAAUGGGUAGAAUGGGGGGC | 179-A3-029 |
| 46 | L-RNA | 5'-CGCCAACACGCCGCGUAGGACCCAAUGGGUAGAAUGGGGGCG | 179-A3-030 |
| 47 | L-RNA | 5'-CCGGAACACGCCGCGUAGGACCCAAUGGGUAGAAUGGGCCGG | 179-A3-034 |
| 48 | L-RNA | 5'-CGGGAACACGCCGCGUAGGACCCAAUGGGUAGAAUGGGCCCG | 179-A3-037 |
| 49 | L-RNA | 5'-GCUGGGCGUGUUUACUUGCUUAAUAGGGGGCCCAGC | 185-H3-001 |
| 50 | L-RNA | 5'-GCUGGGCGUGUUUACUUGCUUAAUAGGGGUCCCAGC | 185-D3 |
| 51 | L-RNA | 5'-GCUGGGCGUGUUUACUUGCUUAAUAGGGGGCCUAGC | 185-B3 |
| 52 | L-RNA | 5'-GCUGGGCGUGUUUAUUUGCUUAAUAGGGGGUCCAGC | 185-B1 |
| 53 | L-RNA | 5'-GCUGGGCGUGUUUACUUGCUUAAUAGGGAGCCCAGC | 185-F4 |
| 54 | L-RNA | 5'-GCUGGGCGUGUUUACUCGCUUAAUAGGGGACCCAGC | 185-A3 |
| 55 | L-RNA | 5'-GCUGGGGAGUGUUUACUUGCUUAAUAGGGGUCCCCAGC | 185-B4 |
| 56 | L-RNA | 5'-GCUGGGGAGUGUUUACUUGCUUAAUAGGGGUCCUCAGC | 185-G4 |
| 57 | L-RNA | 5'-GCUGGGGAGUGUUUACUUGCUUAAUAGGGAUCCUUAGC | 185-H4 |
| 58 | L-RNA | 5'-GCUGAGGAGUGUUUACUUGCUUAAUAGGGGUCCCCAGC | 185-C3 |
| 59 | L-RNA | 5'-GUGUUUAYUYGCUUAAUAGGGR | Type C Formula-1 |
| 60 | L-RNA | 5'-GUGUUUACUUGCUUAAUAGGGG | Type C Formula-2 |
| 61 | L-RNA | 5'-CGUGGCGUGUUUACUUGCUUAAUAGGGGGCCACG | 185-H3-005 |
| 62 | L-RNA | 5'-CCGCGCGUGUUUACUUGCUUAAUAGGGGGCGCGG | 185-H3-006 |
| 63 | L-RNA | 5'-UGGGCGUGUUUACUUGCUUAAUAGGGGGCCCA | 185-H3-002 |
| 64 | L-RNA | 5'-CGGGCGUGUUUACUUGCUUAAUAGGGGGCCCG | 185-H3-007 |
| 65 | L-RNA | 5'-GGGGCGUGUUUACUUGCUUAAUAGGGGGCCCC | 185-H3-014 |
| 66 | L-RNA | 5'-GGGGAGUGUUUACUUGCUUAAUAGGGGUCCCC | 185-B4-002 |
| 67 | L-RNA | 5'-GGGCGUGUUUACUUGCUUAAUAGGGGGCCC | 185-H3-003 |
| 68 | L-RNA | 5'-GGGAGUGUUUACUUGCUUAAUAGGGGUCCC | 185-B4-003 |
| 69 | L-RNA | 5'-GUACUGCGUUCGGACGUGGCAUGUUCCUUGACAAACGGUUGGCAGUAC | 182-E5 |
| 70 | L-RNA | 5'-GUGCUGCGUUCGGACGUGGCAUGUUCCUUGACAAACGGUUGGCAGCAC | 182-C5 |
| 71 | L-RNA | 5'-GUGCUGGGUUCGGACGUGGCAUGUUCCUUGAUAAACGGUUGCCAGCAC | 182-A8 |
| 72 | L-RNA | 5'-GUUCGGACGUGGCAUGUUCCUUGAYAAACGGUUG | Type D Formula-1 |

-continued

| SEQ ID NO: | RNA/ Peptide | Sequence | Internal Reference |
|---|---|---|---|
| 73 | L-RNA | 5'-GUGUUGCGUAGAAUGGACAUAGAGGACACGCCGCGCAGGACGCAGCAC | 179-B3 |
| 74 | L-RNA | 5'-GUGCUGCGAAGAAUGGACAAAUCGUACACGCCGAGCAGGUCGCAGUAC | 179-A2 |
| 75 | L-RNA | 5'-GUGCUGGACAGGACCAAGGUAAGGGCGGACCGAAAAACCUAGCAGCAC | 182-A5 |
| 76 | L-RNA | 5'-AGCGUGAACACGCCGAAUAGGUCCUAUAGGUGGGAAGAAUGGGCACGCU | 172-C5-000 |
| 77 | L-RNA | 5'-CCUGUGCGAAGAAUGGGCCCUAGGGAACACGCCGAAAAGGUUGCACAGG | 173-A11-000 |
| 78 | L-RNA | 5'-CCUGUGCGAAGCGCUCGGCGCAUACCGAUCAGGUCCGGCAAGCACAGG | 173-B12-000 |
| 79 | L-RNA | 5'-CGUGCAACACGGCGAAUAGCGUCCUACAGUUAGGCAGAAUGGGGCACG | 171-B1-000 |
| 80 | D-RNA | 5'-AGCGUGCUUGUCCGAUUGGCGGCACCCUUGCGGGACUGGGGAGUACGCU | 172-D7-000 |
| 81 | D-RNA | 5'-CGUGCUUGUCCGAUUGGCGGCACCCUUGCGGGACUGGGGAGUACG | 172-D7-001 |
| 82 | D-RNA | 5'-GUGCUUGUCCGAUUGGCGGCACCCUUGCGGGACUGGGGAGUAC | 172-D7-002 |
| 83 | D-RNA | 5'-AGCGUGCUCGUCCGAUUGGCGGCACCCUUGCGGGACUGGGGAGUACGCU | 172-D7-003 |
| 84 and 233, respectively | D-RNA | 5'-AGCGUGCUUGUCCGA-Spacer-GCGGCACCCUUGCGGGACUGGGGAGUACGCU | 172-D7-004 |
| 85 and 234, respectively | D-RNA | 5'-AGCGUGCUUGUCCGAUUGGCGGCACCCU-Spacer-CGGGACUGGGGAGUACGCU | 172-D7-005 |
| 86 and 235, respectively | D-RNA | 5'-CGUGCUUGUCCGAUUGGCGGCACCCU-Spacer-CGGGACUGGGGAGUACG | 172-D7-008 |
| 87 and 236, respectively | D-RNA | 5'-CGUGCUUGUCCGAUUGGCGGCACCC-Spacer-GGGACUGGGGAGUACG | 172-D7-009 |
| 88 | D-RNA | 5'-CGCGCUUGUCCGAUUGGCGGCACCCUUGCGGGACUGGGGAGUGCG | 172-D7-010 |
| 89 | D-RNA | 5'-CGCGCUUGUCCGAUUGGCGGCACCCUUGCGGGACUGGGGAGCGCG | 172-D7-011 |
| 90 | D-RNA | 5'-GCGCUUGUCCGAUUGGCGGCACCCUUGCGGGACUGGGGAGCGC | 172-D7-012 |
| 91 and 237 | D-RNA | 5'-GCGCUUGUCCGAUUGGCGGCACCCU-Spacer-CGGGACUGGGGAGCGC | 172-D7-013 |
| 92 and 238 | D-RNA | 5'-GCGCUUGUCCGAUUGGCGGCACCC-Spacer-GGGACUGGGGAGCGC | 172-D7-014 |
| 93 and 239-240 | D-RNA | 5'-GCGCUUGUCCG-Spacer-UGGCGGCACCC-Spacer-GGGACUGGGGAGCGC | 172-D7-015 |
| 94 and 241 | D-RNA | 5'-GCGCUUGUCCGAUU-Spacer-CGGCACCC-Spacer-GGGACUGGGGAGCGC | 172-D7-016 |
| 95 and 242 | D-RNA | 5'-GCGCUGUCCGAUUGGCGGCACCC-Spacer-GGGACUGGGGGCGC | 172-D7-017 |
| 96 and 243 | D-RNA | 5'-GCGCUUGUCCGAUUGGCGGCACC-Spacer-GGACUGGGGAGCGC | 172-D7-018 |
| 97 | D-RNA | 5'-GUCCGAUUGGCGGCACCCUUGCGGGACUGGG | Type A Formula-1 |
| 98 | D-RNA | 5'-GUGCUGAACACGCCGCGUAGGACUUCAAUGGAGUAGAAUGGGCAGCAC | 179-A3 |
| 99 | D-RNA | 5'-GUGCUGCAACACGCCGAAUAGGUCCCGCGCGGAAGAAUGGGGCAGCAC | 179-C1 |
| 100 | D-RNA | 5'-GUGCCGCCAGACGCCGAACAGGUCGCAUCGCGAAGAAUCGGGCAGCAC | 179-D3 |
| 101 | D-RNA | 5'-GUGCUGCCAGACGCCGAACAGGUCGCAUCGCGAAGAAUCGGGUAGCAC | 179-E1 |
| 102 | D-RNA | 5'-GUGCUGCAAGACGCCGAACAGGUCCAGGAAGGGAAGAAUCGGGCAGCAC | 179-A4 |
| 103 | D-RNA | 5'-GUGCUGUCAGACGCCGAACAGGUCGCAUUGCGAAGAAUCGGGCAGCAC | 182-E6 |
| 104 | D-RNA | 5'-GUGCUGCUAAGACGCCGGAUAGGUCCUUUUAGGAAGAAUCGGAGCAC | 179-G1 |
| 105 | D-RNA | 5'-GUGCUGCAAGACGCCGAAUAGGACCGAAGUGUAGAAUCGUGCAGCAC | 182-D5 |
| 106 | D-RNA | 5'-GUGCUGAGACGCCGAACAGGACCAGCGAAAAUGGUAGAAUCGCAGCAC | 179-F2 |
| 107 | D-RNA | 5'-ASACGCCGVRYAGGWC | Type B Formula-1 |
| 108 | D-RNA | 5'-ASACGCCGMRYAGGWC | Type B Formula-2 |

-continued

| SEQ ID NO: | RNA/ Peptide | Sequence | Internal Reference |
|---|---|---|---|
| 109 | D-RNA | 5'-GWAGAAUSG | Type B Formula-3 |
| 110 | D-RNA | 5'-GGCUGAACACGCCGCGUAGGACUUCAAUGGAGUAGAAUGGGCAGCC | 179-A3-003 |
| 111 | D-RNA | 5'-GCUGAACACGCCGCGUAGGACUUCAAUGGAGUAGAAUGGGCAGC | 179-A3-007 |
| 112 | D-RNA | 5'-CUGAACACGCCGCGUAGGACUUCAAUGGAGUAGAAUGGGCAG | 179-A3-008 |
| 113 | D-RNA | 5'-G-GCUGAACACGCCGCGUAGGACCCAAUGGGUAGAAUGGGCAGC-C | 179-A3-014 |
| 114 and 244 | D-RNA | 5'-G-GCUGAACACGCCGCGUAGGAC-CCSpacer-GGGUAGAAUGGGCAGC-C | 179-A3-042 |
| 115 | D-RNA | 5'-GCUGAACACGCCGCGUAGGACCCAAUGGGUAGAAUGGGCAGC | 179-A3-015 |
| 116 | D-RNA | 5'-GCGGAACACGCCGCGUAGGACCCAAUGGGUAGAAUGGGCCGC | 179-A3-020 |
| 117 | D-RNA | 5'-GCUGCACACGCCGCGUAGGACCCAAUGGGUAGAAUGGGCAGC | 179-A3-021 |
| 118 | L-protein | LLHQKVEEQAAKYKHRVPKKCCYDGARENKYETCEQRVARVTIGPHCIRAFNEC CTIADKIRKESHHKGMLLGR | rat C5a |
| 119 | L-protein | LLRQKIEEQAAKYKHSVPKKCCYDGARVNFYETCEERVARVTIGPLCIRAFNECC TIANKIRKESPHKPVQLGR | mouse C5a |
| 120 | D-RNA | 5'-GGCUAACACGCCGCGUAGGACCCAAUGGGUAGAAUGGGAGCC | 179-A3-024 |
| 121 | D-RNA | 5'-GGCCAACACGCCGCGUAGGACCCAAUGGGUAGAAUGGGGGCC | 179-A3-026 |
| 122 | D-RNA | 5'-GCCCAACACGCCGCGUAGGACCCAAUGGGUAGAAUGGGGGGC | 179-A3-029 |
| 123 | D-RNA | 5'-CGCCAACACGCCGCGUAGGACCCAAUGGGUAGAAUGGGGGCG | 179-A3-030 |
| 124 | D-RNA | 5'-CCGGAACACGCCGCGUAGGACCCAAUGGGUAGAAUGGGCCGG | 179-A3-034 |
| 125 | D-RNA | 5'-CGGGAACACGCCGCGUAGGACCCAAUGGGUAGAAUGGGCCCG | 179-A3-037 |
| 126 | D-RNA | 5'-GCUGGGCGUGUUUACUUGCUUAAUAGGGGGCCCAGC | 185-H3-001 |
| 127 | D-RNA | 5'-GCUGGGCGUGUUUACUUGCUUAAUAGGGGUCCCAGC | 185-D3 |
| 128 | D-RNA | 5'-GCUGGGCGUGUUUACUUGCUUAAUAGGGGGCCUAGC | 185-B3 |
| 129 | D-RNA | 5'-GCUGGGCGUGUUUAUUUGCUUAAUAGGGGGUCCAGC | 185-B1 |
| 130 | D-RNA | 5'-GCUGGGCGUGUUUACUUGCUUAAUAGGGAGCCCAGC | 185-F4 |
| 131 | D-RNA | 5'-GCUGGGCGUGUUUACUCGCUUAAUAGGGGACCCAGC | 185-A3 |
| 132 | D-RNA | 5'-GCUGGGGAGUGUUUACUUGCUUAAUAGGGGUCCCCAGC | 185-B4 |
| 133 | D-RNA | 5'-GCUGGGGAGUGUUUACUUGCUUAAUAGGGGUCCUCAGC | 185-G4 |
| 134 | D-RNA | 5'-GCUGGGGAGUGUUUACUUGCUUAAUAGGGAUCCUUAGC | 185-H4 |
| 135 | D-RNA | 5'-GCUGAGGAGUGUUUACUUGCUUAAUAGGGGUCCCCAGC | 185-C3 |
| 136 | D-RNA | 5'-GUGUUUAYUYGCUUAAUAGGGR | Type C Formula-1 |
| 137 | D-RNA | 5'-GUGUUUACUUGCUUAAUAGGGG | Type C Formula-2 |
| 138 | D-RNA | 5'-CGUGGCGUGUUUACUUGCUUAAUAGGGGGCCACG | 185-H3-005 |
| 139 | D-RNA | 5'-CCGCGCGUGUUUACUUGCUUAAUAGGGGGCGCGG | 185-H3-006 |
| 140 | D-RNA | 5'-UGGGCGUGUUUACUUGCUUAAUAGGGGGCCCA | 185-H3-002 |
| 141 | D-RNA | 5'-CGGGCGUGUUUACUUGCUUAAUAGGGGGCCCG | 185-H3-007 |
| 142 | D-RNA | 5'-GGGGCGUGUUUACUUGCUUAAUAGGGGGCCCC | 185-H3-014 |
| 143 | D-RNA | 5'-GGGGAGUGUUUACUUGCUUAAUAGGGGUCCCC | 185-B4-002 |
| 144 | D-RNA | 5'-GGGCGUGUUUACUUGCUUAAUAGGGGGCCC | 185-H3-003 |
| 145 | D-RNA | 5'-GGGAGUGUUUACUUGCUUAAUAGGGGUCCC | 185-B4-003 |
| 146 | D-RNA | 5'-GUACUGCGUUCGGACGUGGCAUGUUCCUUGACAAACGGUUGGCAGUAC | 182-E5 |

-continued

| SEQ ID NO: | RNA/ Peptide | Sequence | Internal Reference |
|---|---|---|---|
| 147 | D-RNA | 5'-GUGCUGCGUUCGGACGUGGCAUGUUCCUUGACAAACGGUUGGCAGCAC | 182-C5 |
| 148 | D-RNA | 5'-GUGCUGGGUUCGGACGUGGCAUGUUCCUUGAUAAACGGUUGCCAGCAC | 182-A8 |
| 149 | D-RNA | 5'-GUUCGGACGUGGCAUGUUCCUUGAYAAACGGUUG | Type D Formula-1 |
| 150 | D-RNA | 5'-GUGUUGCGUAGAAUGGACAUAGAGGACACGCCGCGCAGGACGCAGCAC | 179-B3 |
| 151 | D-RNA | 5'-GUGCUGCGAAGAAUGGACAAAUCGUACACGCCGAGCAGGUCGCAGUAC | 179-A2 |
| 152 | D-RNA | 5'-GUGCUGGACAGGACCAAGGUAAGGGCGGACCGAAAAACCUAGCAGCAC | 182-A5 |
| 153 | D-RNA | 5'-AGCGUGAACACGCCGAAUAGGUCCUAUAGGUGGGAAGAAUGGGCACGCU | 172-C5-000 |
| 154 | D-RNA | 5'-CCUGUGCGAAGAAUGGGCCCUAGGGAACACGCCGAAAAGGUUGCACAGG | 173-A11-000 |
| 155 | D-RNA | 5'-CCUGUGCGAAGCGCUCGGCGCAUACCGAUCAGGUCCGGCAAGCACAGG | 173-B12-000 |
| 156 | D-RNA | 5'-CGUGCAACACGGCGAAUAGCGUCCUACAGUUAGGCAGAAUGGGGCACG | 171-B1-000 |
| 157 | L-RNA/ D-RNA (gg) | 5'-ggAGCGUGCUUGUCCGAUUGGCGGCACCCUUGCGGGACUGGGGAGUACGCU | 172-D7-000 |
| 158 and 245 | L-RNA/ D-RNA (gg) | 5'-ggGCGCUUGUCCGAUUGGCGGCACCCU-Spacer-CGGGACUGGGGAGCGC | 172-D7-013 |
| 159 | L-RNA/ D-RNA (gg) | 5'-ggGGCUGAACACGCCGCGUAGGACCCAAUGGGUAGAAUGGGCAGCC | 179-A3-014 |
| 160 | L-RNA/ D-RNA (gg) | 5'-ggGCUGAACACGCCGCGUAGGACCCAAUGGGUAGAAUGGGCAGC | 179-A3-015 |
| 161 | L-RNA/ D-RNA (gg) | 5'-ggGCUGGGCGUGUUUACUUGCUUAAUAGGGGGCCCAGC | 185-H3-001 |
| 162 | L-RNA/ D-RNA (gg) | 5'-ggUGGGCGUGUUUACUUGCUUAAUAGGGGGCCCA | 185-H3-002 |
| 163 | L-RNA/ D-RNA (gg) | 5'-ggGGGGCGUGUUUACUUGCUUAAUAGGGGGCCCC | 185-H3-014 |
| 164 | L-RNA/ D-RNA (gg) | 5'-ggGGGCGUGUUUACUUGCUUAAUAGGGGGCCC | 185-H3-003 |
| 165 | L-RNA/ D-RNA (gg) | 5'-ggGUACUGCGUUCGGACGUGGCAUGUUCCUUGACAAACGGUUGGCAGUAC | 182-E5 |
| 166 | L-RNA/ D-RNA (gg) | 5'-ggGUGCUGCGUUCGGACGUGGCAUGUUCCUUGACAAACGGUUGGCAGCAC | 182-C5 |
| 167 and 246 | L-RNA | 5'-PEG-GCGCUUGUCCGAUUGGCGGCACCCU-Spacer-CGGGACUGGGGAGCGC | 172-D7-013-5'-PEG |
| 168 | L-RNA | 5'-PEG-GGCUGAACACGCCGCGUAGGACCCAAUGGGUAGAAUGGGCAGCC | 179-A3-014-5'-PEG |
| 169 | L-RNA | 5'-PEG-GCUGGGCGUGUUUACUUGCUUAAUAGGGGGCCCAGC | 185-H3-001-5'-PEG |
| 170 | L-RNA | 5'-PEG-GGGGCGUGUUUACUUGCUUAAUAGGGGGCCCC | 185-H3-014-5'-PEG |
| 171 | L-protein | TLQKKIEEIAAKYKHSVVKKCCYDGACVNNDETCEQRAARISLGPRCIKAFTECC<br>VVASQLRANISHKDMQLGRLHMKTLLPVSKPEIRSYFPESWLWEVHLVPRRKQL<br>QFALPDSLTTWEIQGIGISNTGICVADTVKAKVFKDVFLEMNIPYSVVRGEQIQLK<br>GTVYNYRTSGMQFCVKMSAVEGICTSESPVIDHQGTKSSKCVRQKVEGSSSHLVT<br>FTVLPLEIGLHNINFSLETWFGKEILVKTLRVVPEGVKRESYSGVTLDPRGIYGTIS<br>RRKEFPYRIPLDLVPKTEIKRILSVKGLLVGEILSAVLSQEGINILTHLPKGSAEAEL<br>MSVVPVFYVFHYLETGNHWNIFHSDPLIEKQKLKKKLKEGMLSIMSYRNADYSY<br>SVWKGGSASTWLTAFALRVLGQVNKYVEQNQNSICNSLLWLVENYQLDNGSFK<br>ENSQYQPIKLQGTLPVEARENSLYLTAFTVIGIRKAFDICPLVKIDTALIKADNFLLE<br>NTLPAQSTFTLAISAYALSLGDKTHPQFRSIVSALKREALVKGNPPIYRFWKDNLQ<br>HKDSSVPNTGTARMVETTAYALLTSLNLKDINYVNPVIKWLSEEQRYGGGFYSTQ<br>DTINAIEGLTEYSLLVKQLRLSMDIDVSYKHKGALHNYKMTDKNFLGRPVEVLLN<br>DDLIVSTGFGSGLATVHVTTVVHKTSTSEEVCSFYLKIDTQDIEASHYRGYGNSDY<br>KRIVACASYKPSREESSSGSSHAVMDISLPTGISANEEDLKALVEGVDQLFTDYQI<br>KDGHVILQLNSIPSSDFLCVRFRIFELFEVGFLSPATFTVYEYHRPDKQCTMFYSTS<br>NIKIQKVCEGAACKCVEADCGQMQEELDLTISAETRKQTACKPEIAYAYKVSITSI<br>TVENVFVKYKATLLDIYKTGEAVAEKDSEITFIKKVTCTNAELVKGRQYLIMGKE<br>ALQIKYNFSFRYIYPLDSLTWIEYWPRDTTCSSCQAFLANLDEFAEDIFLNGC | Human C5, alpha chain |
| 172 | L-protein | QEQTYVISAPKIFRVGASENIVIQVYGYTEAFDATISIKSYPDKKFSYSSGH<br>VHLSSENKFQNSAILTIQPKQLPGGQNPVSYVYLEVVSKHFSKSKRMPITY<br>DNGFLFIHTDKPVYTPDQSVKVRVYSLNDDLKPAKRETVLTFIDPEGSEVD<br>MVEEIDHIGIISFPDFKIPSNPRYGMWTIKAKYKEDFSTTGTAYFEVKEYVL<br>PHFSVSIEPEYNFIGYKNFKNFEITIKARYFYNKVVTEADVYITFGIREDLK<br>DDQKEMMQTAMQNTMLINGIAQVTFDSETAVKELSYYSLEDLNNKYLYI<br>AVTVIESTGGFSEEAEIPGIKYVLSPYKLNLVATPLFLKPGIPYPIKVQVKDS<br>LDQLVGGVPVILNAQTIDVNQETSDLDPSKSVTRVDDGVASFVLNLPSGV<br>TVLEFNVKTDAPDLPEENQAREGYRAIAYSSLSQSYLYIDWTDNHKALLV | Human C5, beta chain |

-continued

| SEQ ID NO: | RNA/ Peptide | Sequence | Internal Reference |
|---|---|---|---|
| | | GEHLNIIVTPKSPYIDKITHYNYLILSKGKIIHFGTREKFSDASYQSINIPVTQ NMVPSSRLLVYYIVTGEQTAELVSDSVWLNIEEKCGNQLQVHLSPDADAY SPGQTVSLNMATGMDSWVALAAVDSAVYGVQRGAKKPLERVFQFLEKS DLGCGAGGGLNNANVFHLAGLTFLTNANADDSQENDEPCKEIL | |
| 173 and 190-191 | L-RNA | 5' $X_1X_2X_3GYGCX_4Y$ | Type A Formula-2-5' |
| 174 and 192-193 | L-RNA | 5' $GX_5GYRCX_6X_7X_8$ | Type A Formula-2-3' |
| 175 | L-RNA | 5' $X_3GYGCX_4U$ | Type A Formula-3-5' |
| 176 | L-RNA | 5' $GX_5GYGCX_6$ | Type A Formula-3-3' |
| 177 and 194-200 | L-RNA | 5' $X_1X_2SBBX_3X_4X_5$ | Type B Formula-4-5' |
| 178 and 201-207 | L-RNA | 5' $X_6X_7X_8VVSX_9X_{10}$ | Type B Formula-4-3' |
| 179 | L-RNA | 5' $X_1X_2GCYX_3X_4X_5$ | Type B Formula-5-5' |
| 180 | L-RNA | 5' $X_6X_7X_8AGCX_9X_{10}$ | Type B Formula-5-3' |
| 181 | L-RNA | 5' $X_1X_2GCCX_3X_4X_5$ | Type B Formula-6-5' |
| 182 and 214-215 | L-RNA | 5' $X_1X_2X_3KVGX_4M$ | Type C Formula-3-5' |
| 183 and 216-217 | L-RNA | 5' $DX_5YBHX_6X_7X_8$ | Type C Formula-3-3' |
| 184 | D-DNA | 5'-ATGCTACAAGAGAAGATAGAAG | C5a-Primer-I |
| 185 | D-DNA | 5'-CTAGCATGCTTACCTTCCCAATTGC | C5a-Primer-II |
| 186 | L-Protein | MLQEKIEEIAAKYKHLVVKKCCYDGVRINHDETCEQRAARISVGPRC VKAFTECCVVASQLRANNSHKDLQLGR | monkey C5a, His6-macC5a ('His6' disclosed as SEQ ID NO: 247) |
| 187 | L-RNA | 5'--PEG-CCCCGGGGGAUAAUUCGUUCAUUUGUGCGGGG | 185-H3-014-REVERSE-5'-PEG |
| 188 and 208 | L-RNA | 5' $X_1X_2SSBX_3X_4X_5$ | Type B Formula-7-5' |
| 189 and 209 | L-RNA | 5' $X_6X_7X_8VSSX_9X_{10}$ | Type B Formula-7-3' |

The present invention is further illustrated by the figures, examples and the sequence listing from which further features, embodiments and advantages may be taken, wherein FIG. 1 shows an alignment of sequences of RNA ligand 172-D7-000 (SEQ ID NO: 3) and the derivatives of RNA ligand 172-D7-000 (SEQ ID NOS 4-7, 221, 8, 222, 9, 223, 10, 224, and 11-12, respectively, in order of appearance) binding to human C5a indicating the sequence motif ("Type A") that is in a preferred embodiment in its entirety essential for binding to human C5a;

FIG. 2 shows further derivatives (SEQ ID NOS 13-14, 225, 15, 226, 16, 227-228, 17, 229, 18, 230, 19, and 231, respectively, in order of appearance) of RNA ligand 172-D7-000 (SEQ ID NO: 3) (human C5a RNA ligand of sequence motif "Type A" (SEQ ID NO: 20));

FIG. 3 shows an alignment of sequences of related RNA ligands (SEQ ID NOS 21-29, respectively, in order of appearance) binding to human C5a indicating the sequence motif ("Type B" (SEQ ID NOS 30-32, respectively in order of appearance)) that is in a preferred embodiment in its entirety essential for binding to human C5a;

FIG. 4 shows derivatives (SEQ ID NOS 33-37, 232, and 38-40, respectively, in order of appearance) of RNA ligands 179-A3 (SEQ ID NO: 21) (human C5a RNA ligand of sequence motif "Type B");

FIG. 5 shows more derivatives (SEQ ID NOS 43-48, respectively, in order of appearance) of RNA ligand 179-A3 (human C5a RNA ligand of sequence motif "Type B");

FIG. 6 shows an alignment of sequences of related RNA ligands (SEQ ID NOS 49-58, respectively, in order of appearance) binding to human C5a indicating the sequence motif ("Type C" (SEQ ID NOS 59-60, respectively, in order of appearance)) that is in a preferred embodiment in its entirety essential for binding to human C5a;

FIG. 7 shows derivatives (SEQ ID NOS 61-68, respectively, in order of appearance) of RNA ligands 185-H3-001 (SEQ ID NO: 49) and 185-B4 (human C5a RNA ligands of sequence motif "Type C");

FIG. 8 shows an alignment of sequences of related RNA ligands (SEQ ID NOS 69-71, respectively, in order of appearance) binding to human C5a indicating the sequence motif ("Type D" (SEQ ID NO: 72)) that is in a preferred embodiment in its entirety essential for binding to human C5a;

FIG. 9 shows a table of sequences of several different RNA ligands (SEQ ID NOS 73-79, respectively, in order of appearance) binding to human C5a which can not be related to the C5a binding sequence motifs "Type A", "Type B"; "Type C" or "Type D";

FIG. 10 shows the result of a binding analysis of the aptamers of C5a binding nucleic acids 172-D7-000 and 172-D7-013 to biotinylated human D-C5a at 37° C., represented as binding of the aptamers over concentration of biotinylated human D-C5a;

FIG. 12 shows the result of a binding analysis of the aptamer of C5a binding nucleic acid 179-A3 to biotinylated human D-C5a at 37° C., represented as binding of the aptamer over concentration of biotinylated human D-C5a;

FIG. 15 shows the result of a binding analysis of the aptamer of C5a binding nucleic acid 185-H3-001 to biotinylated human D-C5a at 37° C., represented as binding of the aptamer over concentration of biotinylated human D-C5a;

FIG. 16 shows the result of a binding analysis of the aptamer of C5a binding nucleic acid 185-H3-014 to biotinylated human D-C5a at 37° C., represented as binding of the aptamer over concentration of biotinylated human D-C5a;

Figure 17:
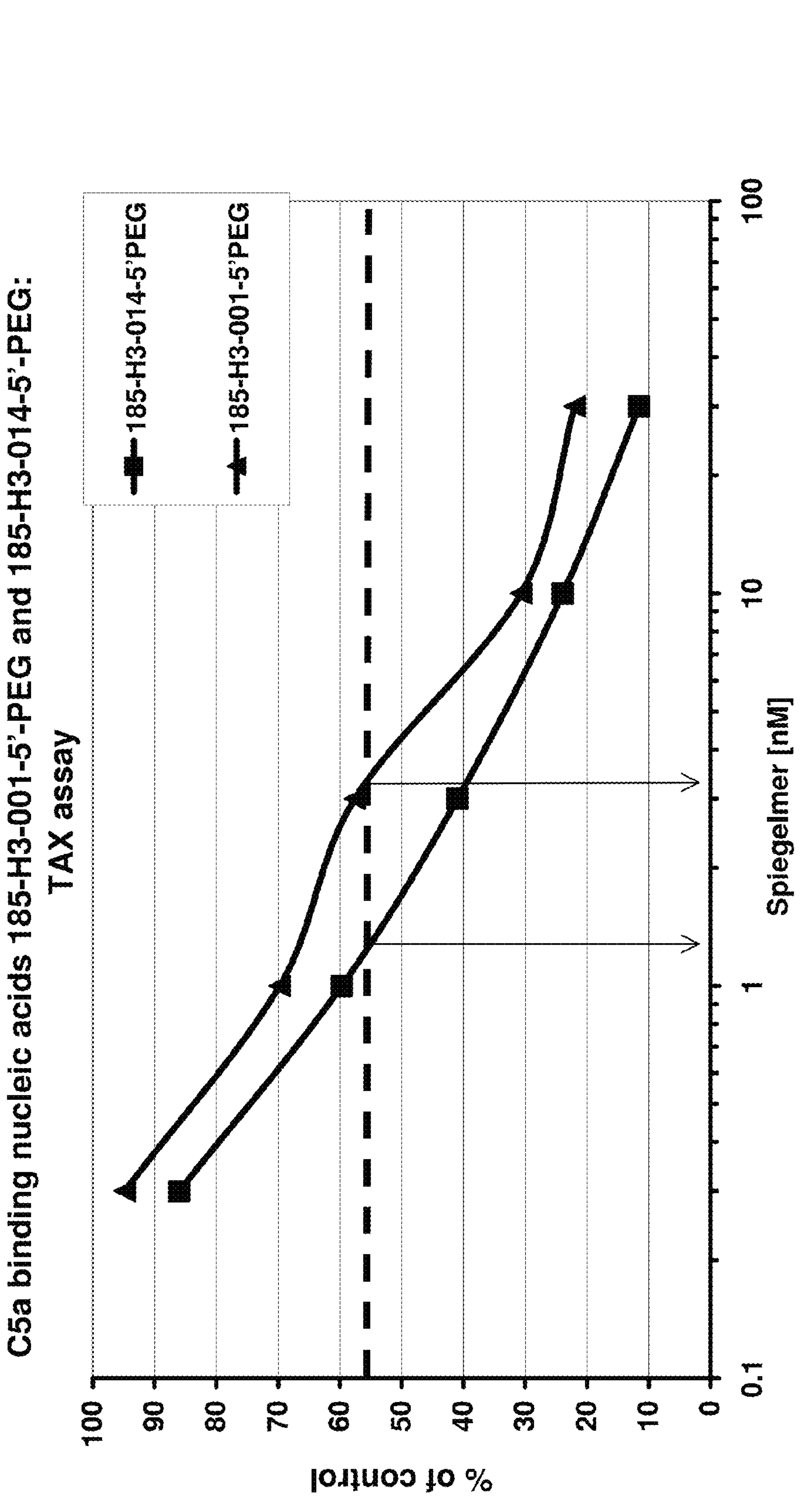
Figure 18:
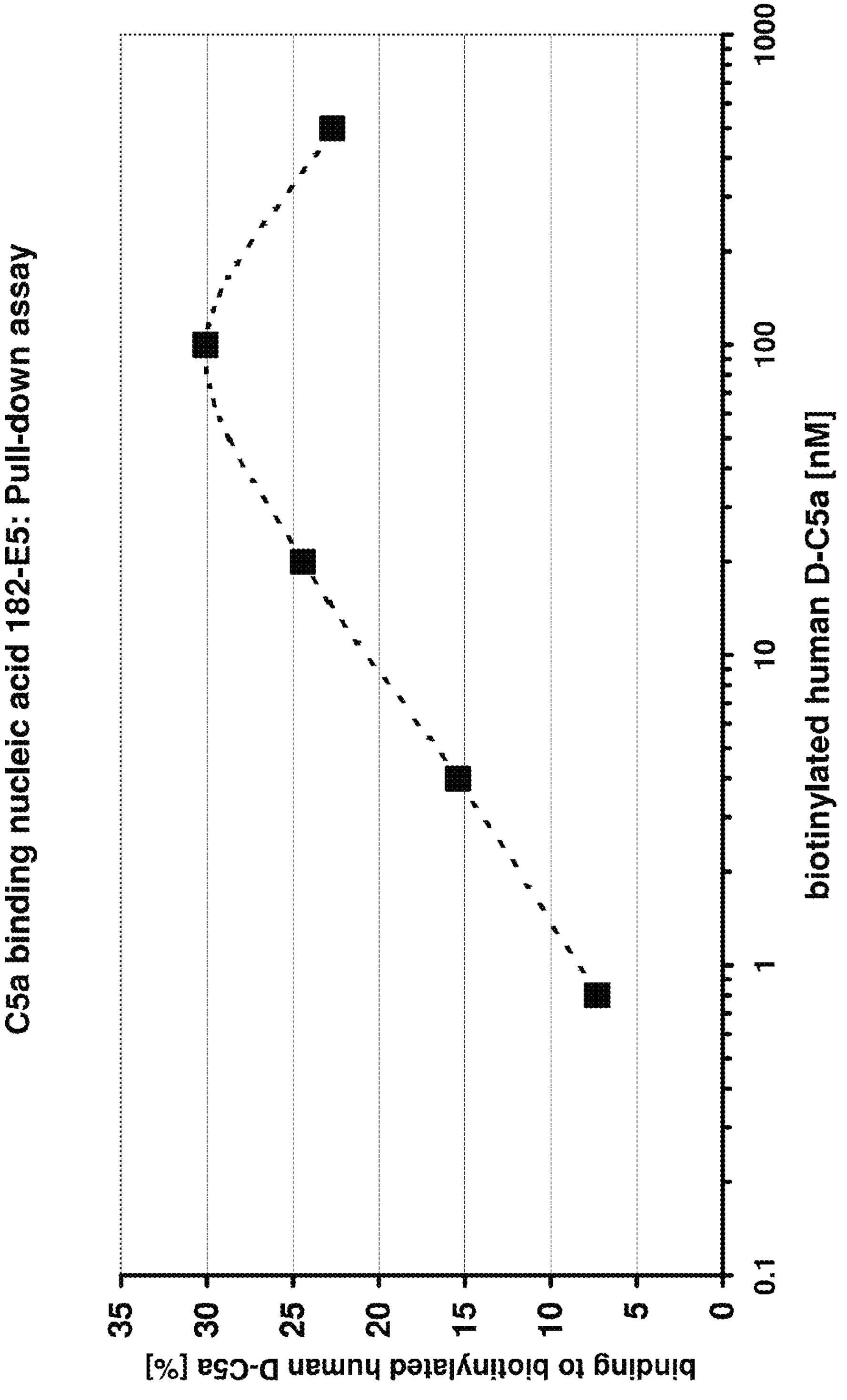
Figure 19:
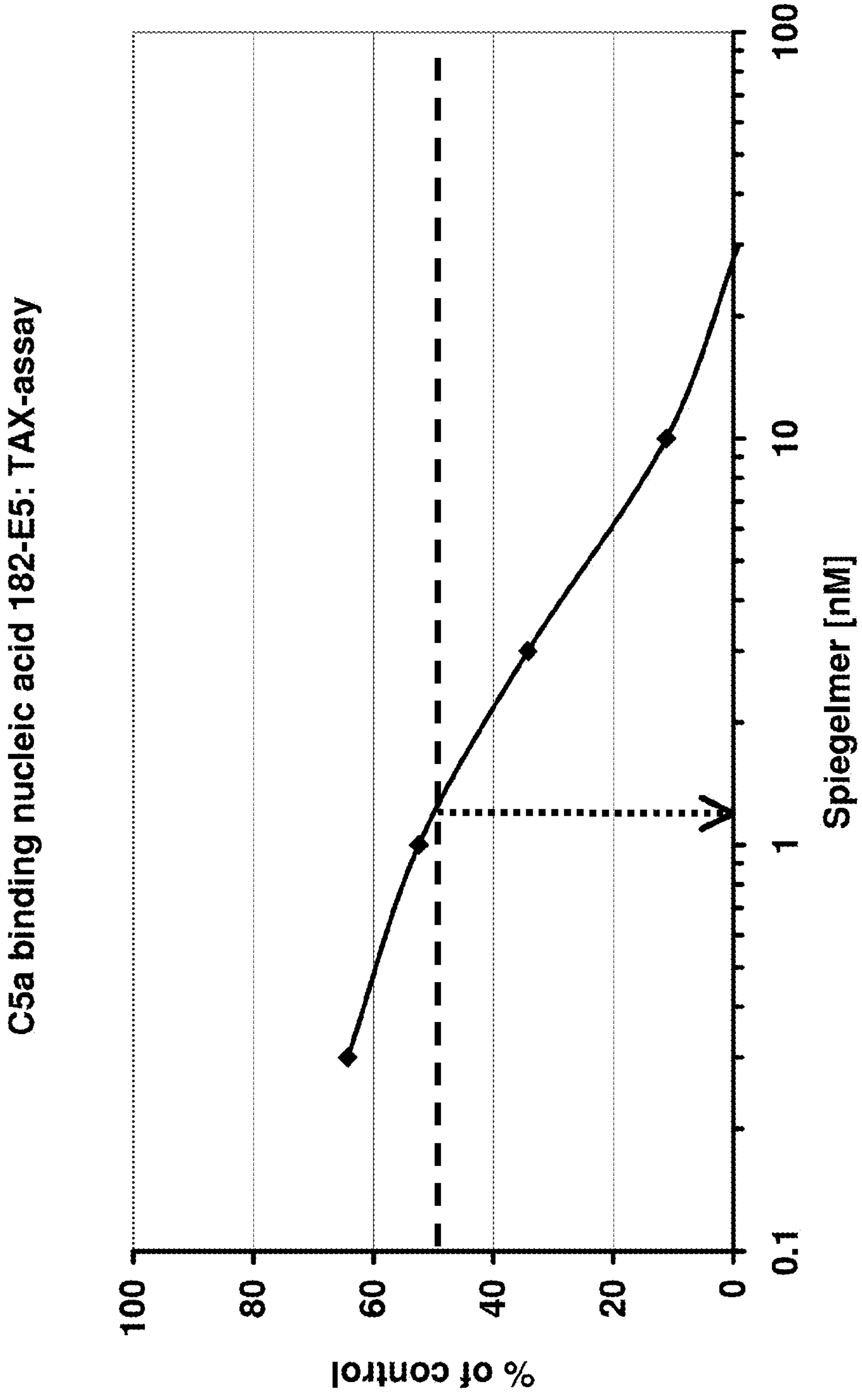
Figure 20:
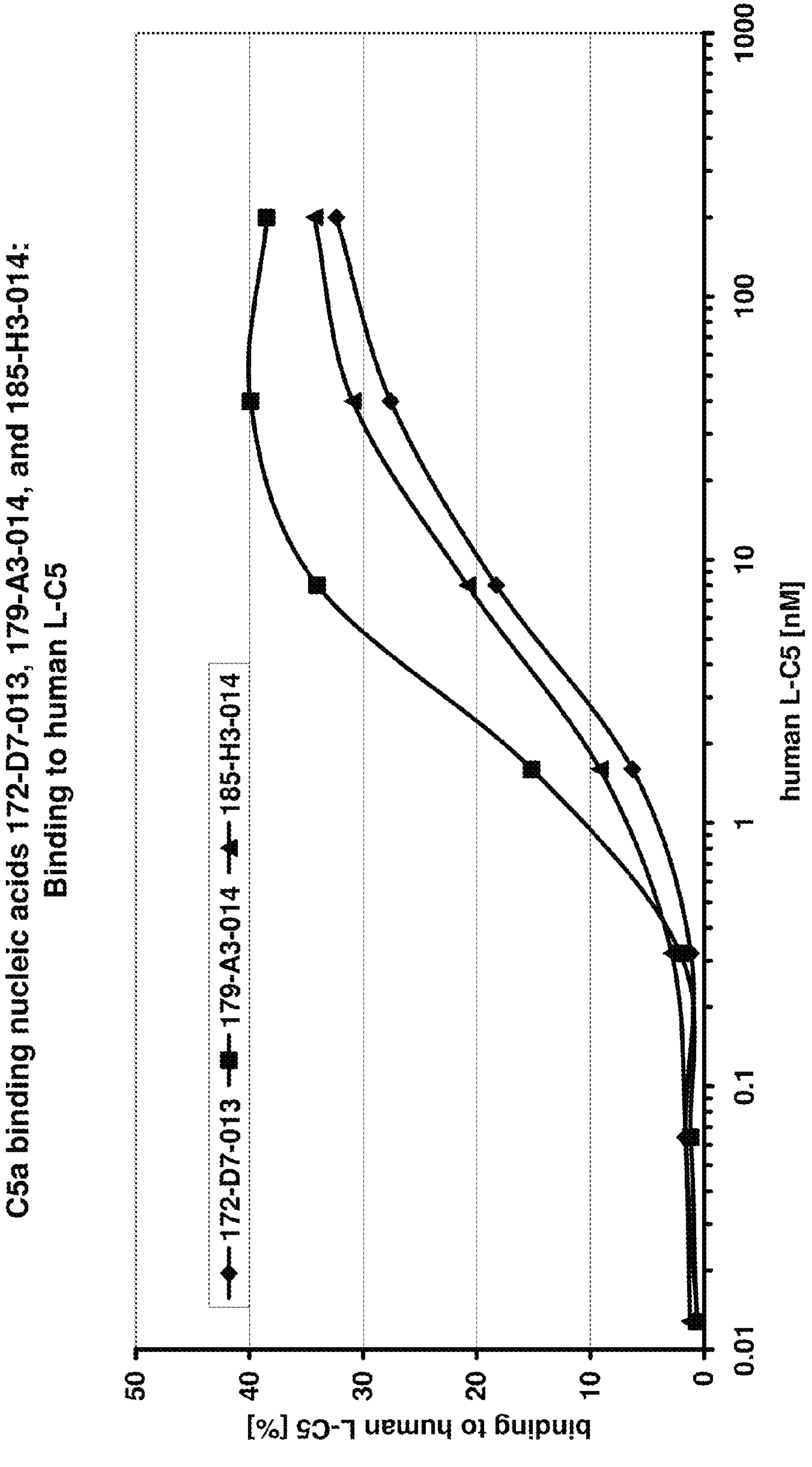
Figure 21:
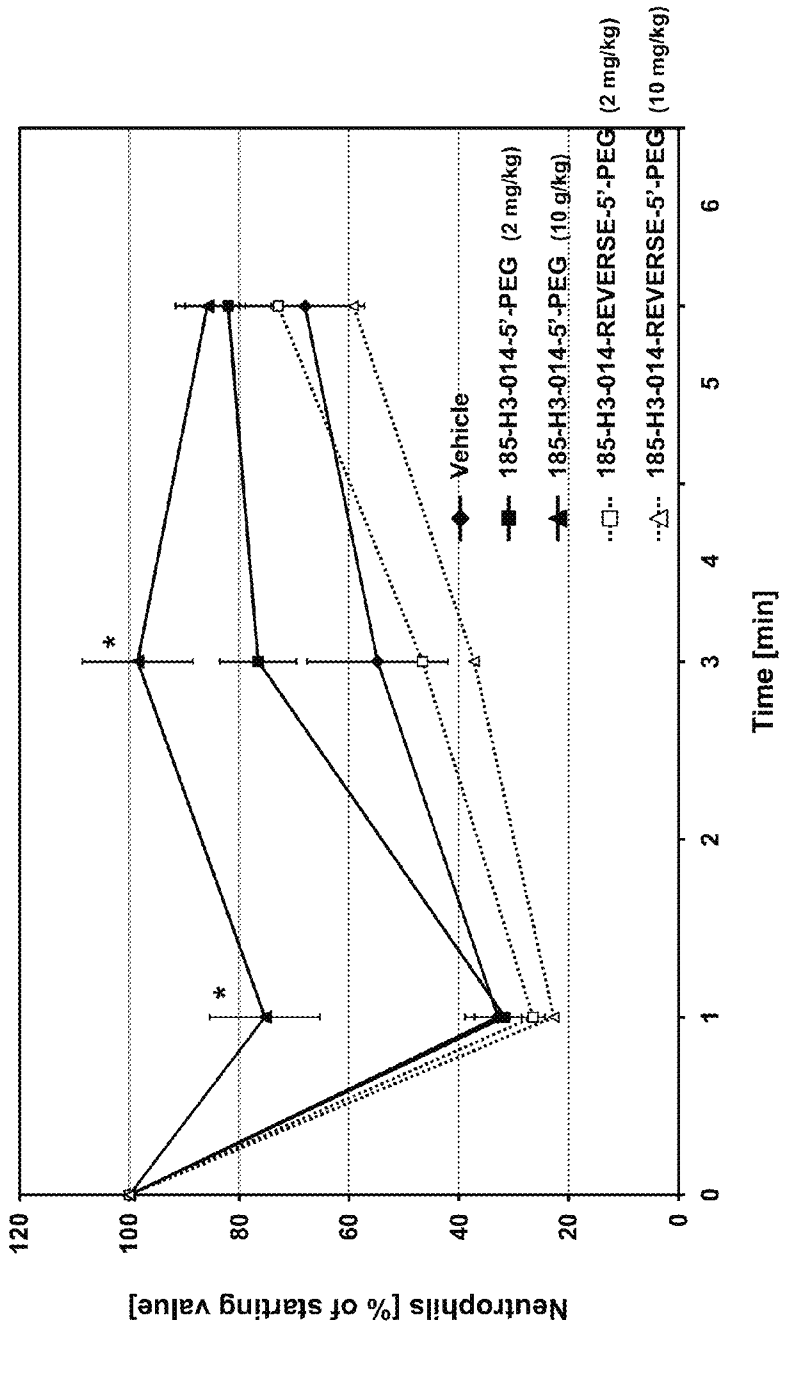
Figure 22:
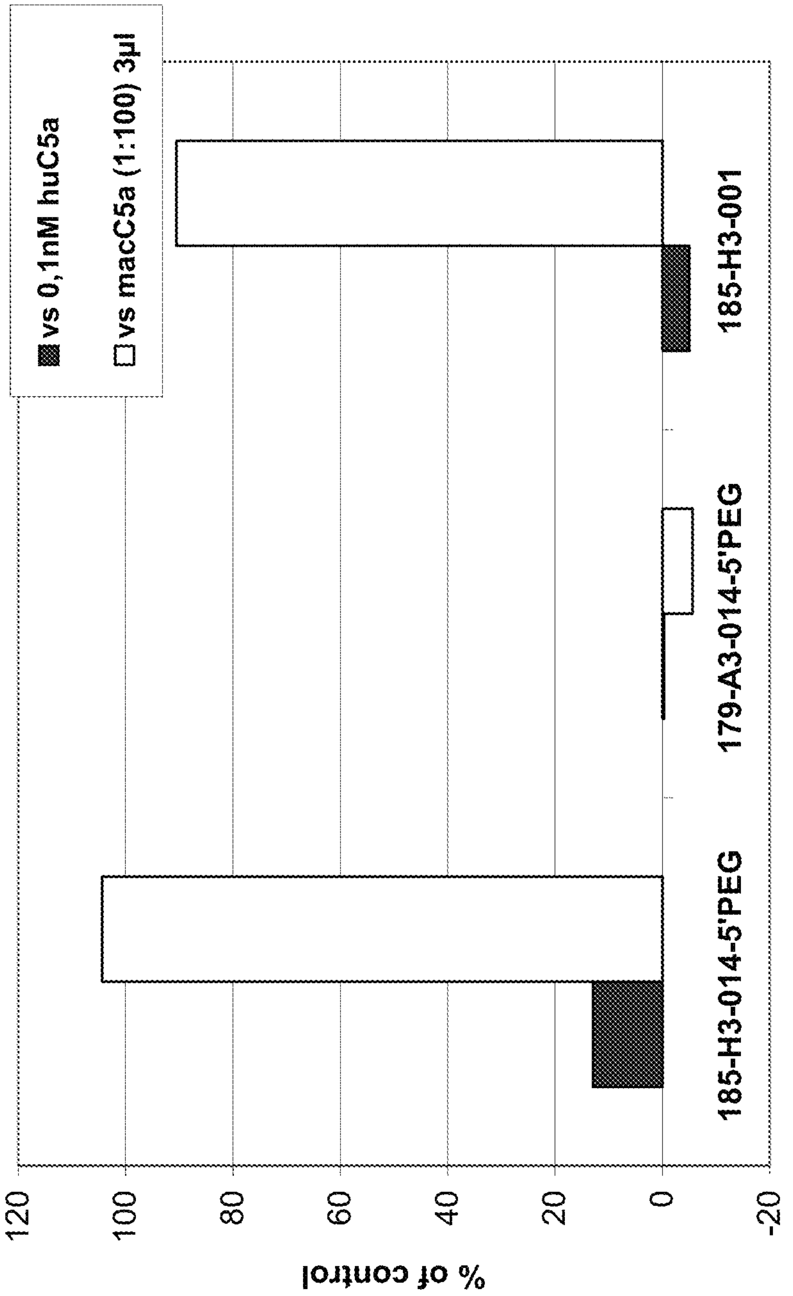

FIG. 17 shows the efficacy of Spiegelmers 185-H3-001-5'-PEG and 185-H3-014-5'-PEG in a chemotaxis assay; cells were allowed to migrate towards 0.1 nM human C5a preincubated at 37° C. with various amounts of Spiegelmers 185-H3-001-5'-PEG and 185-H3-014-5'-PEG, represented as percentage of control over concentration of Spiegelmers 185-H3-001-5'-PEG and 185-H3-014-5'-PEG;

FIG. 18 shows the result of a binding analysis of the aptamer of C5a binding nucleic acid 182-E5 to biotinylated human D-C5a at 37° C., represented as binding of the aptamer over concentration of biotinylated human D-C5a;

FIG. 19 shows the efficacy of Spiegelmer 182-E5 in a chemotaxis assay; cells were allowed to migrate towards 0.1 nM human C5a preincubated at 37° C. with various amounts of Spiegelmer 182-E5, represented as percentage of control over concentration of Spiegelmer 182-E5;

FIG. 20 shows the result of a binding analysis of the Spiegelmers (that are modified with two additional guaonsine in D-konfiguration at the 5'-end of the Spiegelmers whereby the 5'-end was radioactively labeled using a kinase) of C5a binding nucleic acids 172-D7-013, 179-A3-014 and 185-H3-014 to human L-C5 at 37° C., represented as binding of the Spiegelmers over concentration of human L-C5; and FIG. 21 shows the inhibition of C5a-induced neutropenia in mongolian gerbils, whereby the neutrophil content in gerbils following injection of C5a after application of the test substances (Spiegelmer 185-H3-014-5'-PEG or reverse Spiegelmer 185-H3-014-REVERSE-5'-PEG) and vehicle, respectively is represented over the time; whereby the test substance (Spiegelmer 185-H3-014-5'-PEG or reverse Spiegelmer 185-H3-014-REVERSE-5'-PEG) or vehicle was injected at t=−10 min i.v. in the doses indicated; whereny blood was drawn right before induction of neutropenia using 100 μg/kg rec. human C5a (i.v.); whereby further blood draws were done at 3 and 5 min after C5a injection respectively;

FIG. 22 shows the efficacy of Spiegelmers 185-H3-014-5'-PEG, 179-A3-014-5'-PEG and 185-H3-001 in a chemotaxis assay; cells were allowed to migrate towards 0.1 nM human C5a or 0.8 nM monkey C5a preincubated at 37° C. with various amounts of the Spiegelmers, represented as percentage of control over concentration of Spiegelmers;

EXAMPLE 1

Nucleic Acids that Bind Human C5a

Using biotinylated human D-C5a as a target, several nucleic acids that bind to human C5a could be generated: the nucleotide sequences of which are depicted in FIGS. 1 through 9. The nucleic acids were characterized on the aptamer, i.e. D-nucleic acid level using competitive or direct pull-down assays with biotinylated human D-C5a (Example 3) or on the Spiegelmer level, i.e. L-nucleic acid with the natural configuration of human C5a (human L-C5a) by an in vitro cell culture $Ca^{2+}$-release assay (Example 4), or an in vitro chemotaxis assay (Example 5). The Spiegelmers and aptamers were synthesized as described in Example 2.

The nucleic acid molecules thus generated exhibit different sequence motifs, four main types were identified and defined as depicted in FIGS. 1 and 2 (Type A), FIG. 3-5 (Type B), FIGS. 6 and 7 (Type C), and FIG. 8 (Type D). Additional C5a binding nucleic acids which can not be related to each other and to the different sequence motifs described herein, are listed in FIG. 9. For definition of nucleotide sequence motifs, the IUPAC abbreviations for ambiguous nucleotides are used:

S strong G or C;
W weak A or U;
R purine G or A;
Y pyrimidine C or U;
K keto G or U;
M imino A or C;
B not A C or U or G;
D not C A or G or U;
H not G A or C or U;
V not U A or C or G;
N all A or G or C or U If not indicated to the contrary, any nucleic acid sequence or sequence of stretches and boxes, respectively, is indicated in the 5'→3' direction.

1.1 Type a C5a Binding Nucleic Acids

As depicted in FIG. 1 and FIG. 2 all sequences of C5a binding nucleic acids of Type A comprise one central sequence stretch or box defining a potential C5a binding motif which is flanked by 5'- and 3'-terminal stretches that can hybridize to each other. Within the central sequence stretch some nucleotides can hybridize to each other, too. However, such hybridization is not necessarily given in the molecule. Moreover, at single positions of the central sequence stretch one or more of the nucleotides can be replaced by a hydrophilic spacer, e.g. by a C18-PEG spacer.

It is within the present invention that—with regard to Type A C5a binding nucleic acids—the terms ‘5'-terminal stretch’ and ‘first stretch’, ‘central sequence’ and ‘second stretch’, and ‘3'-terminal stretch’ and “third stretch”, respectively are used herein in a synonymous manner if not indicated to the contrary.

The nucleic acids were characterized on the aptamer level using direct and competitive pull-down binding assays with biotinylated human D-C5a in order to rank them with respect to their binding behaviour (Example 3). Selected sequences were synthesized as Spiegelmers (Example 2) and were tested using the natural configuration of human C5a (human L-C5a) in a cell culture in vitro $Ca^{2+}$-assay (Example 4) or a chemotaxis assay (Example 5).

The sequences of the defined boxes or stretches may be different between the C5a binding nucleic acids of Type A which influences the binding affinity to human C5a. Based on binding analysis of the different C5a binding nucleic acids summarized as Type A C5a binding nucleic acids, the central box and its nucleotide sequences as described in the following are individually and more preferably in their entirety essential for binding to human C5a:

The central box of all identified sequences of Type A C5a binding nucleic acids share the central sequence (SEQ ID NO: 20)

GUCCGAUUGGCGGCA*CCC*UUGC*GGG*ACUGGG (Type A Formula-1), whereby within the central sequence stretch some nucleotides can hybridize to each other (marked as bold and italic letters) and at single positions of the central sequence stretch one or more of the nucleotides can be replaced by a hydrophilic spacer, e.g. by a C18-PEG spacer.

The nucleotides within the central sequence strecth that can hybridize to each other are two substretches of three nucleoctides, respectively, whereby the first substretch comprise the nucleotides at position 16 to 18 and the second substretch comprise the nucleotides 23 to 25. The sequence of the three nucleotides of the first and the second substretch is independantly CCC or GGG, whereby the sequence of the first and the second substretch is different but in any case the first and the second substretch are complementary to each other.

Figure 10:
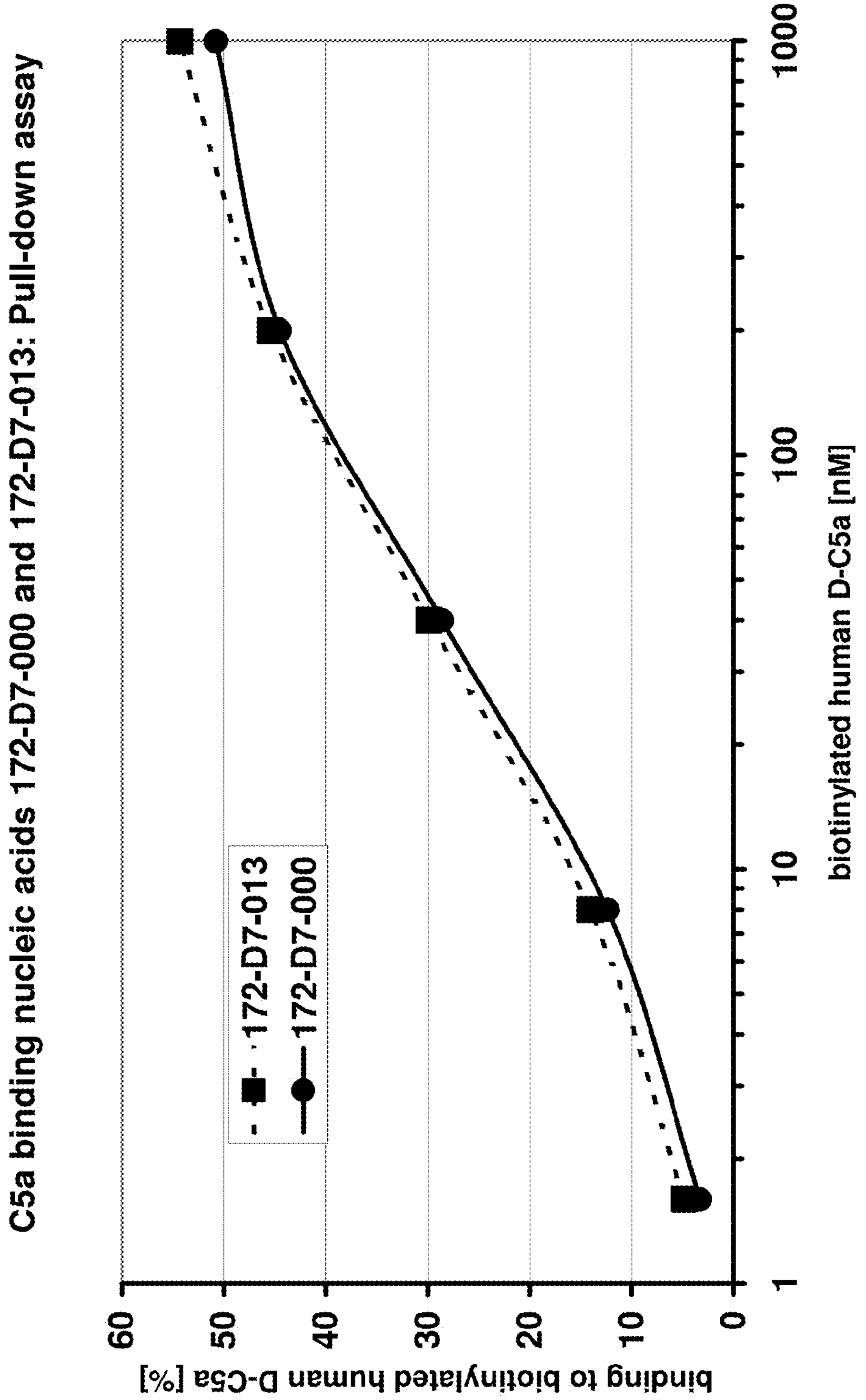

The origin of all Type A C5a binding nucleic acids is the Type A C5a binding nucleic acid 172-D7-000 that was characterized for its binding affinity to human C5a in several different assays. The equilibrium binding constant $K_D$ was determined using the pull-down binding assay ($K_D$=30 nM, FIG. 10). The $IC_{50}$ (inhibitory concentration 50%) of 2-3 nM for Type A C5a binding nucleic acid 172-D7-000 was measured using a cell culture $Ca^{2+}$-release. Derivatives of Type A C5a binding nucleic acid 172-D7-000 were analyzed as aptmers by using the pull-down assay (determination of the binding constant $K_D$) or in comparison to Type A C5a binding nucleic acid 172-D7-000 by using the competition assay.

Nine nucleotides of the 5'-terminal stretch of Type A C5a binding nucleic acid 172-D7-000 may hybridize to the respective nine nucleotides of the 3'-terminal stretch to form a terminal helix of nine base-pairing nucleotides. However, the 3' terminal nucleotide 'U' of 5'-terminal strecth can not be replaced by an 'C' without reduction of binding activity (172-D7-003; $K_D$=372 nM). As frstly shown for the derivatives 172-D7-001, 172-D7-010 and 172-D7-011 of Type A C5a binding nucleic acid 172-D7-000, a helix of seven base pairs seemed to be sufficient in order to maintain C5a binding activity. If the central sequence stretch was flanked by only six nucleotides at the 5'- and the 3'-end (5'-end: 'GUGCUU'; 3'-end: 'GAGUAC') forming a helix with six base pairs), the binding affinity was reduced (172-D7-002; $K_D$=108 nM). Suprisingly, later experiments revealed that a helix of six base pairs formed by 'GCGCUU' of the 5'-terminal stretch and by 'GAGCGC' of the 3'-terminal stretch is sufficient for forming a fully active structure of Type A C5a binding nucleic acids (172-D7-012, 172-D7-013, 172-D7-014). A reduction to five nucleotides for the 5'- and 3'-terminal stretch may have a negative effect on forming the fully active three-dimensional structure of Type A C5a binding nucleic acids (172-D7-017).

However, combining the 5'- and 3'-terminal stretches of all tested Type A C5a binding nucleic acids the generic formula for the 5'-terminal stretch of Type A C5a binding nucleic acids is 5' $X_1X_2X_3$GYGC$X_4$Y 3' (SEQ ID NOS 173 and 190, respectively) (Type A Formula-2-5') and the generic formula for the 3'-terminal stretch Type A C5a binding nucleic acids is 5' G$X_5$GYRC$X_6X_7X_8$ 3' (SEQ ID NOS 174 and 192, respectively) (Type A Formula-2-3'), whereas $X_1$ is A or absent, $X_2$ is G or absent, $X_3$ is C or absent, $X_4$ is U, $X_5$ is A, $X_6$ is G or absent, $X_7$ is C or absent, and $X_8$ is U or absent, or $X_1$ is A or absent, $X_2$ is G or absent, $X_3$ is C or absent, $X_4$ is absent, $X_5$ is absent, $X_6$ is G or absent, $X_7$ is C or absent, and $X_8$ is U or absent.

As mentioned above, a helix of six or seven base pairs seemed to be sufficient in order to maintain C5a binding activity. Therefore, the preferred 5'- and 3'-terminal stretches are specified by the generic formula for the 5'-terminal stretch of Type A C5a binding nucleic acids 5' $X_1X_2X_3$GYGC$X_4$Y 3' (SEQ ID NO: 191) (Type A Formula-2-5') and the generic formula for the 3'-terminal stretch Type A C5a binding nucleic acids is 5' G$X_5$GYRC$X_6X_7X_8$ 3' (SEQ ID NO: 193) (Type A Formula-2-3'), whereby $X_1$ is absent, $X_2$ is absent, $X_3$ is C or absent, $X_4$ is U, $X_5$ is A, $X_6$ is G or absent, $X_7$ is absent, and $X_8$ is absent.

The best binding affinities can be achieved in the case of 5'- and 3'-terminal stretches that are specified by the generic formula for the 5'-terminal stretch of Type A C5a binding nucleic acids Type A Formula-3-5' (5' $X_3$GYGC$X_4$U 3' (SEQ ID NO: 175)) and the generic formula for the 3'-terminal stretch Type A C5a binding nucleic acids Type A Formula-3-3' (5' G$X_5$GYGC$X_6$ 3' (SEQ ID NO: 176)), whereby $X_3$ is C or absent, $X_4$ is U, $X_5$ is A, and $X_6$ is G or absent.

Another strategy to reduce the number of nucleotides was to replace some nucleotides within the central sequence stretch of Type A C5a binding nucleic acids by a C18-PEG spacer. Within the central sequence stretch respectivly three nucleotides can hybridize to each other, potentially forming a helix. As shown for derivatives 172-D7-005, 172-D7-008, 172-D7-009, 172-D7-013 and 172-D7-014 the four nucleotides that are flanked by the helix in the central sequence stretch of Type A C5a binding nucleic acids can be replaced by a C18-PEG spacer without significant reduction of the molecule's binding affinity to C5a. Deletion of one out of the three nucleotides forming a helix within the central sequence stretch led to a reduction of binding affinity (172-D7-018). Other sequence segments of the central stretch of Type A C5a binding nucleic acids are much more sensitive concerning replacement strategies as described above. Hence, the derivatives that were designed to determine this option showed reduced binding affinity to C5a (172-D7-004, 172-D7-015, 172-D7-016).

Figure 11:
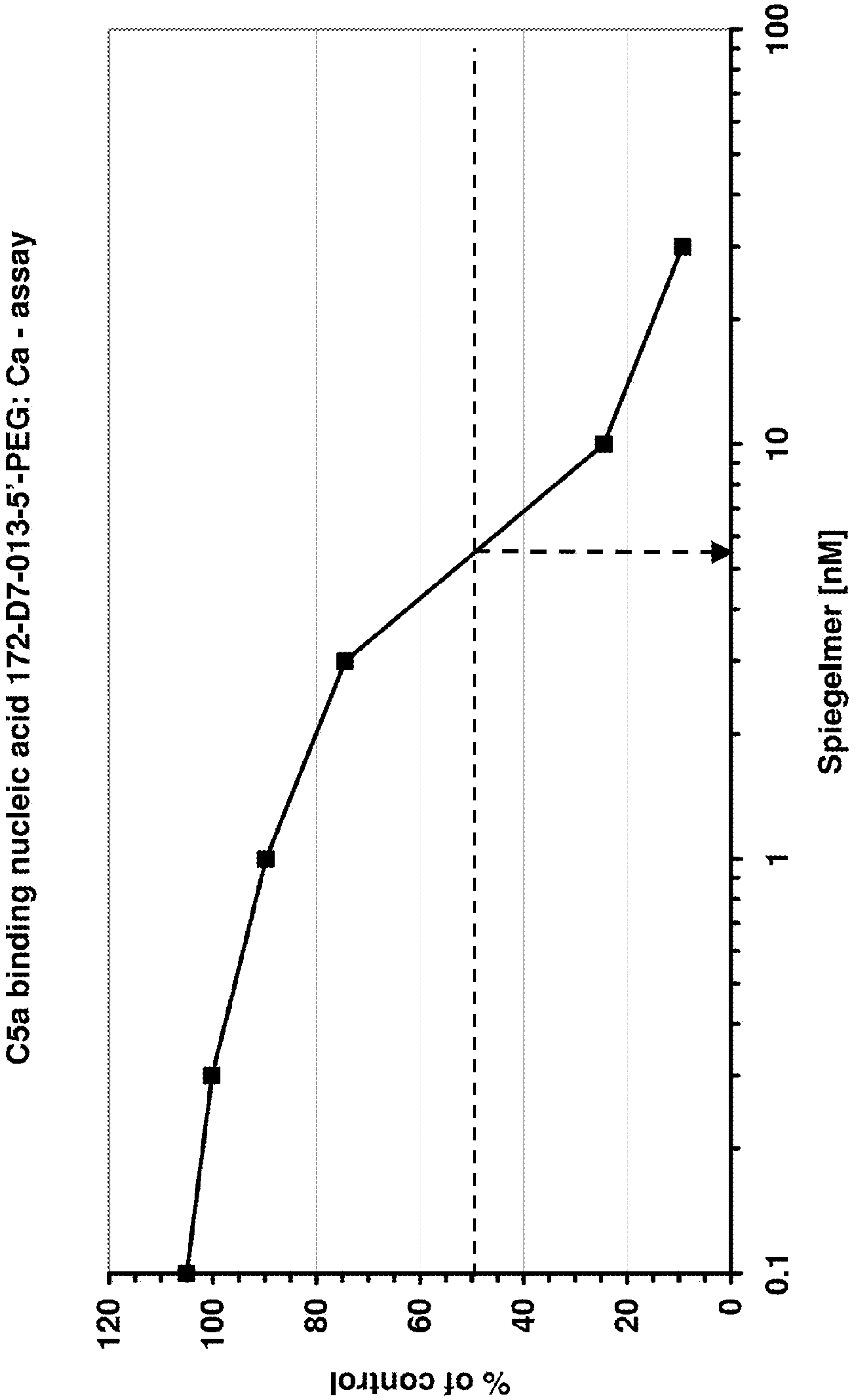
FIG. 11 shows the efficacy of Spiegelmer 172-D7-013-5'-PEG in a calcium release assay; cells were stimulated with 3 nM human C5s preincubated at 37° C. with various amounts of Spiegelmer 172-D7-013-5'-PEG, represented as percentage of control over concentration of 172-D7-013-5'-PEG.

For the PEGylated derivative of C5a binding nucleic acid 172-D7-013, 172-D7-013-5'-PEG, an $IC_{50}$ of approx. 6.5 nM was determined in the $Ca^{++}$-release assay (FIG. 11).

1.2 Type B C5a Binding Nucleic Acids

As depicted in FIG. 3, FIG. 4 and FIG. 5 all sequences of C5a binding nucleic acids of Type B comprise two highly conserved sequence stretches or boxes—Box A and Box B—which are linked to each other by a stretch of up to eleven nucleotides—called Box L—and flanked by 5'- and 3'-terminal stretches that can hybridize to each other. Within the Box L some nucleotides can hybridize to each other, too. However, such hybridization is not necessarily given in the molecule. Moreover, at single positions of the Box L one or more of the nucleotides can be replaced by a hydrophilic spacer, e.g. by a C18-PEG spacer.

It is within the present invention that—with regard to Type B C5a binding nucleic acids—the terms '5'-terminal stretch' and 'first stretch', 'Box A' and 'second stretch', 'Box L' and third stretch, 'Box B' and 'fourth stretch', and '3'-terminal stretch' and 'fifth stretch', respectively are used herein in a synonymous manner if not indicated to the contrary.

The nucleic acids were characterized on the aptamer level using direct and competitive pull-down binding assays with biotinylated human D-C5a in order to rank them with respect to their binding behaviour (Example 3). Selected sequences were synthesized as Spiegelmers (Example 2) and were tested using the natural configuration of human C5a (human L-C5a) in a chemotaxis assay (Example 5).

The sequences of the defined boxes or stretches may be different between the C5a binding nucleic acids of Type B which influences the binding affinity to human C5a. Based on binding analysis of the different C5a binding nucleic acids summarized as Type B C5a binding nucleic acids, the sequence stretches or boxes and its nucleotide sequences as described in the following are individually and more preferably in their entirety essential for binding to human C5a:

Type B C5a binding nucleic acids comprise two highly conserved sequence stretches—Box A and Box B—defining a potential C5a binding motif. Box A and Box B are linked to each other by up to eleven nucleotides, called 'Box L'. The such manner linked sequence stretches Box A and Box B are flanked by 5'- and 3'-terminal stretches that can hybridize to each other. Between the 5'-terminal stretch and Box A and between the 3'-terminal stretch and Box B none up to four additional nucleotides can be located. These nucleotides seem not hybridize to each other or to other nucleotides within the Type B C5a binding nucleic acid molecules.

The Box A of all identified sequences of Type B C5a binding nucleic acids share the consensus sequence (SEQ ID NO: 30)

ASACGCCGVRYAGGWC (Type B Formula-1).

The consensus sequence of Box B for Type B C5a binding nucleic acids is (SEQ ID NO: 32)

GWAGAAUSG (Type B Formula-3).

In order to determine the binding affinities of the different Type B C5a binding nucleic acids 179-A3, 179-C1, 179-D3, 179-E1, 179-A4, 182-E6, 179-G1, 182-D5, 179-F2 to human C5a they were tested on the aptamer level using direct and competitive pull-down binding assays with biotinylated human D-C5a (Example 3). As reference the Type A C5a binding nucleic acid 172-D7-000 was used. ($K_D$=30 nM, $IC_{50}$=2-3 nM). Type B C5a binding nucleic acids 179-A3, 179-C1, 179-D3, 179-E1, 182-E6 and 182-D5 showed almost similar binding affinity to human C5a, whereby the binding affinity is better than the binding affinity of Type A C5a binding nucleic acid 172-D7-000. Type B C5a binding nucleic acids 179-A4, 179-G1 and 179-F2 showed similar binding to human C5a as Type A C5a binding nucleic acid 172D7-000. Because the Box A sequences of Type B C5a binding nucleic acids 179-F2

(SEQ ID NO: 219)

(Box A: GACGCCGAACAGGAC)

and 179-G1

(SEQ ID NO: 220)

(Box A: GACGCCGGAUAGGUC)

are different from the Type B C5a binding nucleic acids with the best affinity to C5a, viz. Type B C5a binding nucleic acids 179-A3, 179-C1 and 179-D3, the preferred consensus sequence of Box A for Type B C5a binding nucleic acids is (SEQ ID NO: 31)

ASACGCCGMRYAGGWC (Type B Formula-2), whereby the preferred consensus sequence of Box A for Type B C5a binding nucleic acids results from the Box A sequences of Type B C5a binding nucleic acids 179-A3, 179-C1 and 179-D3.

The nucleotides of Boxes A and B of Type B C5a binding nucleic acids interacts in a sequence-specific manner. If the second nucleotide at the 5'-end of Box A is 'C' then the corresponding nucleotide in Box B is 'G' (the nucleotide next to the last at the 3'-end of Box B; see 179-A3 and 179-C1). Alternatively, the second nucleotide at the 5'-end of Box A is 'G' and the corresponding nucleotide in Box B is 'C' (the nucleotide next to last at the 3'-end of Box B; see 179-D3, 179-E1, 179-A4, 182-E6, 179-G1, 182-D5, 179-F2). In addition, if the nucleotide next to last at the 3'-end of Box A is 'A' then the corresponding nucleotide in Box B is 'U' (the second nucleotide at the 5'-end of box B; see 179-A3, 182-D5 and 179-F2). Alternatively, the nucleotide next to last at the 3'-end of box A is 'U' and the corresponding nucleotide in Box B is 'A' (the second nucleotide at the 5'-end of Box B; see 179-C1, 179-D3, 179-E1, 179-A4, 182-E6 and 179-G1).

The 3'-end of Box A is linked to the 5'-end of Box B by up to eleven nucleotides—called 'Box L'—whereby the central nucleotides of the Box L are not hybrized to each other and thereby form a so called 'loop'-structure. Three up to seven nucleotides can form such a 'loop'-structure. The additional nucleotides that do not form the 'loop'-structure hybridize to each other and/or to the 3'-end of Box A and the 5'-end of Box B, respectively. The respective sequences of the linking boxes (Box L) of the Type B C5a binding nucleic acids are very different to each other whereby the sequence and number of nucleotides are highly variable (see FIG. 3). On basis of the Type B C5a binding nucleic acid 179-A3 different derivatives werde designed and tested (FIGS. 4 and 5). As shown for Type B C5a binding nucleic acid 179-A3-014, two nucleotides could be deleted without any reduction of binding affinity to human C5a. Moreover, if further three nucleotides that are part of the loop were replaced by a C18-PEG-spacer the molecule 179-A3-042 was as active as the original molecule 179-A3-014. As shown for Type B C5a binding nucleic acid 179-A3-042 the Box L comprises a first and a second substretch, whereby the first and the second substretch hybridize to each other. In the case of hybridization a double-stranded structurte is formed. The minimal sequence of the first and the second substretch is independantly CC or GG, whereby the sequence of the first and the second substretch is different for the first and the second substretch. However, as consequence of these results, presumably the nucleotides of Box L are not responsible for binding to human C5a, but important in order to arrange Box A and Box B to each other.

Figure 12:
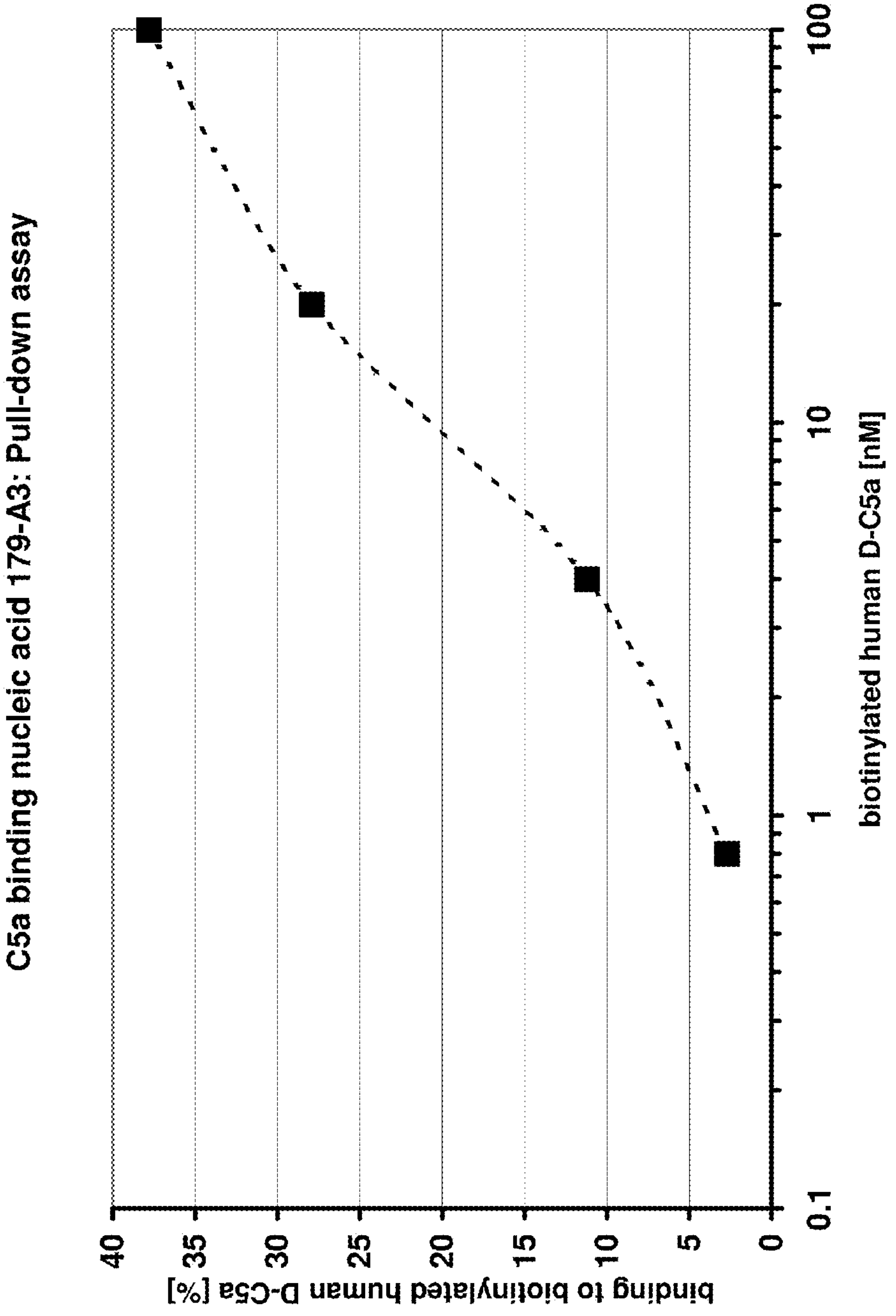
Figure 13:
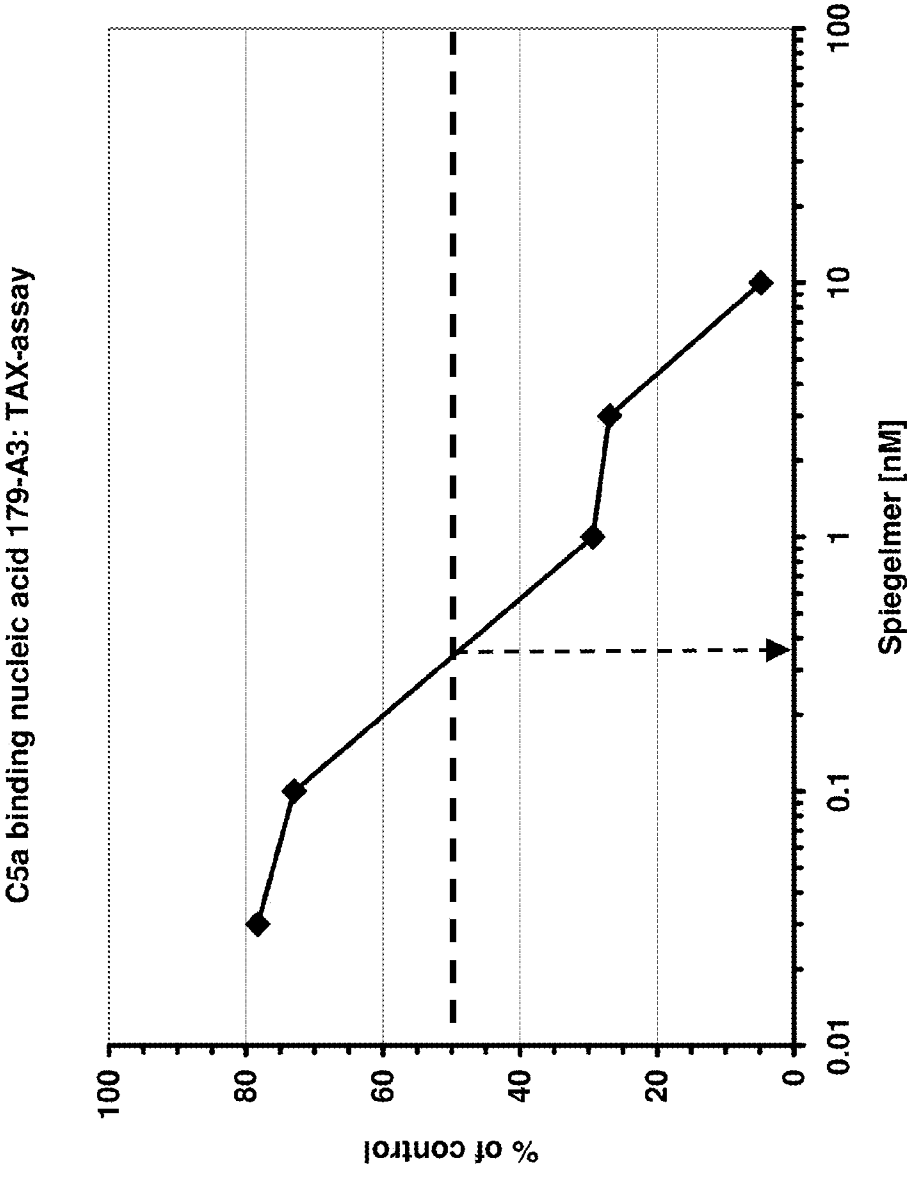
FIG. 13 shows the efficacy of Spiegelmer 179-A3 in a chemotaxis assay; cells were allowed to migrate towards 0.1 nM human C5a preincubated at 37° C. with various amounts of Spiegelmer 179-A3, represented as percentage of control over concentration of Spiegelmer 179-A3.

Type B C5a binding nucleic acids comprise at the 5'-end and at the 3'-end four to eight nucleotides, respectively, that can hybridize to each other forming a helix. In order to truncate the molecule Type B C5a binding nucleic acid 179-A3 ($K_D$=7.2 nM, FIG. 12; $IC_{50}$=0.9 nM, FIG. 13) several derivatives with a different number of nucleotides and different nucleotide sequences (179-A3-014, 179-A3-003, 179-A3-007, 179-A3-008) were tested in competition experiments vs. Type B C5a binding nucleic acid 179-A3. On basis of the sequences present as 5'- and 3'-terminal stretch of Type B C5a binding nucleic acid 179-A3 the truncation down to three nucleotides at the 5'-end and the 3'-end, respectively, of the molecule led to a reduction of binding affinity (see 179-A3-008). On basis of derivative 179-A3-014 that shows identical binding affinity as the original molecule Type B C5a binding nucleic acid 179-A3 further helix arrangements at the 5'-end and the 3'-end of the molecule were tested (179-A3-015, 179-A3-020, 179-A3-021, 179-A3-024, 179-A3-026, 179-A3-029, 179-A3-030, 179-A3-034, 179-A3-037). In competition experiments versus Type B C5a binding nucleic acid 179-A3-014 it could be shown that minimal four nucleotides at both ends that hybridize to each other are essential for a fully active structure of a Type B C5a binding nucleic acid (179-A3-030, 5'-end: CGCC, 3'-end: GGCG; 179-A3-034, 5'-end: CCGG, 3'-end: CCGG). Furthermore Type B C5a binding nucleic acid 179-A3-007 (5'-end: GCUG, 3'-end: CAGC) is a fully active derivative of Type B C5a binding nucleic acid 179-A3.

However, combining the 5'- and 3'-terminal stretches of all tested Type B C5a binding nucleic acids (as depicted in FIGS. 3, 4 and 5) the generic formula for the 5'-terminal stretch of Type B C5a binding nucleic acids is 5' $X_1X_2SBBX_3X_4X_5$ 3' (SEQ ID NOS 177, 194, 196, 195, and 197-200, respectively, in order of appearance) (Type B Formula-4-5') and the generic formula for the 3'-terminal stretch Type B C5a binding nucleic acids is 5' $X_6X_7X_8VVSX_9X_{10}$ 3' (SEQ ID NOS 178, 201, 203, 202, and 204-207, respectively, in order of appearance) (Type B Formula-4-3'), whereby $X_1$ is G or absent, $X_2$ is U or absent, $X_3$ is B, $X_4$ is Y, $X_5$ is M, $X_6$ is K, $X_7$ is G, $X_8$ is N, $X_9$ is A or absent, and $X_{10}$ is C or absent, or $X_1$ is G or absent, $X_2$ is U or absent, $X_3$ is B, $X_4$ is Y, $X_5$ is absent, $X_6$ is absent, $X_7$ is G, $X_8$ is N, $X_9$ is A or absent, and $X_{10}$ is C or absent, or $X_1$ is G or absent, $X_2$ is U or absent, $X_3$ is absent, $X_4$ is Y, $X_5$ is M, $X_6$ is K, $X_7$ is G, $X_8$ is absent, $X_9$ is A or absent, and $X_{10}$ is C or absent, or $X_1$ is G or absent, $X_2$ is U or absent, $X_3$ is B, $X_4$ is absent, $X_5$ is M, $X_6$ is K, $X_7$ is absent, $X_8$ is N, $X_9$ is A or absent, and $X_{10}$ is C or absent, or $X_1$ is G or absent, $X_2$ is U or absent, $X_3$ is B, $X_4$ is absent, $X_5$ is absent, $X_6$ is absent, $X_7$ is absent, $X_8$ is N, $X_9$ is A or absent, and $X_{10}$ is C or absent, or $X_1$ is G or absent, $X_2$ is U or absent, $X_3$ is absent, $X_4$ is absent, $X_5$ is M, $X_6$ is K, $X_7$ is absent, $X_8$ is absent, $X_9$ is A or absent, and $X_{10}$ is C or absent, or $X_1$ is G or absent, $X_2$ is U or absent, $X_3$ is absent, $X_4$ is Y, $X_5$ is absent, $X_6$ is absent, $X_7$ is G, $X_8$ is absent, $X_9$ is A or absent, and $X_{10}$ is C or absent, or $X_1$ is G or absent, $X_2$ is U or absent, $X_3$ is absent, $X_4$ is absent, $X_5$ is absent, $X_6$ is absent, $X_7$ is absent, $X_8$ is absent, $X_9$ is A or absent, and $X_{10}$ is C or absent.

As mentioned above, a helix of four to six base pairs seemed to be sufficient in order to maintain C5a binding activity as shown for Type B C5a binding nucleic acid 179-A3 and its derivatives. Therefore, the preferred 5'- and 3'-terminal stretches can be specified by the generic formula for the 5'-terminal stretch of Type B C5a binding nucleic acids 5' $X_1X_2SSBX_3X_4X_5$ 3' (SEQ ID NOS 188 and 208, respectively) (Type B Formula-7-5') and the generic formula for the 3'-terminal stretch Type B C5a binding nucleic acids 5' $X_6X_7X_8VSSX_9X_{10}$ 3' (SEQ ID NOS 189 and 209, respectively) (Type B Formula-7-3'), whereby $X_1$ is G or absent, $X_2$ is U or absent, $X_3$ is S, $X_4$ is absent, $X_5$ is absent, $X_6$ is absent, $X_7$ is absent, $X_8$ is S, $X_9$ is A or absent, and $X_{10}$ is C or absent, whereby preferably $X_1$ is absent, $X_2$ is absent, $X_3$ is S, $X_4$ is absent, $X_5$ is absent, $X_6$ is absent, $X_7$ is absent, $X_8$ is S, $X_9$ is absent, and $X_{10}$ is absent.

The best binding affinities of Type B C5a binding nucleic acids comprising 5'- and 3'-terminal stretches with four nucleotides, are shown for Type B C5a binding nucleic acids 179-A3-030 (5'-end: CGCG, 3'-end: GGCG), 179-A3-034 (5'-end: CCGG, 3'-end: CCGG) and 179-A3-007 (5'-end: GCUG, 3'-end: CAGC).

However, Type B C5a binding nucleic acid 179-C1 and its potential derivatives can be specified by the generic formula for the 5'-terminal stretch of Type B C5a binding nucleic acids 5' $X_1X_2GCYX_3X_4X_5$ 3' (SEQ ID NO: 179) (Type B Formula-5-5') and the generic formula for the 3'-terminal stretch Type B C5a binding nucleic acids is 5' $X_6X_7X_8AGCX_9X_{10}$ 3' (SEQ ID NO: 180). (Type B Formula-5-3'), whereby $X_1$ is G or absent, $X_2$ is U or absent, $X_3$ is G, $X_4$ is C, $X_5$ is absent, $X_6$ is absent, $X_7$ is G, $X_8$ is C, $X_9$ is A or absent, and $X_{10}$ is C or absent.

Moreover, Type B C5a binding nucleic acid 179-D3 and its potential derivatives can be specified by the identical generic formula for the 5'-terminal stretch of Type B C5a binding nucleic acids 5' $X_1X_2GCCX_3X_4X_5$ 3' (SEQ ID NO: 181) (Type B Formula-6-5') and the generic formula for the 3'-terminal stretch Type B C5a binding nucleic acids is 5' $X_6X_7X_8AGCX_9X_{10}$ 3' (SEQ ID NO: 211). (Type B Formula-5-3'), whereby $X_1$ is G or absent, $X_2$ is U or absent, $X_3$ is G, $X_4$ is C, $X_5$ is C, $X_6$ is G, $X_7$ is G, $X_8$ is C, $X_9$ is A or absent, and $X_{10}$ is C or absent.

The 3'-end of 5'-terminal helix forming sequence stretch is linked to the 5'-end of Box A by zero to four nucleotides, whereby these one to five nucleotides do not hybridize to other nucleotides within the Type B C5a binding nucleic acid molecules. Additionally, the 3'-end of Box B is linked to 5'-end of 3'-terminal helix forming sequence stretch by zero or one nucleotides, whereby these one or two nucleotides do not hybridize to other nucleotides within the Type B C5a binding nucleic acid molecules. These not hybridized nucleotides 5' of the 5'-end of Box A and 3' of the 3'-end of Box B preferably are either not existent or 'A' and 'G'. (true for all Type B C5a binding nucleic acids as listed in FIG. 3-5, except Type B C5a binding nucleic acid 179-G1).

Figure 14:
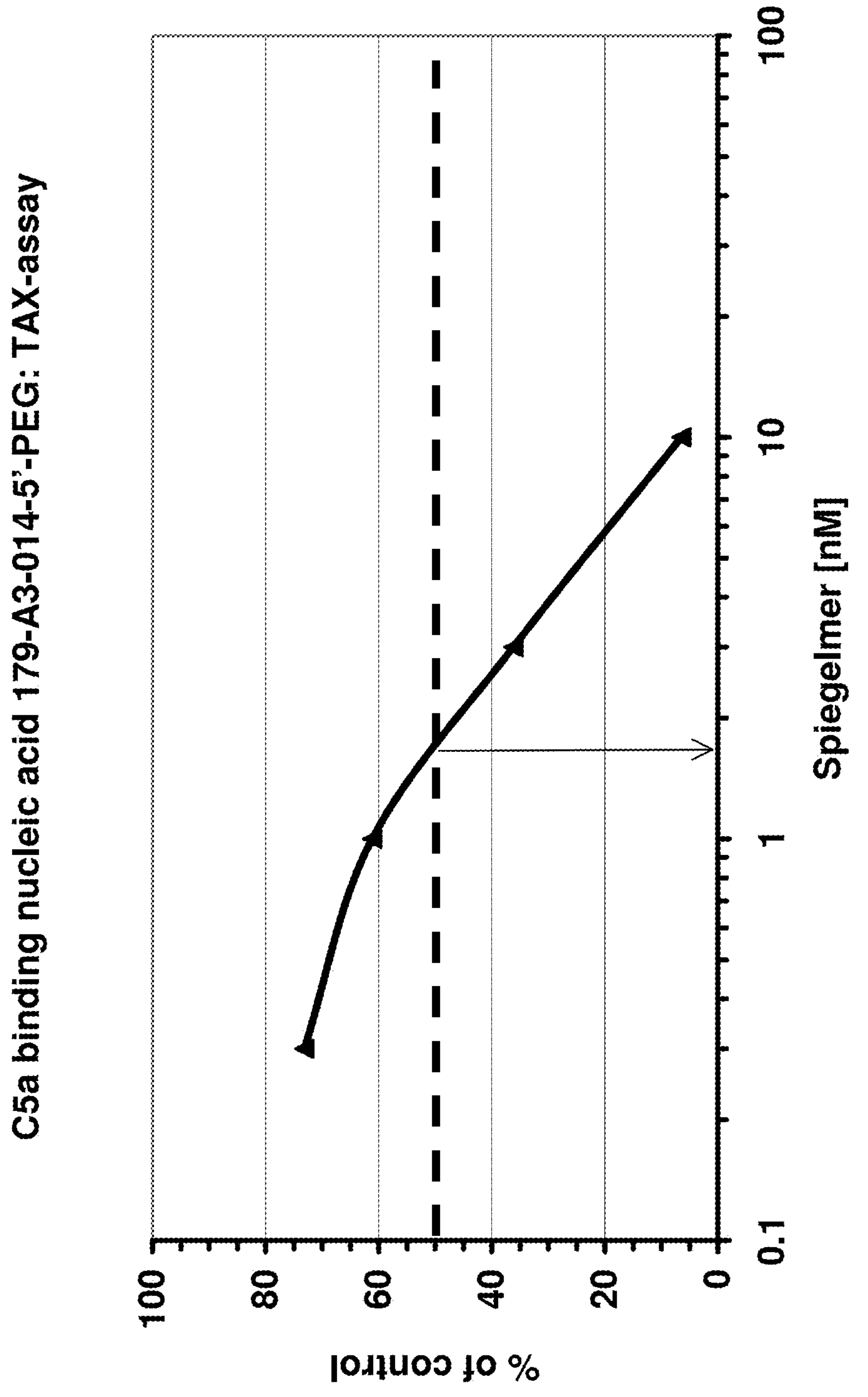
FIG. 14 shows the efficacy of Spiegelmer 179-A3-014-5'-PEG in a chemotaxis assay; cells were allowed to migrate towards 0.1 nM human C5a preincubated at 37° C. with various amounts of Spiegelmer 179-A3-014-5'-PEG, represented as percentage of control over concentration of Spiegelmer 179-A3-014-5'-PEG.

For the PEGylated derivative of C5a binding nucleic acid 179-A3-014, 179-A3-014-5'-PEG, an $IC_{50}$ of approx. 1.8 nM was determined in the TAX assay (FIG. 14).

1.3 Type C C5a Binding Nucleic Acids

As depicted in FIG. 6 and FIG. 7 all sequences of C5a binding nucleic acids of Type C comprise one central sequence stretch or box defining a potential C5a binding motif which is flanked by 5'- and 3'-terminal stretches that can hybridize to each other. However, such hybridization is not necessarily given in the molecule.

It is within the present invention that—with regard to Type C C5a binding nucleic acids—the terms '5'-terminal stretch' and 'first stretch', 'central sequence' and 'second stretch', and '3'-terminal stretch' and 'third stretch', respectively are used herein in a synonymous manner if not indicated to the contrary.

The nucleic acids were characterized on the aptamer level using direct and competitive pull-down binding assays with biotinylated human D-C5a in order to rank them with respect to their binding behaviour (Example 3). Selected sequences were synthesized as Spiegelmers (Example 2) and were tested using the natural configuration of human C5a (human L-C5a) in a cell culture in vitro $Ca^{2+}$-assay (Example 4) or a chemotaxis assay (Example 5).

The sequences of the defined boxes or stretches may be different between the C5a binding nucleic acids of Type C which influences the binding affinity to human C5a. Based on binding analysis of the different C5a binding nucleic acids summarized as Type C C5a binding nucleic acids, the central box and its nucleotide sequences as described in the following are individually and more preferably in their entirety essential for binding to human C5a:

The central box of all identified sequences of Type C C5a binding nucleic acids share the central sequence (SEQ ID NO: 59)

GUGUUUAYUYGCUUAAUAGGGR (Type C Formula-1).

Figure 15:
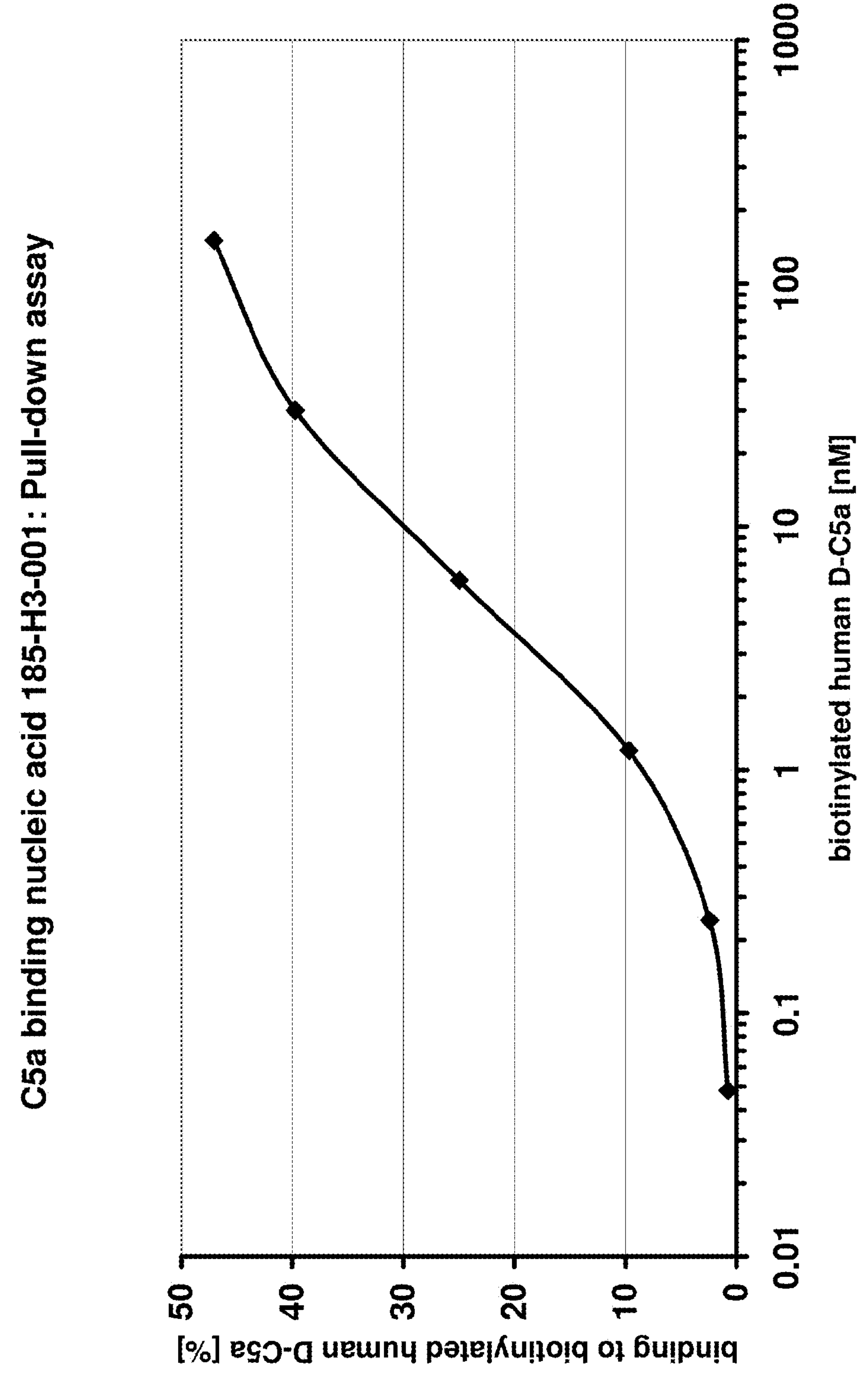

In order to determine the binding affinities of the different Type C C5a binding nucleic acids 185-H3-001, 185-D3, 185-B3, 185-B1, 184-F4, 185-A3, 185-B4, 185-G4, 185-H4 and 185-C3 to human C5a they were tested on the aptamer level using direct and competitive pull-down binding assays with biotinylated human D-C5a (Example 3). As reference the Type B C5a binding nucleic acid 179-A3-015 ($K_D$>7.2 nM) or Type C C5a binding nucleic acid 185-H3-001 ($K_D$=5 nM, $IC_{50}$=1-3 nM, FIG. 15) was used. Type C C5a binding nucleic acid 185-H3-001 has much better binding affinitity to human C5a than Type B C5a binding nucleic acid 179-A3-015. Type C C5a binding nucleic acids 185-D3, 185-B3 184-B4 and 185-G4 showed almost similar binding affinity to human C5a, whereby the binding affinity is similar to the binding affinity of Type B C5a binding nucleic acid 179-A3-015. Because Type C C5a binding nucleic acids 185-H3-001 showed the best binding affinity of Type C C5a binding nucleic acids, the preferred sequence of the central sequence for Type C C5a binding nucleic acids is (SEQ ID NO: 60)

GUGUUUACUUGCUUAAUAGGGG (Type C Formula-2).

This consensus sequence Type C Formula-2 for the central sequence stretch is additionally characteristic for 185-D3, 185-B3, 185-B4 and 185-G4. Because Type C C5a binding nucleic acids 185-D3, 185-B3, 185-B4 and 185-G4 have weaker binding affinity to human C5a than Type C C5a binding nucleic acid 185-H3-001, their different binding behaviour in comparison to Type C C5a binding nucleic acid 185-H3-001 has to be founded in the different sequences of the 5'- and 3'-terminal stretches (see below).

Figure 16:
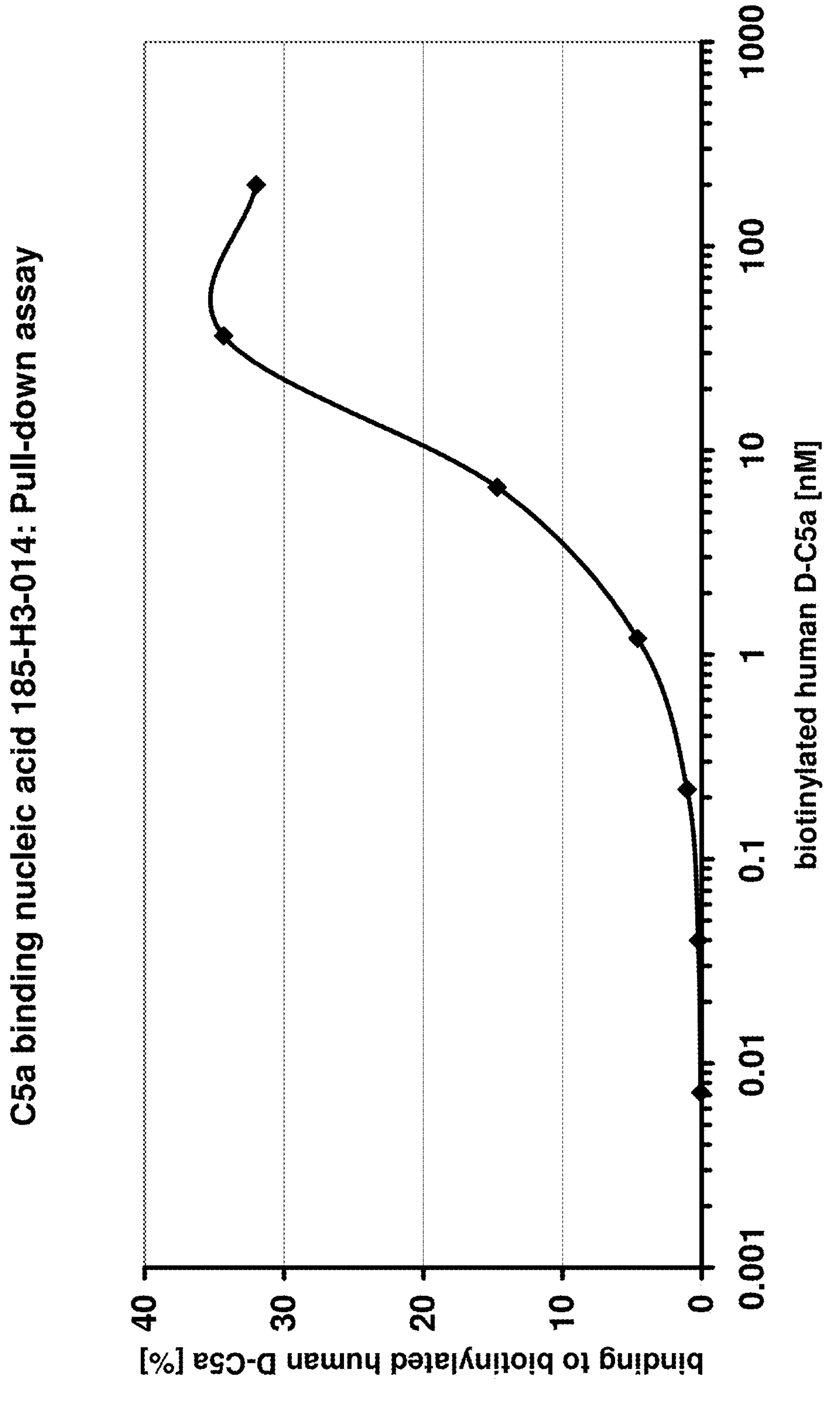

Seven or eight nucleotides of the 5'-terminal stretch of Type C C5a binding nucleic acids can hybridize to the respective seven or eight nucleotides of the 3'-terminal stretch to potentially form a terminal helix of seven or eight base-pairing nucleotides. Although the nucleotides are variable at several positions (see FIG. 6), the different nucleotides allow for hybridization of seven or eight nucleotides of the 5'- and 3'-terminal stretches each, whereby as shown for Type C C5a binding nucleic acids 185—H3-001, 185-D3, 185-B3, 185-B4 and 185-G4, that have the identical Box A, the sequence of the 5'- and 3'-terminal stretch has an influence of the binding behaviour to C5a (FIG. 6) Additionally, truncated derivatives of Type C C5a binding nucleic acids 185-H3-001 and 185-B4 (both sequences comprise the same central sequence) were analyzed in a competitive pull-down binding assay vs. the original molecule 185-H3-001 (FIG. 7). These experiments showed that a reduction of the seven terminal nucleotides (5'-end: GCUGGGC; 3'-end: GCCCAGC) of Type C C5a binding nucleic acid 185-H3-001 to five nucleotides could be only successfully done without reduction of binding affinity in the case of one pair of five terminal nucleotides (5'-end: GGGGC, 3'-end: GCCCC; 185-H3-014; pull-down assay see FIG. 16). However, the truncation to four terminal nucleotides (5' end: GGGC; 3' end: GCCC; 185-H3-003) or (5' end: GGGA; 3' end: UCCC; 185-B4-003) led to reduced binding affinity to C5a (FIG. 7).

However, combining the 5'- and 3'-terminal stretches of all tested Type C C5a binding nucleic acids the generic formula for the 5'-terminal stretch of Type C C5a binding nucleic acids is 5' $X_1X_2X_3$ KVG$X_4$M 3' (SEQ ID NOS 182 and 214-215, respectively, in order of appearance) (Type C Formula-3-5') and the generic formula for the 3'-terminal stretch Type C C5a binding nucleic acids is 5' D$X_5$YBH$X_6X_7X_8$ 3' (SEQ ID NOS 183 and 216-217, respectively, in order of appearance) (Type C Formula-3-3'), whereby $X_1$ is G or absent, $X_2$ is C or absent, $X_3$ is B or absent, $X_4$ is G, $X_5$ is C, $X_6$ is V or absent, $X_7$ is G or absent, $X_8$ is C or absent, or $X_1$ is G or absent, $X_2$ is C or absent, $X_3$ is B or absent, $X_4$ is absent, $X_5$ is absent, $X_6$ is V or absent, $X_7$ is G or absent, $X_8$ is C or absent, whereby preferably $X_1$ is G, $X_2$ is C, $X_3$ is B, $X_4$ is absent, $X_5$ is absent, $X_6$ is V, $X_7$ is G, $X_8$ is C.

The best binding affinities of Type C C5a binding nucleic acids comprising 5' and 3'-terminal stretches with four nucleotides, are shown for Type B C5a binding nucleic acid 185-H3-014 (5'-end: GGGGC, 3'-end: GCCCC).

For the PEGylated derivatives of C5a binding nucleic acids 185-H3-001 and 185-H3-014, 185-H3-001-5'-PEG and 185-H3-014-5'-PEG, $IC_{50}$'s of approx. 3.2 nM and 1.5 nM were determined in the TAX assay (FIG. 17).

1.4 Type D C5a Binding Nucleic Acids

As depicted in FIG. 8 all sequences of C5a binding nucleic acids of Type D comprise one central sequence stretch or box defining a potential C5a binding motif which is flanked by 5' and 3'-terminal stretches that can hybridize to each other. However, such hybridization is not necessarily given in the molecule.

It is within the present invention that—with regard to Type D C5a binding nucleic acids—the terms '5'-terminal stretch' and 'first stretch', 'central sequence' and 'second stretch', and '3'-terminal stretch' and "third stretch", respectively are used herein in a synonymous manner if not indicated to the contrary.

The nucleic acids were characterized on the aptamer level using direct and competitive pull-down binding assays with biotinylated human D-C5a in order to rank them with respect to their binding behaviour (Example 3). Selected sequences were synthesized as Spiegelmers (Example 2) and were tested using the natural configuration of human C5a (human L-C5a) in a chemotaxis assay (Example 5).

The sequences of the defined boxes or stretches may be different between the C5a binding nucleic acids of Type D which influences the binding affinity to human C5a. Based on binding analysis of the different C5a binding nucleic acids summarized as Type D C5a binding nucleic acids, the central box and its nucleotide sequences as described in the following are individually and more preferably in their entirety essential for binding to human C5a:

The central box of all identified sequences of Type D C5a binding nucleic acids share the central sequence (SEQ ID NO: 72)

GUUCGGACGUGGCAUGUUCCUUGAYAAACGGUUG (Type D Formula-1)

(FIG. 8). In order to determine the binding affinities of the different Type D C5a binding nucleic acids 182-E5, 182-C5 and 182-A8 to human C5a they were tested on the aptamer level using direct and competitive pull-down binding assays with biotinylated human D-C5a (Example 3). As reference the Type B C5a binding nucleic acid 179-A3-014 ($IC_{50}$=0.9 nM) was used. Type D C5a binding nucleic acids 182-E5 and 182-C5 have better binding affinitity to human C5a than Type B C5a binding nucleic acid 179-A3-014. Type D C5a binding nucleic acid 182-A8 ($K_D$=3.2 nM) showed in direct binding assay almost the same binding affinity as Type D C5a binding nucleic acids 182-E5 ($K_D$=2.4 nM, FIG. 18; IC50=1.2 nM, FIG. 19) and 182-C5 ($K_D$=2.2 nM).

Seven nucleotides of the 5'-terminal stretch of Type D C5a binding nucleic acids can hybridize to the respective seven nucleotides of the 3'-terminal stretch to potentially form a terminal helix of seven base-pairing nucleotides. Although the seven base-pairing nucleotides are variable at several positions (see FIG. 8), the different nucleotides allow for hybridization of seven nucleotides of the 5' and 3'-terminal stretches each.

1.5 Further Nucleic Acids Binding to C5a

Additionally, 7 other C5a binding nucleic acids were identified which cannot be described by a combination of nucleotide sequence elements as has been shown for Types A, B, C, and D of C5a binding nucleic acids. These sequences are listed in FIG. 9.

It is to be understood that any of the sequences shown in FIGS. 1 through 9 are nucleic acids according to the present invention, including those truncated forms thereof but also including those extended forms thereof under the proviso, however, that the thus truncated and extended, respectively, nucleic acid molecules are still capable of binding to the target.

EXAMPLE 2

Synthesis and derivatization of Aptamers and Spiegelmers

Small Scale Synthesis

Aptamers (D-RNA nucleic acids) and Spiegelmers (L-RNA nucleic acids) were produced by solid-phase synthesis with an ABI 394 synthesizer (Applied Biosystems, Foster City, Calif., USA) using 2'TBDMS RNA phosphoramidite chemistry (Damha and Ogilvie, 1993). rA(N-Bz)-, rC(Ac)-, rG(N-ibu)-, and rU-phosphoramidites in the D- and L-configuration were purchased from ChemGenes, Wilmington, Mass. Aptamers and Spiegelmers were purified by gel electrophoresis.

Large Scale Synthesis Plus Modification

Spiegelmers were produced by solid-phase synthesis with an ÄktaPilot100 synthesizer (Amersham Biosciences; General Electric Healthcare, Freiburg) using 2'TBDMS RNA phosphoramidite chemistry (Damha and Ogilvie, 1993). L-rA (N-Bz)-, L-rC(Ac)-, L-rG(N-ibu)-, and L-rU-phosphoramidites were purchased from ChemGenes, Wilmington, Mass. The 5'-amino-modifier was purchased from American International Chemicals Inc. (Framingham, Mass., USA). Synthesis of the unmodified or 5'-Amino-modified Spiegelmer was started on L-riboG, L-riboC, L-riboA or L-riboU modified CPG pore size 1000 Å (Link Technology, Glasgow, UK. For coupling (15 min per cycle), 0.3 M benzylthiotetrazole (CMS-Chemicals, Abingdon, UK) in acetonitrile, and 3.5 equivalents of the respective 0.1 M phosphoramidite solution in acetonitrile was used. An oxidation-capping cycle was used. Further standard solvents and reagents for oligonucleotide synthesis were purchased from Biosolve (Valkenswaard, NL). The Spiegelmer was synthesized DMT-ON; after deprotection, it was purified via preparative RP-HPLC (Wincott et al., 1995) using Source15RPC medium (Amersham). The 5'DMT-group was removed with 80% acetic acid (30 min at RT). Subsequently, aqueous 2 M NaOAc solution was added and the Spiegelmer was desalted by tangential-flow filtration using a 5 K regenerated cellulose membrane (Millipore, Bedford, Mass.).

PEGylation of Spiegelmers

In order to prolong the Spiegelmer's plasma residence time in vivo, Spiegelmers was covalently coupled to a 40 kDa polyethylene glycol (PEG) moiety at 5'-end.

5'-PEGylation of Spiegelmers

For PEGylation (for technical details of the method for PEGylation see European patent application EP 1 306 382), the purified 5'-amino modified Spiegelmer was dissolved in a mixture of $H_2O$ (2.5 ml), DMF (5 ml), and buffer A (5 ml; prepared by mixing citric acid.$H_2O$ [7 g], boric acid [3.54 g], phosphoric acid [2.26 ml], and 1 M NaOH [343 ml] and adding water to a final volume of 1 l; pH=8.4 was adjusted with 1 M HCl).

The pH of the Spiegelmer solution was brought to 8.4 with 1 M NaOH. Then, 40 kDa PEG-NHS ester (Jenkem Technology, Allen, Tex., USA) was added at 37° C. every 30 min in six portions of 0.25 equivalents until a maximal yield of 75 to 85% was reached. The pH of the reaction mixture was kept at 8-8.5 with 1 M NaOH during addition of the PEG-NHS ester.

The reaction mixture was blended with 4 ml urea solution (8 M), and 4 ml buffer B (0.1 M triethylammonium acetate in $H_2O$) and heated to 95° C. for 15 min. The PEGylated Spiegelmer was then purified by RP-HPLC with Source 15RPC medium (Amersham), using an acetonitrile gradient (buffer B; buffer C, 0.1 M triethylammonium acetate in acetonitrile). Excess PEG eluted at 5% buffer C, PEGylated Spiegelmer at 10-15% buffer C. Product fractions with a purity of >95% (as assessed by HPLC) were combined and mixed with 40 ml 3 M NaOAC. The PEGylated Spiegelmer was desalted by tangential-flow filtration (5 K regenerated cellulose membrane, Millipore, Bedford Mass.).

EXAMPLE 3

Determination of Binding Constants to C5a (Pull-Down Assay)

Direct Pull-Down Assay

The affinity of C5a binding nucleic acids were measured as aptamers (D-RNA nucleic acids) to biotinylated human D-C5a (SEQ.ID. 2) in a pull down assay format at 37° C. Aptamers were 5'-phosphate labeled by T4 polynucleotide kinase (Invitrogen, Karlsruhe, Germany) using [$\gamma$-$^{32}$P]-labeled ATP (Hartmann Analytic, Braunschweig, Germany). The specific radioactivity of labeled aptamers was 200,000-800,000 cpm/pmol. Aptamers were incubated after de- and renaturation at 20 pM concentration at 37° C. in selection buffer (20 mM Tris-HCl pH 7.4; 137 mM NaCl; 5 mM KCl; 1 mM $MgCl_2$; 1 mM $CaCl_2$; 0.1% [w/vol] Tween-20) together with varying amounts of biotinylated human D-C5a for 4-12 hours in order to reach equilibrium at low concentrations. Selection buffer was supplemented with 10 μg/ml human serum albumin (Sigma-Aldrich, Steinheim, Germany), and 10 μg/ml yeast RNA (Ambion, Austin, USA) in order to prevent adsorption of binding partners with surfaces of used plasticware or the immobilization matrix. The concentration range of biotinylated human D-C5a was set from 7 pM to 200 nM; total reaction volume was 1 ml. Biotinylated human D-C5a and complexes of aptamer and biotinylated human D-C5a were immobilized on 4 μl Streptavidin Ultralink Plus particles (Pierce Biotechnology, Rockford, USA) which had been pre-equilibrated with selection buffer and resuspended in a total volume of 12 μl. Particles were kept in suspension for 30 min at the respective temperature in a thermomixer. Immobilized radioactivity was quantitated in a scintillation counter after detaching the supernatant and appropriate washing. The percentage of binding was plotted against the concentration of biotinylated human D-C5a and dissociation constants were obtained by using software algorithms (GRAFIT; Erithacus Software; Surrey U.K.) assuming a 1:1 stoichiometry.

Competitive Pull-Down Assay

In order to compare different biotinylated human D-C5a binding aptamers, a competitive ranking assay was performed. For this purpose the most affine aptamer available was radioactively labeled (see above) and served as reference. After de- and renaturation it was incubated at 37° C. with biotinylated human D-C5a in 1 ml selection buffer at conditions that resulted in around 5-10% binding to the biotinylated human D-C5a after immobilization and washing on NeutrAvidin agarose or Streptavidin Ultralink Plus (both from Pierce) without competition. An excess of de- and renatured non-labeled D-RNA aptamer variants was added to different concentrations (e.g. 2, 10, and 50 nM) with the labeled reference aptamer to parallel binding reactions. The aptamers to be tested competed with the reference aptamer for target binding, thus decreasing the binding signal in dependence of their binding characteristics. The aptamer that was found most active in this assay could then serve as a new reference for comparative analysis of further aptamer variants.

EXAMPLE 4

Determination of Inhibitory Concentration in a $Ca^{++}$-Release Assay

U937 cells (DSMZ, Braunschweig, Germany) were cultivated at 37° C. and 5% $CO_2$ in RPMI 1640 medium with GlutaMAX (Invitrogen, Karlsruhe, Germany) which contained in addition 10% fetal calf serum, 50 units/ml penicillin and 50 μg/ml streptomycin. Two days before an experiment, cells are seeded in a new flask with a density of $0.2\times10^6$/ml ($6\times10^6$/30 ml) in standard medium to which dibutyryl-cAMP is added to result in a final concentration of 1 mM.

The Spiegelmers were incubated together with recombinant human C5a (SEQ.ID. 1) in Hanks balanced salt solution (HBSS), containing 1 mg/ml bovine serum albumin, 5 mM probenecid and 20 mM HEPES (HBSS+) for 15 to 60 min at 37° C. in a 0.2 ml low profile 96-tube plate ("stimulation solution").

For loading with the calcium indicator dye, cells were centrifuged at 300×g for 5 min, resuspended in 4 ml indicator dye solution (10 μM fluo-4 [Molecular Probes], 0.08% pluronic 127 [Molecular Probes] in HBSS+) and incubated for 60 min at 37° C. Thereafter, 11 ml HBSS+ were added and the cells were centrifuged as above, washed once with 15 ml HBSS+ and then resuspended in HBSS+ to give a cell density of $1.1\times10^6$/ml. 90 μl of this cell suspension were added to each well of a black 96-well plate.

Measurement of fluorescence signals was done at an excitation wavelength of 485 nm and an emission wavelength of 520 nm in a Fluostar Optima multidetection plate reader (BMG, Offenburg, Germany). For parallel measurement of several samples, wells of one (perpendicular) row of a 96-well plate were recorded together. First three readings with a time lag of 4 sec were done for determination of the base line. Then the recording was interrupted and the plate was moved from the instrument. Using a multi-channel pipette, 10 μl of the stimulation solution was added to the wells, then the plate was moved into the instrument again and the measurement was continued. In total, 20 recordings with time intervals of 4 seconds were performed.

For each well the difference between maximal fluorescence and base line value was determined and plotted against C5a concentration or, in the experiments on the inhibition of calcium release by Spiegelmers, against concentration of Spiegelmer.

Determination of Half-Maximal Effective Concentration ($EC_{50}$) for Human C5a

After stimulation of U937 cells with various C5a concentrations and plotting the difference between the maximal and the baseline signals, a dose-response curve for human C5a was obtained, indicating a half effective concentration ($EC_{50}$) of about 1 nM. This concentration was used for the further experiments on inhibition of $Ca^{++}$-release by Spiegelmers.

EXAMPLE 5

Determination of Inhibitory Concentration in a Chemotaxis Assay

U937 cells grown and differentiated as described above were centrifuged, washed once in HBH (HBSS, containing 1 mg/ml bovine serum albumin and 20 mM HEPES) and resuspended at $3\times10^6$ cells/ml. 100 μl of this suspension were added to Transwell inserts with 5 μm pores (Costar Corning, #3421; NY, USA). In the lower compartments recmbinant human C5a (SEQ.ID. 1) was preincubated together with Spiegelmers in various concentrations in 600 μl HBH at 37° C. for 20 to 30 min prior to addition of cells. Cells were allowed to migrate at 37° C. for 3 hours. Thereafter the inserts were removed and 60 μl of 440 μM resazurin (Sigma, Deisenhofen, Germany) in phosphate buffered saline was added to the lower compartments. After incubation at 37° C. for 2.5 hours, fluorescence was measured at an excitation wavelength of 544 nm and an emission wavelength of 590 nm in a Fluostar Optima multidetection plate reader (BMG, Offenburg, Germany).

Fluorescence values are corrected for background fluorescence (no cells in well). Then the difference between experimental conditions with and without C5a is calculated. These results can be depicted in a histogram. Alternatively or in addition to this, the value for the sample without Spiegelmer (C5a only) is set 100% and the values for the samples with Spiegelmer are calculated as percent of this. For a dose-response curve the percent-values are plotted against Spiegelmer concentration and the IC50-value (concentration of Spiegelmer at which 50% of the activity without Spiegelmer is present) is determined graphically from the resulting curve.

Determination of Half-Maximal Effective Concentration ($EC_{50}$) for Human C5a

After 3 hours migration of U937 cells towards various human C5a concentrations, a dose-response curve for human C5a was obtained, indicating a maximal effective concentration of about 1 nM and reduced activation at higher concentrations. For the further experiments on inhibition of chemotaxis by Spiegelmers a C5a concentration of 0.1 nM was used.

EXAMPLE 6

Determination of Binding Constants to C5 (Filter Binding Assay)

The affinity of Spiegelmers to complement component 5 from human blood (human L-C5; Sigma Aldrich, Taufkirchen, Germany (Cat No. C3160); consisting of the human C5 alpha chain see SEQ.ID. 171, human C5 beta chain see SEQ.ID. 172) was measured in a filter binding assay format at 37° C. Spiegelmers were synthesized with two additional D-guanosine moieties at the 5' end allowing for labeling by T4 polynucleotide kinase with [$\gamma$-$^{32}$P]-ATP. The specific radioactivity of labeled Spiegelmers was 300,000-500,000 cpm/pmol. Spiegelmers were incubated after heat de- and renaturation at 30 pM concentration at 37° C. in binding buffer (20 mM Tris-HCl, pH 7.4; 150 mM NaCl; 5 mM KCl; 1 mM $MgCl_2$; 1 mM $CaCl_2$; 0.001% [w/vol] Tween-20) together with varying amounts of C5 for 4-6 hours. Binding buffer was supplemented with 10 μg/ml human serum albumin in order to prevent adsorption of binding partners with surfaces of the plasticware used. The concentration range of C5 was set from 7 pM to 100 nM; the total reaction volume was 0.4 ml. Nitrocellulose (NC) filters with 0.22 μm pore size and 10 mm diameter (Millipore, Schwalbach, Germany) were soaked for 5 min in $H_2O$ and placed on a vacuum manifold (Mallinckrodt Baker, Germany). Before transfer of the binding reactions to the NC filters a vacuum corresponding to −5 inches of Hg was applied on the filter via the vacuum manifold. The binding reactions passed through the filters and C5 was retained on the filter—together with labeled Spiegelmer, if the latter was in complex with C5. The percentage of bound Spiegelmer was measured in a scintillation counter after appropriate washing with buffer without BSA. The percentage of filter-bound Spiegelmer was plotted against the concentration of C5 and dissociation constants were obtained by using the software (GRAFIT; Erithacus Software; Surrey U.K.) assuming a 1:1 stoichiometry.

The Type A C5a binding nucleic acids 172-D7-000 (SEQ. ID. 3) and 172-D7-013 (SEQ ID NOS 14 and 225), the Type B C5a binding nucleic acids 179-A3-014 (SEQ.ID. 36) and 179-A3-015 (SEQ.ID. 38), the Type C C5a binding nucleic acids 185-H3-001 (SEQ.ID. 49), 185-H3-002 (SEQ.ID. 63), 185-H3-014 (SEQ.ID. 65) and 185-H3-003 (SEQ.ID. 67) and Type D C5a binding nucleic acids 182-E5 (SEQ. ID. 69) and 182-C5 (SEQ. ID. 70) were synthesized as spiegelmers with two D-guanosine moieties at the 5' end allowing for labelling by T4 polynucleotide kinase with [$\gamma$-$^{32}$P]-ATP. All such modified spiegelmers (SEQ ID NOS 157, 158 and 245, 159-166, and 167 and 246) showed biniding affinity to human C5 comparable to their respective binding behaviour to human C5a (Individual binding affinities of the corresponding aptamer sequences to synthetic human D-C5a see FIGS. 1-8). The data for C5a binding nucleic acids 172-D7-013, 179-A3-014 and 185-H3-014 are shown in FIG. 20.

Besides the fact that the entire C5 molecule is bound by these molecules, this experiment shows that biological C5 from human serum and therefore with its natural glycosylation is also bound by the Spiegelmers described here.

EXAMPLE 7

Proof of Concept: Activity of a Selected C5a Spiegelmer In Vivo

To test the ability of Spiegelmer 185-H3-014-5'-PEG to block C5a action in vivo, the known property of human C5a to induce neutropenia in gerbils (Sumichika et al., 2002) was utilized as a model for septic shock.

Method

Anesthetized female Mongolian gerbils (Charles River, Germany, 7-8 weeks old, n=7 per group) received a single i.v. injection of anti-C5a Spiegelmer 185-H3-014-5'-PEG (2 mg/kg or 10 mg/kg oligonucleotide in 5% glucose) or vehicle (5% glucose). A PEGylated Spiegelmer of the same base composition but the reverse sequence, that does not bind to C5a was used to differentiate C5a-binding related effects from unspecific interference with the model by Spiegelmers in general. The reverse Spiegelmer 185-H3-014-REVERSE-5'-PEG was also dosed at 2 mg/kg or 10 mg/kg oligonucleotide in 5% glucose in additional control groups. After 8 to 9 min, blood was collected via intracardiac puncture from the animals. This was followed by an i.v. bolus injection of 100 μg/kg human recombinant C5a (Sigma, Deisenhofen, Germany Cat No. #C5788). Blood was subsequently collected 1, 3 and 5 min after the C5a injection. The samples were immediately transferred into tubes containing EDTA as anticoagulant.

Blood smears were prepared from the blood samples and stained with May Grünwald-Giemsa staining 100 white blood cells on each blood smear were counted and differential cell numbers determined for neutrophils, eosinophils, basophils, lymphocytes and monocytes. For each animal the percentage of neutrophils was determined for the time points 1 and 5 min and expressed as percentage of the neutrophil count for time point 0.

Results

Injection of C5a leads to a rapid reduction of neutrophils in the blood: one min after injection, the neutrophil count was reduced to ca. 30% of the value before injection. Three minutes later, the value is already higher again (ca. 55%) and rises to ca. 70% 5 min post injection of C5a, which indicates that the process is reversible. These in vivo findings are quite in line with the data published by Sumichika et al., who reported a reduction to ca. 20% in a very similar experiment. This decrease in neutrophil number (neutropenia) is significantly attenuated by application of Spiegelmer 185-H3-014-5'-PEG (10 mg/kg oligonucleotide) prior to injection of C5a as depicted in FIG. 21 at 1 min and 3 min post C5a application. The dose group of 2 mg/kg did not lead to an inhibition of neutropenia. This may be due to the fast kinetics of the C5a-mediated effect. The reverse Spiegelmer 185-H3-014-REVERSE-5'-PEG did not lead to a reduction of the human recombinant C5a-induced neutropenia in both tested concentrations.

EXAMPLE 8

Binding of C5a Binding Spiegelmers to Rhesus Monkey C5a

Method

The sequence of rhesus monkey (*Macaca mulatta*) C5a was deduced from the predicted sequence for complement component 5 (accession XM_001095750). The sequence presumably coding for C5a was amplified from rhesus monkey total liver RNA (BioCat) by RT-PCR using the primers 5'-ATGCTACAAGAGAAGATAGAAG (SEQ ID NO: 184) (C5a-Primer-I) and 5'-CTAGCATGCTTACCTTCCCAATTGC (SEQ ID NO: 185) (C5a-Primer-II) and cloned into the pQE30Xa vector (Qiagen, Hilden, Germany).

The resulting protein (Pubmed accession No. XP_001095750, SEQ.ID. 186) is 85% (63 of 74 amino acids) identical to human C5a (SEQ.ID. 1).

The His6-tagged (SEQ ID NO: 247) protein was expressed in *E. coli* BL21 and purified with nickel affinity chromatography (HIS-Select, Sigma, Deisenhofen, Germany) in buffers containing 8 M urea. The protein was eluted with 250 mM imidazole and stored at −20° C. Prior to use in chemotaxis assays (see example 5) the protein was diluted (1:10) in renaturation buffer (50 mM Tris/HCl, pH 8.0, 0.005% Tween 20, 2 mM reduced glutathione, 0.2 mM oxidized glutathione) and incubated for at least 10 min at room temperature before further dilution in HBH.

Chemotaxis assays were performed as described in example 5 using the purified monkey C5a (His6-macC5a ('His6' disclosed as SEQ ID NO: 247)) or recombinant human C5a. The final concentration of His6-macC5a ('His6' disclosed as SEQ ID NO: 247) was approximately 0.8 nM according to protein determination with the BCA method and gave a chemotactic response of U937 cells similar to 0.1 nM human C5a. The tested Spiegelmers were applied at 100 nM.

Result

Whereas the Spiegelmers 185-H3-014-5'PEG and 185-H3-001 could not inhibit the action of His6macC5a ('His6' disclosed as SEQ ID NO: 247), Spiegelmer 179-A3-014-5'PEG completely blocked the chemotaxis of U937 cells induced by His6macC5a ('His6' disclosed as SEQ ID NO: 247) (FIG. 22).

References

The complete bibliographic data of the documents recited herein the disclosure of which is incorporated by reference is, if not indicated to the contrary, as follows.

Altschul S F, Gish W, Miller W, Myers E W, Lipman D J (1990), Basic local alignment search tool. J Mol. Biol. 215(3):403-10.

Altschul S F, Madden T L, Schaffer A A, Zhang J, Zhang Z, Miller W, Lipman D J (1997). Gapped BLAST and PSI-BLAST: a new generation of protein database search programs. Nucleic Acids Res. 25(17):3389-402.

Aurup H et al. (1994). Nucleic Acids Res 22:20

Bergh K, Iversen O J, Lysvand H. 1993. Surprisingly high levels of anaphylatoxin C5a des Arg are extractable from psoriatic scales. Arch Dermatol Res 285(3):131-134.

Bonifati D M, Kishore U. 2007 Role of complement in neurodegeneration and neuroinflammation. Mol Immunol 44(5): 999-1010.

Cummins L L et al. (1995). Nucleic Acids Res 23:2019

Damha M J and Ogilvie K K, Methods in Molecular Biology, Vol. 20 Protocols for oligonucleotides and analogs, ed. S. Agrawal, p. 81-114, Humana Press Inc. 1993

Durand M, Chevrie K, Chassignol M, Thuong N T, and Maurizot J C (1990), Circular dichroism studies of an oligodeoxyribonucleotide containing a hairpin loop made of a hexaethylene glycol chain: conformation and stability. Nucleic. Acids Res 18: 6353-6359.

Eaton B E et al. (1995). Chem Biol 2:633

Eaton B E, Gold L, Hicke B J, Janjic N, Jucker F M, Sebosta D P, Tarasow T M, Willis M C, Zichi D A (1997). Bioorg Med Chem 5:1087

Fernandez H N, Hugh T E. 1978. Primary structural analysis of the polypeptide portion of human C5a anaphylatoxin. Polypeptide sequence determination and assignment of the oligosaccharide attachment site in C5a. J Biol Chem 253 (19):6955-6964.

Green L S et al. (1995). Chem Biol 2:683

Heller T, Hennecke M, Baumann U, Gessner J E, zu Vilsendorf A M, Baensch M, Boulay F, Kola A, Klos A, Bautsch W, Kohl J. 1999. Selection of a C5a receptor antagonist from phage libraries attenuating the inflammatory response in immune complex disease and ischemia/reperfusion injury. J Immunol 163(2):985-994.

Hillmen P, Muus P, Duhrsen U, Risitano A M, Schubert J, Luzzatto L, Schrezenmeier H, Szer J, Brodsky R A, Hill A, Socie G, Bessler M, Rollins S A, Bell L, Rother R P, Young N S (2007). Effect of the complement inhibitor eculizumab on thromboembolism in patients with paroxysmal nocturnal hemoglobinuria. Blood, August 2007, PMID: 17702897

Huber-Lang M S, Sarma J V, McGuire S R, Lu K T, Guo R F, Padgaonkar V A, Younkin E M, Laudes I J, Riedemann N C, Younger J G, Ward P A. 2001. Protective effects of anti-C5a peptide antibodies in experimental sepsis. Faseb J 15(3):568-570.

Kawasaki A M et al. (1993). J Med Chem 36:831

Kirschfink M. 1997. Controlling the complement system in inflammation. Immunopharmacology 38(1-2):51-62.

Kohl J. 2001. Anaphylatoxins and infectious and non-infectious inflammatory diseases. Mol Immunol 38(2-3):175-187.

Kusser W (2000). J Biotechnol 74:27-38

Lesnik E A et al. (1993). Biochemistry 32:7832

Lewis A G, Kohl G, Ma Q, Devarajan P, Kohl J. 2008 Pharmacological targeting of C5a receptors during organ preservation improves kidney graft survival. Clin Exp Immunol 153(1): 117-126.

Lewis F D, Liu X, Wu Y, Miller S E, Wasielewski M R, Letsinger R L, Sanishvili R, Joachimiak A, Tereshko V and Egli M (1999). Structure and photoinduced eletron transfer in exceptionally stable synthetic DNA hairpins with stilbenediether linkers. JACS 121:9905-9906.

Ma M Y, Reid L S, Climie S C, Lin W C, Kuperman R, Sumner-Smith M, Barnett R W (1993a). Design and synthesis of RNA miniduplexes via a synthetic linker approach. Biochemistry 32(7):1751-1758.

Makrides S C. 1998. Therapeutic inhibition of the complement system. Pharmacol Rev 50(1):59-87.

Manderson A P, Botto M, Walport M J. 2004. The role of complement in the development of systemic lupus erythematosus Annu Rev Immunol 22: 431-456

McGinnis S, Madden T L (2004). BLAST: at the core of a powerful and diverse set of sequence analysis tools. Nucleic Acids Res. 32(Web Server issue):W20-5.

Miller L E et al. (1993). J Physiol 469:213

Muller-Ladner U, Jones J L, Wetsel R A, Gay S, Raine C S, Barnum S R. 1996. Enhanced expression of chemotactic receptors in multiple sclerosis lesions. J Neurol Sci 144(1-2):135-141.

Needleman & Wunsch (1970), A general method applicable to the search for similarities in the amino acid sequence of two proteins. J Mol. Biol. 48(3):443-53.

Nozaki M, Raisler B J, Sakurai E, Sarma J V, Barnum S R, Lambris J D, Chen Y, Zhang K, Ambati B K, Baffi J Z, Ambati J. 2006. Drusen complement components C3a and C5a promote choroidal neovascularization. Proc Natl Acad Sci USA 103(7): 2328-2333

Pearson & Lipman (1988), Improved tools for biological sequence comparison. Proc. Nat'l. Acad. Sci. USA 85: 2444

Piccolo M T, Wang Y, Sannomiya P, Piccolo N S, Piccolo M S, Hugh T E, Ward P A, Till G O. 1999. Chemotactic mediator requirements in lung injury following skin burns in rats. Exp Mol Pathol 66(3):220-226.

Pils W and Micura R (2000), Flexible non-nucleotide linkers as loop replacements in short double helical RNAs. Nucleic Acids Res. 28(9):1859-63.

Ricklin D, Lambris J D. 2007 Complement-targeted therapeutics. Nat Biotechnol 25(11): 1265-1275

Riley R D, Sato H, Zhao Z Q, Thourani V H, Jordan J E, Fernandez A X, Ma X L, Hite D R, Rigel D F, Pellas T C, Peppard J, Bill K A, Lappe R W, Vinten-Johansen J. 2000. Recombinant human complement C5a receptor antagonist reduces infarct size after surgical revascularization. J Thorac Cardiovasc Surg 120(2):350-358.

Sim R B, Laich A. 2000. Serine proteases of the complement system. Biochem Soc Trans 28(5):545-550.

Smith & Waterman (1981), Adv. Appl. Math. 2: 482

Sumichika et al (2002) J. Biol. Chem. 277: 49403-49407

Thomson J B, Tuschl T, and Eckstein F (1993), Activity of hammerhead ribozymes containing normucleotidic linkers. Nucleic. Acids Res 21: 5600-5603.

Venkatesan N et al. (2003). Curr Med Chem 10:1973

Walport M J. 2001a. Complement. First of two parts. N Engl J Med 344(14):1058-1066.

Walport M J. 2001b. Complement. Second of two parts. N Engl J Med 344(15):1140-1144.

Wang Y. 2006. Complementary therapies for inflammation. Nat Biotechnol 24(10): 1224-1226

Wincott F, DiRenzo A, Shaffer C, Grimm S, Tracz D, Workman C, Sweedler D, Gonzalez C, Scaringe S, and Usman N (1995). Synthesis, deprotection, analysis and purification of RNA and ribosomes. *Nucleic Acids Res.* 23: 2677-2684.

Woodruff T M, Arumugam T V, Shiels I A, Reid R C, Fairlie D P, Taylor S M. 2003. A potent human C5a receptor antagonist protects against disease pathology in a rat model of inflammatory bowel disease. J Immunol 171(10):5514-5520.

Woodruff T M, Strachan A J, Dryburgh N, Shiels I A, Reid R C, Fairlie D P, Taylor S M. 2002. Antiarthritic activity of an orally active C5a receptor antagonist against antigen-induced monarticular arthritis in the rat. Arthritis Rheum 46(9):2476-2485.

Yao Y M, Redl H, Bahrami S, Schlag G. 1998. The inflammatory basis of trauma/shock-associated multiple organ failure. Inflamm Res 47(5): 201-210.

Zuiderweg E R, Nettesheim D G, Mollison K W, Carter G W. 1989. Tertiary structure of human complement component C5a in solution from nuclear magnetic resonance data. Biochemistry 28(1):172-185.

The features of the present invention disclosed in the specification, the claims, the sequence listing and/or the drawings may both separately and in any combination thereof be material for realizing the invention in various forms thereof.

The invention claimed is:

1. A nucleic acid that binds C5a comprising in 5'→3' direction, a first stretch, a second stretch Box A, a third stretch Box L, a fourth stretch Box B and a fifth stretch, wherein the first stretch and the fifth stretch optionally hybridize to form a double-stranded structure, the first stretch comprises four to eight nucleotides, the second stretch Box A comprises ASACGCCGVRYAGGWC (SEQ ID NO:30), the third stretch Box L comprises four to eleven nucleotides, the fourth stretch Box B comprises GWAGAAUSG (SEQ ID NO:32) and, the fifth stretch comprises four to eight nucleotides.

2. The nucleic acid according to claim 1, wherein the double-stranded structure consists of four to eight basepairs.

3. The nucleic acid according to claim 1, wherein the first stretch and the second stretch Box A are separated by one to four nucleotides.

4. The nucleic acid according to claim 1, wherein the first stretch and the second stretch Box A are separated by one nucleotide.

5. The nucleic acid according to claim 1, wherein the fourth stretch Box B and the fifth stretch are separated by one nucleotide.

6. The nucleic acid according to claim 1, wherein the first stretch and the second stretch Box A are separated by one nucleotide and the fourth stretch Box B and the fifth stretch are separated by one nucleotide and the one nucleotide separating the first stretch and the second stretch Box A, and the one nucleotide separating the fourth stretch Box B and the fifth stretch do not hybridize to each other.

7. The nucleic acid molecule according to claim 1, wherein the first stretch of nucleotides comprises a nucleotide sequence of 5' $X_1X_2SBBX_3X_4X_5$ 3' (SEQ ID NO:197) and the fifth stretch of nucleotides comprises a nucleotide sequence of 5' $X_6X_7X_8VVSX_9X_{10}$ 3' (SEQ ID NO;204), wherein $X_1$ is G or absent,
$X_2$ is U or absent,
$X_3$ is B,
$X_4$ is absent,
$X_5$ is absent,
$X_6$ is absent,
$X_7$ is absent,
$X_8$ is N,
$X_9$ is A or absent, and
$X_{10}$ is C or absent.

8. The nucleic acid molecule according to claim 1, wherein the first stretch of nucleotides comprises a nucleotide sequence of 5' $X_1X_2SSBX_3X_4X_5$ 3' (SEQ ID NO:188) and the fifth stretch of nucleotides comprises a nucleotide sequence of 5' $X_6X_7X_8VSSX_9X_{10}$ 3' (SEQ, ID NO:189), wherein $X_1$ is G or absent,
$X_2$ is U or absent,
$X_3$ is S,
$X_4$ is absent,
$X_5$ is absent,
$X_6$ is absent,
$X_7$ is absent,
$X_8$ is S,
$X_9$ is A or absent, and
$X_{10}$ is C or absent.

9. The nucleic acid molecule according to claim 1, wherein the first stretch of nucleotides comprises a nucleotide sequence of 5' GCUG 3' and the fifth stretch of nucleotides comprises a nucleotide sequence of 5' CAGC 3' or wherein the first stretch of nucleotides comprises a nucleotide sequence of 5' CGCC 3' and the fifth stretch of nucleotides comprises a nucleotide sequence of 5' GGCG 3' or wherein the first stretch of nucleotides comprises a nucleotide sequence of 5' CCGG 3' and the fifth stretch of nucleotides comprises a nucleotide sequence of 5' CCGG 3'.

10. The nucleic acid molecule according to claim 1, wherein the first stretch of nucleotides comprises a nucleotide sequence of 5' $X_1$ $X_2$GCC$X_3X_4X_5$ 3' (SEQ ID NO:181) and the fifth stretch of nucleotides comprises a nucleotide sequence of 5' $X_6X_7X_8$AGC$X_9X_{10}$ 3' (SEQ ID NO:211), wherein $X_1$ is G or absent,
$X_2$ is U or absent,
$X_3$ is G,
$X_4$ is C,
$X_5$ is C,
$X_6$ is G,
$X_7$ is G,
$X_8$ is C,
$X_9$ is A or absent, and
$X_{10}$ is C or absent.

11. The nucleic acid according to claim 1, wherein the second nucleotide at the 5'-end of the second stretch Box A is C and the penultimate nucleotide at the 3'-end of the fourth stretch Box B is G or the second nucleotide at the 5'-end of the second stretch Box A is G and the penultimate nucleotide at the 3'-end of the fourth stretch Box B is C.

12. The nucleic, acid according to claim 1, wherein the penultimate nucleotide at the 3'-end of the second stretch Box A is A and the second nucleotide at the 5'-end of the fourth stretch Box B is U or the penultimate nucleotide at the 3'-end of the second stretch Box A is U and the second nucleotide at the 5'-end of the fourth stretch Box B is A.

13. The nucleic acid according, to claim 1, wherein the second stretch Box A comprises a nucleotide sequence of ASACGCCGMRYAGGWC (SEQ ID NO:31) or a nucleotide sequence of ACACGCCGCGUAGGAC (SEQ ID NO:212).

14. The nucleic acid according to claim 1, wherein the fourth stretch Box B comprises a nucleotide sequence of GUAGAAUGG (SEQ ID NO:213).

15. The nucleic acid according to claim 1, wherein the third stretch Box L comprises a first substretch and a second substretch and the first substretch and the second substretch hybridize to form a double-stranded structure.

16. The nucleic acid according to claim 15, wherein the sequence of the first and the second substretch is independently CC or GG, under the proviso that the sequence of the nucleotides is different for the first and the second substretch.

17. The nucleic acid according to claim 15, wherein the first substretch and the second substretch are separated within the third stretch by a separating stretch comprising a spacer or a nucleotide sequence of AAU.

18. The nucleic acid according to claim 17, wherein within the separating stretch a minimum of two nucleotides is replaced by a spacer.

19. The nucleic acid according to claim 17. wherein the separating stretch consists of a spacer.

20. The nucleic acid according to claim 19, wherein the spacer is a hydrophilic spacer.

21. The nucleic acid according, to claim 20, wherein the hydrophilic spacer consists of polyethylene moieties.

22. The nucleic acid according to claim 1, wherein the nucleic acid comprises a nucleic acid sequence according to SEQ NOs:21 to 23, 33, 34, 36, 37 and 232, 40, 46, 47 or 168.

23. nucleic acid according to claim 1, wherein the C5a is human.

24. The nucleic acid according to claim 1, wherein the C5a has an amino acid sequence according to SEQ ID NO:1.

25. The nucleic acid according to claim 1, wherein the nucleic acid comprises a modification group, wherein the modification group controls residence time in an animal or human body.

26. The nucleic acid according to claim 25, wherein the modification group is a HES moiety, a PEG moiety or a biodegradable modification.

27. The nucleic acid according to claim 26. wherein the PEG moiety comprises a straight or branched PEG comprising a molecular weight from about 20,000 to 120,000 Da.

28. The nucleic acid according to claim 26, wherein the HES moiety has a molecular weight from about 10,000 to 200,000 Da.

29. The nucleic acid according to claim 25 wherein the modification group is coupled to the nucleic acid via a non-degradable linker or a biodegradable linker.

30. The nucleic acid according to claim 25, wherein the modification group is coupled to the nucleic, acid 5'-terminal nucleotide the 3'-terminal nucleotide of the nucleic acid, to both the 5'-terminal nucleotide and the 3'-nucleotide of the nucleic, acid; or to a nucleotide of the nucleic acid between the 5'-tertninal nucleotide of the nucleic acid and the 3'-terminal nucleotide of the nucleic acid.

31. The nucleic acid according to claim 1 comprising L-nucleotides.

32. The nucleic acid according to claim 1, wherein the nucleic acid is an L-nucleic acid.

33. The nucleic acid according to claim 1, wherein the nucleic acid comprises at least one moiety which binds C5a, wherein said moiety comprises L-nucleotides.

34. A pharmaceutical composition comprising a nucleic acid according to claim 1 and a pharmaceutically acceptable excipient, a pharmaceutically acceptable carrier or a pharmaceutically active agent.

35. The pharmaceutical composition according to claim 34, wherein the pharmaceutical composition comprises a pharmaceutically acceptable carrier.

36. The composition. according to claim 34, wherein the composition is a human medicine or a veterinary medicine.

37. A storage solution and/or a transport solution comprising the composition according to claim 34 and an organ.

38. A complex comprising the nucleic acid according to claim 1, and C5 and/or C5a.

39. The complex according to claim 38, wherein C5a is selected from the group consisting of human C5a, monkey C5a, horse C5a, rabbit C5a, bovine C5a, canine C5a and porcine C5a.

40. The complex according to claim 38, wherein C5 is selected from the group consisting of human C5, monkey C5,horse C5, rabbit C5,bovine C5, canine C5 and porcine C5,

41. A method for the screening of an antagonist or an agonist of C5 or C5a comprising the following steps:

providing a candidate antagonist and/or a candidate agonist of C5 or C5a, providing the nucleic acid according to claim 1, providing a test system which provides a signal in the presence of an antagonist and/or an agonist of C5 or C5a, and determining whether the candidate antagonist is an antagonist of C5 or C5a and/or whether the candidate agonist is an agonist of C5 or C5a.

42. The method according to claim 41, wherein the C5 or C5a is human.

43. The method according to claim 41, wherein the C5a is human C5a, monkey C5a, horse C5a, rabbit C5a, bovine C5a, canine C5a or porcine C5a.

44. The method according to claim 41, wherein the C5 is human C5, monkey C5,horse C5, rabbit C5,bovine C5,canine C5 or porcine C5.

45. A method for the screening of an agonist and/or an antagonist of C5 or C5a comprising the following steps:

providing a C5 or C5a immobilised to a phase, providing a nucleic acid according to claim 1, which optionally is labelled, adding a candidate agonist and/or a chemokine antagonist of C5 or C5a, and determining whether the candidate agonist is an agonist and/or whether the candidate antagonist is an antagonist of C5 or C5a.

46. The method according to claim 45, characterised in that the determining is carried out by assessing whether the nucleic acid is replaced by the candidate agonist or by a candidate antagonist of C5 or C5a.

47. The method according to claim 45, wherein the C5 or C5a is human.

48. The method according to claim 45, the C5a is human C5a, monkey C5a, horse C5a, rabbit C5a, bovine C5a, canine C5a or porcine C5a.

49. The method according to claim 45, the C5 is C5, monkey C5, horse C5, rabbit C5, bovine C5, canine C5 or porcine C5.

50. A kit for the detection of C5 and/or C5a comprising the nucleic acid according to claim 1 and reagents for determining presence of C5 or C5a.

51. The kit according to claim 50, wherein the C5 and/or C5a is human.

52. An antagonist of C5 or C5a consisting of the nucleic acid of claim 1.

53. The antagonist of C5 or C5a according to claim 52, wherein said C5 or C5a is human,

54. The antagonist according to claim 52, wherein the C5a is human C5a, monkey C5a, horse C5a, rabbit C5a, bovine C5a, canine C5a or porcine C5a.

55. The antagonist according to claim 52, wherein the C5 is human C5, monkey C5, horse C5, rabbit C5, bovine C5, canine C5 or porcine C5.

56. A method for the detection of the nucleic acid according to claim 1 in a sample, wherein the method composes the steps of:

a) providing the sample containing the nucleic acid according to claim 1;

b) providing a capture probe, wherein the capture probe is at least partially complementary to a first part of the nucleic acid according to claim 1, and a detection probe, wherein the detection probe is at least partially complementary to a second part of the nucleic acid according to claim 1;

c) allowing the capture probe and the detection probe to react either simultaneously or in any order sequentially with the nucleic acid in said sample; and d) optionally detecting whether or not the capture probe is hybridized to the nucleic acid of claim 1; or e) detecting the complex formed in step c) consisting of the nucleic acid according to claim 1 and the capture probe and the detection probe.

57. The method according, to claim 56, wherein the detection probe comprises a detection label and/or wherein the capture probe is immobilized on a support.

58. The method according to claim 56, wherein detection probe not part of the complex is removed from the reaction so that in step e) only a detection probe which is part of the complex is detected.

59. The method according to claim 56, wherein step e) comprises the step of comparing the signal generated by the detection label when the capture probe and the detection probe are hybridized in the presence of the nucleic acid according to claim 1, and the signal generated in the absence of said nucleic acid of claim 1.

60. The nucleic acid molecule according to claim 1, wherein the first stretch of nucleotides comprises 5' $X_1X_2SBBX_3X_4X_5$ 3' (SEQ ID NO: 177) and the fifth stretch of nucleotides comprises 5' $X_6X_7$ $X_8VVSX_9X_{10}$ 3' (SEQ ID NO: 178), wherein $X_1$ is G or absent,
$X_2$ is U or absent,
$X_3$ is B,
$X_4$ is Y,
$X_5$ is M,
$X_6$ is K,
$X_7$ is G,
$X_8$ is N,
$X_9$ is A or absent, and
$X_{10}$ is C or absent.

61. The nucleic acid molecule according to claim 1, wherein the first stretch of nucleotides comprises a nucleotide sequence of 5' $X_1X_2GCYX_3X_4X_5$ 3' (SEQ ID NO:179) and the fifth stretch of nucleotides comprises a nucleotide sequence of 5' $X_6X_7X_8AGCX_9X_{10}$ 3' (SEQ ID NO:180), wherein $X_1$ is G or absent,
$X_2$ is U or absent,
$X_3$ is G,
$X_4$ is C,
$X_5$ is absent,
$X_6$ is absent,
$X_7$ is G,
$X_8$ is C,
$X_9$ is A or absent, and
$X_{10}$ is C or absent.

62. The nucleic acid molecule according to claim 1, wherein the first stretch of nucleotides comprises 5' $X_1X_2SBBX_3X_4X_5$ 3' (SEQ ID NO: 194) and the fifth stretch of nucleotides comprises 5' $X_6X_7X_8VVSX_9X_{10}$ 3' (SEQ ID NO: 201), wherein $X_1$ is G or absent,
$X_2$ is U or absent,
$X_3$ is B,
$X_4$ is Y,
$X_5$ is absent,
$X_6$ is absent,
$X_7$ is G,
$X_8$ is N,
$X_9$ is A or absent, and
$X_{10}$ is C or absent.

63. The nucleic acid molecule according to claim 1, wherein the first stretch of nucleotides comprises 5' $X_1X_2SBBX_3X_4X_5$ 3' (SEQ ID NO: 195) and the fifth stretch of nucleotides comprises 5' $X_6X_7$ $X_8VVSX_9X_{10}$ 3' (SEQ ID NO: 202), wherein $X_1$ is G or absent,
$X_2$ is U or absent,
$X_3$ is B,
$X_4$ is absent,
$X_5$ is M,
$X_6$ is K,
$X_7$ is absent,
$X_8$ is N,
$X_9$ is A or absent, and
$X_{10}$ is C or absent.

64. The nucleic acid molecule according to claim 1, wherein the first stretch of nucleotides comprises 5'

$X_1X_2SBBX_3X_4X_5$ 3' (SEQ ID NO: 196) and the fifth stretch of nucleotides comprises 5' $X_6X_7$ $X_8VVSX_9X_{10}$ 3' (SEQ ID NO: 203), wherein $X_1$ is G or absent,
$X_2$ is U or absent,
$X_3$ is absent,
$X_4$ is Y,
$X_5$ is M,
$X_6$ is K,
$X_7$ is G,
$X_8$ is absent,
$X_9$ is A or absent, and
$X_{10}$ is C or absent.

65. The nucleic acid molecule according to claim 1, wherein the first stretch of nucleotides comprises 5' $X_1X_2SBBX_3X_4X_5$ 3' (SEQ ID NO: 198) and the fifth stretch of nucleotides comprises 5' $X_6X_7$ $X_8VVSX_9X_{10}$ 3' (SEQ ID NO:205), wherein $X_1$ is G or absent,
$X_2$ is U or absent,
$X_3$ is absent,
$X_4$ is absent,
$X_5$ is M,
$X_6$ is K,
$X_7$ is absent,
$X_8$ is absent,
$X_9$ is A or absent, and
$X_{10}$ is C or absent.

66. The nucleic acid molecule according to claim 1, wherein the first stretch of nucleotides comprises 5' $X_1X_2SBBX_3X_4X_5$ 3' (SEQ ID NO: 199) and the fifth stretch of nucleotides comprises 5' $X_6X_7X_8VVSX_9X_{10}$ 3' (SEQ ID NO:206), wherein $X_1$ is G or absent,
$X_2$ is U or absent,
$X_3$ is absent,
$X_4$ is Y,
$X_5$ is absent,
$X_6$ is absent,
$X_7$ is G,
$X_8$ is absent,
$X_9$ is A or absent, and
$X_{10}$ is C or absent.

67. The nucleic acid molecule according to claim 1, wherein the first stretch of nucleotides comprises 5' $X_1X_2SBBX_3X_4X_5$ 3' (SEQ ID NO: 200) and the fifth stretch of nucleotides comprises 5' $X_6X_7X_8VVSX_9X_{10}$ 3' (SEQ ID NO: 207), wherein $X_1$ is G or absent,
$X_2$ is U or absent,
$X_3$ is absent,
$X_4$ is absent,
$X_5$ is absent,
$X_6$ is absent,
$X_7$ is absent,
$X_8$ is absent,
$X_9$ is A or absent, and
$X_{10}$ is C or absent.

* * * * *

SEQUENCE LISTING

```
<160> NUMBER OF SEQ ID NOS: 247

<210> SEQ ID NO 1
<211> LENGTH: 74
<212> TYPE: PRT
<213> ORGANISM: Homo sapiens

<400> SEQUENCE: 1

Thr Leu Gln Lys Lys Ile Glu Glu Ile Ala Ala Lys Tyr Lys His Ser
1               5                   10                  15

Val Val Lys Lys Cys Cys Tyr Asp Gly Ala Cys Val Asn Asn Asp Glu
            20                  25                  30

Thr Cys Glu Gln Arg Ala Ala Arg Ile Ser Leu Gly Pro Arg Cys Ile
        35                  40                  45

Lys Ala Phe Thr Glu Cys Cys Val Val Ala Ser Gln Leu Arg Ala Asn
    50                  55                  60

Ile Ser His Lys Asp Met Gln Leu Gly Arg
65                  70


<210> SEQ ID NO 2
<211> LENGTH: 74
<212> TYPE: PRT
<213> ORGANISM: Homo sapiens

<400> SEQUENCE: 2
```

```
Thr Leu Gln Lys Lys Ile Glu Glu Ile Ala Ala Lys Tyr Lys His Ser
1               5                   10                  15

Val Val Lys Lys Cys Cys Tyr Asp Gly Ala Ala Val Asn Asn Asp Glu
            20                  25                  30

Thr Cys Glu Gln Arg Ala Ala Arg Ile Ser Leu Gly Pro Arg Cys Ile
        35                  40                  45

Lys Ala Phe Thr Glu Cys Cys Val Val Ala Ser Gln Leu Arg Ala Lys
    50                  55                  60

Ile Ser His Lys Asp Met Gln Leu Gly Arg
65                  70


<210> SEQ ID NO 3
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3

agcgugcuug uccgauuggc ggcacccuug cgggacuggg gaguacgcu                 49


<210> SEQ ID NO 4
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4

cgugcuuguc cgauuggcgg cacccuugcg ggacugggga guacg                     45


<210> SEQ ID NO 5
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5

gugcuugucc gauuggcggc acccuugcgg gacuggggag uac                       43


<210> SEQ ID NO 6
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6

agcgugcucg uccgauuggc ggcacccuug cgggacuggg gaguacgcu                 49


<210> SEQ ID NO 7
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7

agcgugcuug uccga                                                      15
```

-continued

<210> SEQ ID NO 8
<211> LENGTH: 28
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 8
agcgugcuug uccgauuggc ggcacccu 28

<210> SEQ ID NO 9
<211> LENGTH: 26
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 9
cgugcuuguc cgauuggcgg cacccu 26

<210> SEQ ID NO 10
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 10
cgugcuuguc cgauuggcgg caccc 25

<210> SEQ ID NO 11
<211> LENGTH: 45
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 11
cgcgcuuguc cgauuggcgg cacccuugcg ggacugggga gugcg 45

<210> SEQ ID NO 12
<211> LENGTH: 45
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 12
cgcgcuuguc cgauuggcgg cacccuugcg ggacugggga gcgcg 45

<210> SEQ ID NO 13
<211> LENGTH: 43
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 13
gcgcuugucc gauuggcggc acccuugcgg gacuggggag cgc 43

<210> SEQ ID NO 14

-continued

<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 14
gcgcuugucc gauuggcggc acccu 25

<210> SEQ ID NO 15
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 15
gcgcuugucc gauuggcggc accc 24

<210> SEQ ID NO 16
<211> LENGTH: 11
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 16
gcgcuugucc g 11

<210> SEQ ID NO 17
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 17
gcgcuugucc gauu 14

<210> SEQ ID NO 18
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 18
gcgcuguccg auuggcggca ccc 23

<210> SEQ ID NO 19
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 19
gcgcuugucc gauuggcggc acc 23

<210> SEQ ID NO 20
<211> LENGTH: 31
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 20
guccgauugg cggcacccuu gcgggacugg g 31

<210> SEQ ID NO 21
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
gugcugaaca cgccgcguag gacuucaaug gaguagaaug ggcagcac 48

<210> SEQ ID NO 22
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
gugcugcaac acgccgaaua ggucccgcgc ggaagaaugg ggcagcac 48

<210> SEQ ID NO 23
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
gugccgccag acgccgaaca ggucgcaucg cgaagaaucg ggcagcac 48

<210> SEQ ID NO 24
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
gugcugccag acgccgaaca ggucgcaucg cgaagaaucg gguagcac 48

<210> SEQ ID NO 25
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
gugcugcaag acgccgaaca gguccaggaa gggaagaauc gggcagcac 49

<210> SEQ ID NO 26
<211> LENGTH: 48
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 26
gugcugucag acgccgaaca ggucgcauug cgaagaaucg ggcagcac 48

<210> SEQ ID NO 27
<211> LENGTH: 47
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 27
gugcugcuaa gacgccggau agguccuuuu aggaagaauc ggagcac 47

<210> SEQ ID NO 28
<211> LENGTH: 47
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 28
gugcugcaag acgccgaaua ggaccgaagu guagaaucgu gcagcac 47

<210> SEQ ID NO 29
<211> LENGTH: 48
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 29
gugcugagac gccgaacagg accagcgaaa augguagaau cgcagcac 48

<210> SEQ ID NO 30
<211> LENGTH: 16
<212> TYPE: RNA
<213> ORGANISM: Artificial Sequence
<220> FEATURE:
<223> OTHER INFORMATION: Description of Artificial Sequence: Synthetic
consensus sequence

<400> SEQUENCE: 30
asacgccgvr yaggwc 16

<210> SEQ ID NO 31
<211> LENGTH: 16
<212> TYPE: RNA
<213> ORGANISM: Artificial Sequence
<220> FEATURE:
<223> OTHER INFORMATION: Description of Artificial Sequence: Synthetic
consensus sequence

<400> SEQUENCE: 31
asacgccgmr yaggwc 16

<210> SEQ ID NO 32
<211> LENGTH: 9
<212> TYPE: RNA
<213> ORGANISM: Artificial Sequence
<220> FEATURE:
<223> OTHER INFORMATION: Description of Artificial Sequence: Synthetic
consensus sequence

<400> SEQUENCE: 32 gwagaausg 9

<210> SEQ ID NO 33
<211> LENGTH: 46
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 33
ggcugaacac gccgcguagg acuucaaugg aguagaaugg gcagcc 46

<210> SEQ ID NO 34
<211> LENGTH: 44
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 34
gcugaacacg ccgcguagga cuucaaugga guagaauggg cagc 44

<210> SEQ ID NO 35
<211> LENGTH: 42
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 35
cugaacacgc cgcguaggac uucaauggag uagaaugggc ag 42

<210> SEQ ID NO 36
<211> LENGTH: 44
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 36
ggcugaacac gccgcguagg acccaauggg uagaaugggc agcc 44

<210> SEQ ID NO 37
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 37
ggcugaacac gccgcguagg accc 24

<210> SEQ ID NO 38
<211> LENGTH: 42
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 38
gcugaacacg ccgcguagga cccaaugggu agaaugggca gc 42

<210> SEQ ID NO 39
<211> LENGTH: 42
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 39
gcggaacacg ccgcguagga cccaaugggu agaaugggcc gc 42

<210> SEQ ID NO 40
<211> LENGTH: 42
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 40
gcugcacacg ccgcguagga cccaaugggu agaaugggca gc 42

<210> SEQ ID NO 41
<211> LENGTH: 74
<212> TYPE: PRT
<213> ORGANISM: Bos taurus

<400> SEQUENCE: 41

```
Met Leu Lys Lys Lys Ile Glu Glu Glu Ala Ala Lys Tyr Arg Asn Ala
1               5                   10                  15

Trp Val Lys Lys Cys Cys Tyr Asp Gly Ala His Arg Asn Asp Asp Glu
            20                  25                  30

Thr Cys Glu Glu Arg Ala Ala Arg Ile Ala Ile Gly Pro Glu Cys Ile
        35                  40                  45

Lys Ala Phe Lys Ser Cys Cys Ala Ile Ala Ser Gln Phe Arg Ala Asp
    50                  55                  60

Glu His His Lys Asn Met Gln Leu Gly Arg
65                  70
```

<210> SEQ ID NO 42
<211> LENGTH: 74
<212> TYPE: PRT
<213> ORGANISM: Sus scrofa

<400> SEQUENCE: 42

```
Met Leu Gln Lys Lys Ile Glu Glu Glu Ala Ala Lys Tyr Lys Tyr Ala
1               5                   10                  15

Met Leu Lys Lys Cys Cys Tyr Asp Gly Ala Tyr Arg Asn Asp Asp Glu
            20                  25                  30

Thr Cys Glu Glu Arg Ala Ala Arg Ile Lys Ile Gly Pro Lys Cys Val
        35                  40                  45

Lys Ala Phe Lys Asp Cys Cys Tyr Ile Ala Asn Gln Val Arg Ala Glu
    50                  55                  60

Gln Ser His Lys Asn Ile Gln Leu Gly Arg
65                  70
```

<210> SEQ ID NO 43
<211> LENGTH: 42
<212> TYPE: RNA
<213> ORGANISM: Artificial Sequence -continued
<220> FEATURE:
<223> OTHER INFORMATION: Description of Artificial Sequence: Synthetic
oligonucleotide

<400> SEQUENCE: 43
ggcuaacacg ccgcguagga cccaaugggu agaaugggag cc 42

<210> SEQ ID NO 44
<211> LENGTH: 42
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 44
ggccaacacg ccgcguagga cccaaugggu agaauggggg cc 42

<210> SEQ ID NO 45
<211> LENGTH: 42
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 45
gcccaacacg ccgcguagga cccaaugggu agaauggggg gc 42

<210> SEQ ID NO 46
<211> LENGTH: 42
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 46
cgccaacacg ccgcguagga cccaaugggu agaauggggg cg 42

<210> SEQ ID NO 47
<211> LENGTH: 42
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 47
ccggaacacg ccgcguagga cccaaugggu agaaugggcc gg 42

<210> SEQ ID NO 48
<211> LENGTH: 42
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 48
cgggaacacg ccgcguagga cccaaugggu agaaugggcc cg 42

<210> SEQ ID NO 49
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 49
gcugggcgug uuuacuugcu uaauaggggg cccagc 36

<210> SEQ ID NO 50
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 50
gcugggcgug uuuacuugcu uaauaggggu cccagc 36

<210> SEQ ID NO 51
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 51
gcugggcgug uuuacuugcu uaauaggggg ccuagc 36

<210> SEQ ID NO 52
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 52
gcugggcgug uuuauuugcu uaauaggggg uccagc 36

<210> SEQ ID NO 53
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 53
gcugggcgug uuuacuugcu uaauagggag cccagc 36

<210> SEQ ID NO 54
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 54
gcugggcgug uuuacucgcu uaauagggga cccagc 36

<210> SEQ ID NO 55
<211> LENGTH: 38
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 55
gcuggggagu guuuacuugc uuaauagggg uccccagc 38

<210> SEQ ID NO 56
<211> LENGTH: 38
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 56
gcuggggagu guuuacuugc uuaauagggg uccucagc 38

<210> SEQ ID NO 57
<211> LENGTH: 38
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 57
gcuggggagu guuuacuugc uuaauaggga uccuuagc 38

<210> SEQ ID NO 58
<211> LENGTH: 38
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 58
gcugaggagu guuuacuugc uuaauagggg uccccagc 38

<210> SEQ ID NO 59
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 59
guguuuayuy gcuuaauagg gr 22

<210> SEQ ID NO 60
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 60
guguuuacuu gcuuaauagg gg 22

<210> SEQ ID NO 61
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 61
cguggcgugu uuacuugcuu aauaggggc cacg 34

<210> SEQ ID NO 62
<211> LENGTH: 34
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 62
ccgcgcgugu uuacuugcuu aauaggggc gcgg 34

<210> SEQ ID NO 63
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 63
ugggcguguu uacuugcuua auagggggcc ca 32

<210> SEQ ID NO 64
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 64
cgggcguguu uacuugcuua auagggggcc cg 32

<210> SEQ ID NO 65
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 65
ggggcguguu uacuugcuua auagggggcc cc 32

<210> SEQ ID NO 66
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 66
ggggaguguu uacuugcuua auaggggucc cc 32

<210> SEQ ID NO 67
<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 67
gggcguguuu acuugcuuaa uagggggccc 30

<210> SEQ ID NO 68
<211> LENGTH: 30
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 68
gggaguguuu acuugcuuaa uaggggeccc 30

<210> SEQ ID NO 69
<211> LENGTH: 48
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 69
guacugcguu cggacguggc auguuccuug acaaacgguu ggcaguac 48

<210> SEQ ID NO 70
<211> LENGTH: 48
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 70
gugcugcguu cggacguggc auguuccuug acaaacgguu ggcagcac 48

<210> SEQ ID NO 71
<211> LENGTH: 48
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 71
gugcuggguu cggacguggc auguuccuug auaaacgguu gccagcac 48

<210> SEQ ID NO 72
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 72
guucggacgu ggcauguucc uugayaaacg guug 34

<210> SEQ ID NO 73
<211> LENGTH: 48
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 73
guguugcgua gaauggacau agaggacacg ccgcgcagga cgcagcac 48

<210> SEQ ID NO 74

<211> LENGTH: 48
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 74
gugcugcgaa gaauggacaa aucguacacg ccgagcaggu cgcaguac 48

<210> SEQ ID NO 75
<211> LENGTH: 48
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 75
gugcuggaca ggaccaaggu aagggcggac cgaaaaaccu agcagcac 48

<210> SEQ ID NO 76
<211> LENGTH: 49
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 76
agcgugaaca cgccgaauag guccuauagg ugggaagaau gggcacgcu 49

<210> SEQ ID NO 77
<211> LENGTH: 49
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 77
ccugugcgaa gaaugggccc uagggaacac gccgaaaagg uugcacagg 49

<210> SEQ ID NO 78
<211> LENGTH: 48
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 78
ccugugcgaa gcgcucggcg cauaccgauc agguccggca agcacagg 48

<210> SEQ ID NO 79
<211> LENGTH: 48
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 79
cgugcaacac ggcgaauagc guccuacagu uaggcagaau ggggcacg 48

<210> SEQ ID NO 80
<211> LENGTH: 49
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 80
agcgugcuug uccgauuggc ggcacccuug cgggacuggg gaguacgcu 49

<210> SEQ ID NO 81
<211> LENGTH: 45
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 81
cgugcuuguc cgauuggcgg cacccuugcg ggacugggga guacg 45

<210> SEQ ID NO 82
<211> LENGTH: 43
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 82
gugcuugucc gauuggcggc acccuugcgg gacuggggag uac 43

<210> SEQ ID NO 83
<211> LENGTH: 49
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 83
agcgugcucg uccgauuggc ggcacccuug cgggacuggg gaguacgcu 49

<210> SEQ ID NO 84
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 84
agcgugcuug uccga 15

<210> SEQ ID NO 85
<211> LENGTH: 28
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 85
agcgugcuug uccgauuggc ggcacccu 28

<210> SEQ ID NO 86
<211> LENGTH: 26
<212> TYPE: RNA
<213> ORGANISM: Artificial Sequence
<220> FEATURE:

<223> OTHER INFORMATION: Description of Artificial Sequence: Synthetic oligonucleotide

<400> SEQUENCE: 86
cgugcuuguc cgauuggcgg cacccu 26

<210> SEQ ID NO 87
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 87
cgugcuuguc cgauuggcgg caccc 25

<210> SEQ ID NO 88
<211> LENGTH: 45
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 88
cgcgcuuguc cgauuggcgg cacccuugcg ggacugggga gugcg 45

<210> SEQ ID NO 89
<211> LENGTH: 45
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 89
cgcgcuuguc cgauuggcgg cacccuugcg ggacugggga gcgcg 45

<210> SEQ ID NO 90
<211> LENGTH: 43
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 90
gcgcuugucc gauuggcggc acccuugcgg gacuggggag cgc 43

<210> SEQ ID NO 91
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 91
gcgcuugucc gauuggcggc acccu 25

<210> SEQ ID NO 92
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 92
gcgcuugucc gauuggcggc accc 24

<210> SEQ ID NO 93
<211> LENGTH: 11
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 93
gcgcuugucc g 11

<210> SEQ ID NO 94
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 94
gcgcuugucc gauu 14

<210> SEQ ID NO 95
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 95
gcgcuguccg auuggcggca ccc 23

<210> SEQ ID NO 96
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 96
gcgcuugucc gauuggcggc acc 23

<210> SEQ ID NO 97
<211> LENGTH: 31
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 97
guccgauugg cggcacccuu gcgggacugg g 31

<210> SEQ ID NO 98
<211> LENGTH: 48
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 98
gugcugaaca cgccgcguag gacuucaaug gaguagaaug ggcagcac 48

<210> SEQ ID NO 99
<211> LENGTH: 48
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 99
gugcugcaac acgccgaaua ggucccgcgc ggaagaaugg ggcagcac 48

<210> SEQ ID NO 100
<211> LENGTH: 48
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 100
gugccgccag acgccgaaca ggucgcaucg cgaagaaucg ggcagcac 48

<210> SEQ ID NO 101
<211> LENGTH: 48
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 101
gugcugccag acgccgaaca ggucgcaucg cgaagaaucg gguagcac 48

<210> SEQ ID NO 102
<211> LENGTH: 49
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 102
gugcugcaag acgccgaaca gguccaggaa gggaagaauc gggcagcac 49

<210> SEQ ID NO 103
<211> LENGTH: 48
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 103
gugcugucag acgccgaaca ggucgcauug cgaagaaucg ggcagcac 48

<210> SEQ ID NO 104
<211> LENGTH: 47
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 104
gugcugcuaa gacgccggau agguccuuuu aggaagaauc ggagcac 47

<210> SEQ ID NO 105
<211> LENGTH: 47
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 105
gugcugcaag acgccgaaua ggaccgaagu guagaaucgu gcagcac 47

<210> SEQ ID NO 106
<211> LENGTH: 48
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 106
gugcugagac gccgaacagg accagcgaaa augguagaau cgcagcac 48

<210> SEQ ID NO 107
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 107
asacgccgvr yaggwc 16

<210> SEQ ID NO 108
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 108
asacgccgmr yaggwc 16

<210> SEQ ID NO 109
<211> LENGTH: 9
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 109 gwagaausg 9

<210> SEQ ID NO 110
<211> LENGTH: 46
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 110
ggcugaacac gccgcguagg acuucaaugg aguagaaugg gcagcc 46

<210> SEQ ID NO 111
<211> LENGTH: 44
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 111
gcugaacacg ccgcguagga cuucaaugga guagaauggg cagc 44

<210> SEQ ID NO 112
<211> LENGTH: 42
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 112
cugaacacgc cgcguaggac uucaauggag uagaaugggc ag 42

<210> SEQ ID NO 113
<211> LENGTH: 44
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 113
ggcugaacac gccgcguagg acccaauggg uagaaugggc agcc 44

<210> SEQ ID NO 114
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 114
ggcugaacac gccgcguagg accc 24

<210> SEQ ID NO 115
<211> LENGTH: 42
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 115
gcugaacacg ccgcguagga cccaaugggu agaaugggca gc 42

<210> SEQ ID NO 116
<211> LENGTH: 42
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 116
gcggaacacg ccgcguagga cccaaugggu agaaugggcc gc 42

<210> SEQ ID NO 117
<211> LENGTH: 42

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 117
gcugcacacg ccgcguagga cccaaugggu agaaugggca gc 42

<210> SEQ ID NO 118
<211> LENGTH: 74
<212> TYPE: PRT
<213> ORGANISM: Rattus norvegicus

<400> SEQUENCE: 118

```
Leu Leu His Gln Lys Val Glu Glu Gln Ala Ala Lys Tyr Lys His Arg
1               5                   10                  15

Val Pro Lys Lys Cys Cys Tyr Asp Gly Ala Arg Glu Asn Lys Tyr Glu
            20                  25                  30

Thr Cys Glu Gln Arg Val Ala Arg Val Thr Ile Gly Pro His Cys Ile
        35                  40                  45

Arg Ala Phe Asn Glu Cys Cys Thr Ile Ala Asp Lys Ile Arg Lys Glu
    50                  55                  60

Ser His His Lys Gly Met Leu Leu Gly Arg
65                  70
```

<210> SEQ ID NO 119
<211> LENGTH: 74
<212> TYPE: PRT
<213> ORGANISM: Mus musculus

<400> SEQUENCE: 119

```
Leu Leu Arg Gln Lys Ile Glu Glu Gln Ala Ala Lys Tyr Lys His Ser
1               5                   10                  15

Val Pro Lys Lys Cys Cys Tyr Asp Gly Ala Arg Val Asn Phe Tyr Glu
            20                  25                  30

Thr Cys Glu Glu Arg Val Ala Arg Val Thr Ile Gly Pro Leu Cys Ile
        35                  40                  45

Arg Ala Phe Asn Glu Cys Cys Thr Ile Ala Asn Lys Ile Arg Lys Glu
    50                  55                  60

Ser Pro His Lys Pro Val Gln Leu Gly Arg
65                  70
```

<210> SEQ ID NO 120
<211> LENGTH: 42
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 120
ggcuaacacg ccgcguagga cccaaugggu agaaugggag cc 42

<210> SEQ ID NO 121
<211> LENGTH: 42
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 121

-continued

```
ggccaacacg ccgcguagga cccaaugggu agaauggggg cc                    42


<210> SEQ ID NO 122
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122

gcccaacacg ccgcguagga cccaaugggu agaauggggg gc                    42


<210> SEQ ID NO 123
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123

cgccaacacg ccgcguagga cccaaugggu agaauggggg cg                    42


<210> SEQ ID NO 124
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124

ccggaacacg ccgcguagga cccaaugggu agaaugggcc gg                    42


<210> SEQ ID NO 125
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125

cgggaacacg ccgcguagga cccaaugggu agaaugggcc cg                    42


<210> SEQ ID NO 126
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126

gcugggcgug uuuacuugcu uaauaggggg cccagc                           36


<210> SEQ ID NO 127
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127

gcugggcgug uuuacuugcu uaauaggggu cccagc                           36
```

<210> SEQ ID NO 128
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 128
gcugggcgug uuuacuugcu uaauaggggg ccuagc 36

<210> SEQ ID NO 129
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 129
gcugggcgug uuuauuugcu uaauaggggg uccagc 36

<210> SEQ ID NO 130
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 130
gcugggcgug uuuacuugcu uaauagggag cccagc 36

<210> SEQ ID NO 131
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 131
gcugggcgug uuuacucgcu uaauagggga cccagc 36

<210> SEQ ID NO 132
<211> LENGTH: 38
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 132
gcuggggagu guuuacuugc uuaauagggg uccccagc 38

<210> SEQ ID NO 133
<211> LENGTH: 38
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 133
gcuggggagu guuuacuugc uuaauagggg uccucagc 38

<210> SEQ ID NO 134

<211> LENGTH: 38
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 134
gcuggggagu guuuacuugc uuaauaggga uccuuagc 38

<210> SEQ ID NO 135
<211> LENGTH: 38
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 135
gcugaggagu guuuacuugc uuaauagggg uccccagc 38

<210> SEQ ID NO 136
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 136
guguuuayuy gcuuaauagg gr 22

<210> SEQ ID NO 137
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 137
guguuuacuu gcuuaauagg gg 22

<210> SEQ ID NO 138
<211> LENGTH: 34
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 138
cguggcgugu uuacuugcuu aauagggggc cacg 34

<210> SEQ ID NO 139
<211> LENGTH: 34
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 139
ccgcgcgugu uuacuugcuu aauagggggc gcgg 34

<210> SEQ ID NO 140
<211> LENGTH: 32
<212> TYPE: RNA

-continued

<213> ORGANISM: Artificial Sequence
<220> FEATURE:
<223> OTHER INFORMATION: Description of Artificial Sequence: Synthetic oligonucleotide

<400> SEQUENCE: 140
ugggcguguu uacuugcuua auagggggcc ca 32

<210> SEQ ID NO 141
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 141
cgggcguguu uacuugcuua auagggggcc cg 32

<210> SEQ ID NO 142
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 142
ggggcguguu uacuugcuua auagggggcc cc 32

<210> SEQ ID NO 143
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 143
ggggaguguu uacuugcuua auaggggucc cc 32

<210> SEQ ID NO 144
<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 144
gggcguguuu acuugcuuaa uagggggccc 30

<210> SEQ ID NO 145
<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 145
gggaguguuu acuugcuuaa uaggggaccc 30

<210> SEQ ID NO 146
<211> LENGTH: 48
<212> TYPE: RNA
<213> ORGANISM: Artificial Sequence
<220> FEATURE:

<223> OTHER INFORMATION: Description of Artificial Sequence: Synthetic oligonucleotide

<400> SEQUENCE: 146
guacugcguu cggacguggc auguuccuug acaaacgguu ggcaguac 48

<210> SEQ ID NO 147
<211> LENGTH: 48
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 147
gugcugcguu cggacguggc auguuccuug acaaacgguu ggcagcac 48

<210> SEQ ID NO 148
<211> LENGTH: 48
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 148
gugcuggguu cggacguggc auguuccuug auaaacgguu gccagcac 48

<210> SEQ ID NO 149
<211> LENGTH: 34
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 149
guucggacgu ggcauguucc uugayaaacg guug 34

<210> SEQ ID NO 150
<211> LENGTH: 48
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 150
guguugcgua gaauggacau agaggacacg ccgcgcagga cgcagcac 48

<210> SEQ ID NO 151
<211> LENGTH: 48
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 151
gugcugcgaa gaauggacaa aucguacacg ccgagcaggu cgcaguac 48

<210> SEQ ID NO 152
<211> LENGTH: 48
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 152
gugcuggaca ggaccaaggu aagggcggac cgaaaaaccu agcagcac 48

<210> SEQ ID NO 153
<211> LENGTH: 49
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 153
agcgugaaca cgccgaauag guccuauagg ugggaagaau gggcacgcu 49

<210> SEQ ID NO 154
<211> LENGTH: 49
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 154
ccugugcgaa gaaugggccc uagggaacac gccgaaaagg uugcacagg 49

<210> SEQ ID NO 155
<211> LENGTH: 48
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 155
ccugugcgaa gcgcucggcg cauaccgauc agguccggca agcacagg 48

<210> SEQ ID NO 156
<211> LENGTH: 48
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 156
cgugcaacac ggcgaauagc guccuacagu uaggcagaau ggggcacg 48

<210> SEQ ID NO 157
<211> LENGTH: 51
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 157
ggagcgugcu uguccgauug gcggcacccu ugcgggacug gggaguacgc u 51

<210> SEQ ID NO 158
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 158
gggcgcuugu ccgauuggcg gcacccu 27

<210> SEQ ID NO 159
<211> LENGTH: 46
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 159
ggggcugaac acgccgcgua ggacccaaug gguagaaugg gcagcc 46

<210> SEQ ID NO 160
<211> LENGTH: 44
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 160
gggcugaaca cgccgcguag gacccaaugg guagaauggg cagc 44

<210> SEQ ID NO 161
<211> LENGTH: 38
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 161
gggcugggcg uguuuacuug cuuaauaggg ggcccagc 38

<210> SEQ ID NO 162
<211> LENGTH: 34
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 162
ggugggcgug uuuacuugcu uaauaggggg ccca 34

<210> SEQ ID NO 163
<211> LENGTH: 34
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 163
ggggggcgug uuuacuugcu uaauaggggg cccc 34

<210> SEQ ID NO 164
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 164
gggggcgugu uuacuugcuu aauagggggc cc 32

<210> SEQ ID NO 165
<211> LENGTH: 50
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 165
ggguacugcg uucggacgug gcauguuccu ugacaaacgg uuggcaguac 50

<210> SEQ ID NO 166
<211> LENGTH: 50
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 166
gggugcugcg uucggacgug gcauguuccu ugacaaacgg uuggcagcac 50

<210> SEQ ID NO 167
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 167
gcgcuugucc gauuggcggc acccu 25

<210> SEQ ID NO 168
<211> LENGTH: 44
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 168
ggcugaacac gccgcguagg acccaauggg uagaaugggc agcc 44

<210> SEQ ID NO 169
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 169
gcugggcgug uuuacuugcu uaauaggggg cccagc 36

<210> SEQ ID NO 170
<211> LENGTH: 32
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 170
ggggcguguu uacuugcuua auagggggcc cc 32

<210> SEQ ID NO 171
<211> LENGTH: 999
<212> TYPE: PRT
<213> ORGANISM: Homo sapiens

<400> SEQUENCE: 171

```
Thr Leu Gln Lys Lys Ile Glu Glu Ile Ala Ala Lys Tyr Lys His Ser
1               5                   10                  15

Val Val Lys Lys Cys Cys Tyr Asp Gly Ala Cys Val Asn Asn Asp Glu
            20                  25                  30

Thr Cys Glu Gln Arg Ala Ala Arg Ile Ser Leu Gly Pro Arg Cys Ile
        35                  40                  45

Lys Ala Phe Thr Glu Cys Cys Val Val Ala Ser Gln Leu Arg Ala Asn
    50                  55                  60

Ile Ser His Lys Asp Met Gln Leu Gly Arg Leu His Met Lys Thr Leu
65                  70                  75                  80

Leu Pro Val Ser Lys Pro Glu Ile Arg Ser Tyr Phe Pro Glu Ser Trp
                85                  90                  95

Leu Trp Glu Val His Leu Val Pro Arg Arg Lys Gln Leu Gln Phe Ala
            100                 105                 110

Leu Pro Asp Ser Leu Thr Thr Trp Glu Ile Gln Gly Ile Gly Ile Ser
        115                 120                 125

Asn Thr Gly Ile Cys Val Ala Asp Thr Val Lys Ala Lys Val Phe Lys
    130                 135                 140

Asp Val Phe Leu Glu Met Asn Ile Pro Tyr Ser Val Val Arg Gly Glu
145                 150                 155                 160

Gln Ile Gln Leu Lys Gly Thr Val Tyr Asn Tyr Arg Thr Ser Gly Met
                165                 170                 175

Gln Phe Cys Val Lys Met Ser Ala Val Glu Gly Ile Cys Thr Ser Glu
            180                 185                 190

Ser Pro Val Ile Asp His Gln Gly Thr Lys Ser Ser Lys Cys Val Arg
        195                 200                 205

Gln Lys Val Glu Gly Ser Ser Ser His Leu Val Thr Phe Thr Val Leu
    210                 215                 220

Pro Leu Glu Ile Gly Leu His Asn Ile Asn Phe Ser Leu Glu Thr Trp
225                 230                 235                 240

Phe Gly Lys Glu Ile Leu Val Lys Thr Leu Arg Val Val Pro Glu Gly
                245                 250                 255

Val Lys Arg Glu Ser Tyr Ser Gly Val Thr Leu Asp Pro Arg Gly Ile
            260                 265                 270

Tyr Gly Thr Ile Ser Arg Arg Lys Glu Phe Pro Tyr Arg Ile Pro Leu
        275                 280                 285

Asp Leu Val Pro Lys Thr Glu Ile Lys Arg Ile Leu Ser Val Lys Gly
    290                 295                 300

Leu Leu Val Gly Glu Ile Leu Ser Ala Val Leu Ser Gln Glu Gly Ile
305                 310                 315                 320

Asn Ile Leu Thr His Leu Pro Lys Gly Ser Ala Glu Ala Glu Leu Met
                325                 330                 335

Ser Val Val Pro Val Phe Tyr Val Phe His Tyr Leu Glu Thr Gly Asn
            340                 345                 350

His Trp Asn Ile Phe His Ser Asp Pro Leu Ile Glu Lys Gln Lys Leu
        355                 360                 365

Lys Lys Lys Leu Lys Glu Gly Met Leu Ser Ile Met Ser Tyr Arg Asn
    370                 375                 380

Ala Asp Tyr Ser Tyr Ser Val Trp Lys Gly Gly Ser Ala Ser Thr Trp
```

```
385                 390                 395                 400

Leu Thr Ala Phe Ala Leu Arg Val Leu Gly Gln Val Asn Lys Tyr Val
                405                 410                 415

Glu Gln Asn Gln Asn Ser Ile Cys Asn Ser Leu Leu Trp Leu Val Glu
            420                 425                 430

Asn Tyr Gln Leu Asp Asn Gly Ser Phe Lys Glu Asn Ser Gln Tyr Gln
        435                 440                 445

Pro Ile Lys Leu Gln Gly Thr Leu Pro Val Glu Ala Arg Glu Asn Ser
    450                 455                 460

Leu Tyr Leu Thr Ala Phe Thr Val Ile Gly Ile Arg Lys Ala Phe Asp
465                 470                 475                 480

Ile Cys Pro Leu Val Lys Ile Asp Thr Ala Leu Ile Lys Ala Asp Asn
                485                 490                 495

Phe Leu Leu Glu Asn Thr Leu Pro Ala Gln Ser Thr Phe Thr Leu Ala
            500                 505                 510

Ile Ser Ala Tyr Ala Leu Ser Leu Gly Asp Lys Thr His Pro Gln Phe
        515                 520                 525

Arg Ser Ile Val Ser Ala Leu Lys Arg Glu Ala Leu Val Lys Gly Asn
    530                 535                 540

Pro Pro Ile Tyr Arg Phe Trp Lys Asp Asn Leu Gln His Lys Asp Ser
545                 550                 555                 560

Ser Val Pro Asn Thr Gly Thr Ala Arg Met Val Glu Thr Thr Ala Tyr
                565                 570                 575

Ala Leu Leu Thr Ser Leu Asn Leu Lys Asp Ile Asn Tyr Val Asn Pro
            580                 585                 590

Val Ile Lys Trp Leu Ser Glu Glu Gln Arg Tyr Gly Gly Gly Phe Tyr
        595                 600                 605

Ser Thr Gln Asp Thr Ile Asn Ala Ile Glu Gly Leu Thr Glu Tyr Ser
    610                 615                 620

Leu Leu Val Lys Gln Leu Arg Leu Ser Met Asp Ile Asp Val Ser Tyr
625                 630                 635                 640

Lys His Lys Gly Ala Leu His Asn Tyr Lys Met Thr Asp Lys Asn Phe
                645                 650                 655

Leu Gly Arg Pro Val Glu Val Leu Leu Asn Asp Asp Leu Ile Val Ser
            660                 665                 670

Thr Gly Phe Gly Ser Gly Leu Ala Thr Val His Val Thr Thr Val Val
        675                 680                 685

His Lys Thr Ser Thr Ser Glu Glu Val Cys Ser Phe Tyr Leu Lys Ile
    690                 695                 700

Asp Thr Gln Asp Ile Glu Ala Ser His Tyr Arg Gly Tyr Gly Asn Ser
705                 710                 715                 720

Asp Tyr Lys Arg Ile Val Ala Cys Ala Ser Tyr Lys Pro Ser Arg Glu
                725                 730                 735

Glu Ser Ser Ser Gly Ser Ser His Ala Val Met Asp Ile Ser Leu Pro
            740                 745                 750

Thr Gly Ile Ser Ala Asn Glu Glu Asp Leu Lys Ala Leu Val Glu Gly
        755                 760                 765

Val Asp Gln Leu Phe Thr Asp Tyr Gln Ile Lys Asp Gly His Val Ile
    770                 775                 780

Leu Gln Leu Asn Ser Ile Pro Ser Ser Asp Phe Leu Cys Val Arg Phe
785                 790                 795                 800

Arg Ile Phe Glu Leu Phe Glu Val Gly Phe Leu Ser Pro Ala Thr Phe
                805                 810                 815
```

Thr Val Tyr Glu Tyr His Arg Pro Asp Lys Gln Cys Thr Met Phe Tyr
820 825 830

Ser Thr Ser Asn Ile Lys Ile Gln Lys Val Cys Glu Gly Ala Ala Cys
835 840 845

Lys Cys Val Glu Ala Asp Cys Gly Gln Met Gln Glu Glu Leu Asp Leu
850 855 860

Thr Ile Ser Ala Glu Thr Arg Lys Gln Thr Ala Cys Lys Pro Glu Ile
865 870 875 880

Ala Tyr Ala Tyr Lys Val Ser Ile Thr Ser Ile Thr Val Glu Asn Val
885 890 895

Phe Val Lys Tyr Lys Ala Thr Leu Leu Asp Ile Tyr Lys Thr Gly Glu
900 905 910

Ala Val Ala Glu Lys Asp Ser Glu Ile Thr Phe Ile Lys Lys Val Thr
915 920 925

Cys Thr Asn Ala Glu Leu Val Lys Gly Arg Gln Tyr Leu Ile Met Gly
930 935 940

Lys Glu Ala Leu Gln Ile Lys Tyr Asn Phe Ser Phe Arg Tyr Ile Tyr
945 950 955 960

Pro Leu Asp Ser Leu Thr Trp Ile Glu Tyr Trp Pro Arg Asp Thr Thr
965 970 975

Cys Ser Ser Cys Gln Ala Phe Leu Ala Asn Leu Asp Glu Phe Ala Glu
980 985 990

Asp Ile Phe Leu Asn Gly Cys
995

<210> SEQ ID NO 172
<211> LENGTH: 655
<212> TYPE: PRT
<213> ORGANISM: Homo sapiens

<400> SEQUENCE: 172

Gln Glu Gln Thr Tyr Val Ile Ser Ala Pro Lys Ile Phe Arg Val Gly
1 5 10 15

Ala Ser Glu Asn Ile Val Ile Gln Val Tyr Gly Tyr Thr Glu Ala Phe
20 25 30

Asp Ala Thr Ile Ser Ile Lys Ser Tyr Pro Asp Lys Lys Phe Ser Tyr
35 40 45

Ser Ser Gly His Val His Leu Ser Ser Glu Asn Lys Phe Gln Asn Ser
50 55 60

Ala Ile Leu Thr Ile Gln Pro Lys Gln Leu Pro Gly Gly Gln Asn Pro
65 70 75 80

Val Ser Tyr Val Tyr Leu Glu Val Val Ser Lys His Phe Ser Lys Ser
85 90 95

Lys Arg Met Pro Ile Thr Tyr Asp Asn Gly Phe Leu Phe Ile His Thr
100 105 110

Asp Lys Pro Val Tyr Thr Pro Asp Gln Ser Val Lys Val Arg Val Tyr
115 120 125

Ser Leu Asn Asp Asp Leu Lys Pro Ala Lys Arg Glu Thr Val Leu Thr
130 135 140

Phe Ile Asp Pro Glu Gly Ser Glu Val Asp Met Val Glu Glu Ile Asp
145 150 155 160

His Ile Gly Ile Ile Ser Phe Pro Asp Phe Lys Ile Pro Ser Asn Pro
165 170 175

Arg Tyr Gly Met Trp Thr Ile Lys Ala Lys Tyr Lys Glu Asp Phe Ser
180 185 190

-continued

```
Thr Thr Gly Thr Ala Tyr Phe Glu Val Lys Glu Tyr Val Leu Pro His
        195                 200                 205

Phe Ser Val Ser Ile Glu Pro Glu Tyr Asn Phe Ile Gly Tyr Lys Asn
    210                 215                 220

Phe Lys Asn Phe Glu Ile Thr Ile Lys Ala Arg Tyr Phe Tyr Asn Lys
225                 230                 235                 240

Val Val Thr Glu Ala Asp Val Tyr Ile Thr Phe Gly Ile Arg Glu Asp
                245                 250                 255

Leu Lys Asp Asp Gln Lys Glu Met Met Gln Thr Ala Met Gln Asn Thr
            260                 265                 270

Met Leu Ile Asn Gly Ile Ala Gln Val Thr Phe Asp Ser Glu Thr Ala
        275                 280                 285

Val Lys Glu Leu Ser Tyr Tyr Ser Leu Glu Asp Leu Asn Asn Lys Tyr
    290                 295                 300

Leu Tyr Ile Ala Val Thr Val Ile Glu Ser Thr Gly Gly Phe Ser Glu
305                 310                 315                 320

Glu Ala Glu Ile Pro Gly Ile Lys Tyr Val Leu Ser Pro Tyr Lys Leu
                325                 330                 335

Asn Leu Val Ala Thr Pro Leu Phe Leu Lys Pro Gly Ile Pro Tyr Pro
            340                 345                 350

Ile Lys Val Gln Val Lys Asp Ser Leu Asp Gln Leu Val Gly Gly Val
        355                 360                 365

Pro Val Ile Leu Asn Ala Gln Thr Ile Asp Val Asn Gln Glu Thr Ser
    370                 375                 380

Asp Leu Asp Pro Ser Lys Ser Val Thr Arg Val Asp Asp Gly Val Ala
385                 390                 395                 400

Ser Phe Val Leu Asn Leu Pro Ser Gly Val Thr Val Leu Glu Phe Asn
                405                 410                 415

Val Lys Thr Asp Ala Pro Asp Leu Pro Glu Glu Asn Gln Ala Arg Glu
            420                 425                 430

Gly Tyr Arg Ala Ile Ala Tyr Ser Ser Leu Ser Gln Ser Tyr Leu Tyr
        435                 440                 445

Ile Asp Trp Thr Asp Asn His Lys Ala Leu Leu Val Gly Glu His Leu
    450                 455                 460

Asn Ile Ile Val Thr Pro Lys Ser Pro Tyr Ile Asp Lys Ile Thr His
465                 470                 475                 480

Tyr Asn Tyr Leu Ile Leu Ser Lys Gly Lys Ile Ile His Phe Gly Thr
                485                 490                 495

Arg Glu Lys Phe Ser Asp Ala Ser Tyr Gln Ser Ile Asn Ile Pro Val
            500                 505                 510

Thr Gln Asn Met Val Pro Ser Ser Arg Leu Leu Val Tyr Tyr Ile Val
        515                 520                 525

Thr Gly Glu Gln Thr Ala Glu Leu Val Ser Asp Ser Val Trp Leu Asn
    530                 535                 540

Ile Glu Glu Lys Cys Gly Asn Gln Leu Gln Val His Leu Ser Pro Asp
545                 550                 555                 560

Ala Asp Ala Tyr Ser Pro Gly Gln Thr Val Ser Leu Asn Met Ala Thr
                565                 570                 575

Gly Met Asp Ser Trp Val Ala Leu Ala Ala Val Asp Ser Ala Val Tyr
            580                 585                 590

Gly Val Gln Arg Gly Ala Lys Lys Pro Leu Glu Arg Val Phe Gln Phe
        595                 600                 605

Leu Glu Lys Ser Asp Leu Gly Cys Gly Ala Gly Gly Gly Leu Asn Asn
    610                 615                 620
```

```
Ala Asn Val Phe His Leu Ala Gly Leu Thr Phe Leu Thr Asn Ala Asn
625                 630                 635                 640

Ala Asp Asp Ser Gln Glu Asn Asp Glu Pro Cys Lys Glu Ile Leu
                645                 650                 655


<210> SEQ ID NO 173
<211> LENGTH: 9
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: May or may not be present

<400> SEQUENCE: 173

agcgygcuy                                                                9


<210> SEQ ID NO 174
<211> LENGTH: 9
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (7)..(9)
<223> OTHER INFORMATION: May or may not be present

<400> SEQUENCE: 174

gagyrcgcu                                                                9


<210> SEQ ID NO 175
<211> LENGTH: 7
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(1)
<223> OTHER INFORMATION: May or may not be present

<400> SEQUENCE: 175

cgygcuu                                                                  7


<210> SEQ ID NO 176
<211> LENGTH: 7
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (7)..(7)
<223> OTHER INFORMATION: May or may not be present

<400> SEQUENCE: 176

gagygcg                                                                  7


<210> SEQ ID NO 177
<211> LENGTH: 8
<212> TYPE: RNA
<213> ORGANISM: Artificial Sequence
```

<220> FEATURE:
<223> OTHER INFORMATION: Description of Artificial Sequence: Synthetic oligonucleotide
<220> FEATURE:
<221> NAME/KEY: misc_feature
<222> LOCATION: (1)..(2)
<223> OTHER INFORMATION: May or may not be present

<400> SEQUENCE: 177 gusbbbym 8

<210> SEQ ID NO 178
<211> LENGTH: 8
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (3)..(3)
<223> OTHER INFORMATION: a, c, u, g, unknown or other
<220> FEATURE:
<221> NAME/KEY: misc_feature
<222> LOCATION: (7)..(8)
<223> OTHER INFORMATION: May or may not be present

<400> SEQUENCE: 178 kgnvvsac 8

<210> SEQ ID NO 179
<211> LENGTH: 7
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (1)..(2)
<223> OTHER INFORMATION: May or may not be present

<400> SEQUENCE: 179 gugcygc 7

<210> SEQ ID NO 180
<211> LENGTH: 7
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (6)..(7)
<223> OTHER INFORMATION: May or may not be present

<400> SEQUENCE: 180 gcagcac 7

<210> SEQ ID NO 181
<211> LENGTH: 8
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (1)..(2)
<223> OTHER INFORMATION: May or may not be present

<400> SEQUENCE: 181 gugccgcc 8

<210> SEQ ID NO 182
<211> LENGTH: 8
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (1)..(3)
<223> OTHER INFORMATION: May or may not be present

<400> SEQUENCE: 182 gcbkvggm 8

<210> SEQ ID NO 183
<211> LENGTH: 8
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (6)..(8)
<223> OTHER INFORMATION: May or may not be present

<400> SEQUENCE: 183 dcybhvgc 8

<210> SEQ ID NO 184
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 184
atgctacaag agaagataga ag 22

<210> SEQ ID NO 185
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 185
ctagcatgct taccttccca attgc 25

<210> SEQ ID NO 186
<211> LENGTH: 74
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 186

```
Met Leu Gln Glu Lys Ile Glu Glu Ile Ala Ala Lys Tyr Lys His Leu
1               5                   10                  15

Val Val Lys Lys Cys Cys Tyr Asp Gly Val Arg Ile Asn His Asp Glu
            20                  25                  30
```

```
Thr Cys Glu Gln Arg Ala Ala Arg Ile Ser Val Gly Pro Arg Cys Val
        35                  40                  45

Lys Ala Phe Thr Glu Cys Cys Val Val Ala Ser Gln Leu Arg Ala Asn
    50                  55                  60

Asn Ser His Lys Asp Leu Gln Leu Gly Arg
65                  70


<210> SEQ ID NO 187
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187

ccccggggga uaauucguuc auuugugcgg gg                                32


<210> SEQ ID NO 188
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: May or may not be present

<400> SEQUENCE: 188

gussbs                                                              6


<210> SEQ ID NO 189
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (5)..(6)
<223> OTHER INFORMATION: May or may not be present

<400> SEQUENCE: 189

svssac                                                              6


<210> SEQ ID NO 190
<211> LENGTH: 8
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: May or may not be present

<400> SEQUENCE: 190

agcgygcy                                                            8


<210> SEQ ID NO 191
<211> LENGTH: 7
<212> TYPE: RNA
<213> ORGANISM: Artificial Sequence
<220> FEATURE:
```

<223> OTHER INFORMATION: Description of Artificial Sequence: Synthetic oligonucleotide
<220> FEATURE:
<221> NAME/KEY: misc_feature
<222> LOCATION: (1)..(1)
<223> OTHER INFORMATION: May or may not be present

<400> SEQUENCE: 191 cgygcuy 7

<210> SEQ ID NO 192
<211> LENGTH: 8
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (6)..(8)
<223> OTHER INFORMATION: May or may not be present

<400> SEQUENCE: 192 ggyrcgcu 8

<210> SEQ ID NO 193
<211> LENGTH: 7
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (7)..(7)
<223> OTHER INFORMATION: May or may not be present

<400> SEQUENCE: 193 gagyrcg 7

<210> SEQ ID NO 194
<211> LENGTH: 7
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (1)..(2)
<223> OTHER INFORMATION: May or may not be present

<400> SEQUENCE: 194 gusbbby 7

<210> SEQ ID NO 195
<211> LENGTH: 7
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (1)..(2)
<223> OTHER INFORMATION: May or may not be present

<400> SEQUENCE: 195 gusbbbm 7

<210> SEQ ID NO 196
<211> LENGTH: 7
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (1)..(2)
<223> OTHER INFORMATION: May or may not be present

<400> SEQUENCE: 196 gusbbym 7

<210> SEQ ID NO 197
<211> LENGTH: 6
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (1)..(2)
<223> OTHER INFORMATION: May or may not be present

<400> SEQUENCE: 197 gusbbb 6

<210> SEQ ID NO 198
<211> LENGTH: 6
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (1)..(2)
<223> OTHER INFORMATION: May or may not be present

<400> SEQUENCE: 198 gusbbm 6

<210> SEQ ID NO 199
<211> LENGTH: 6
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (1)..(2)
<223> OTHER INFORMATION: May or may not be present

<400> SEQUENCE: 199 gusbby 6

<210> SEQ ID NO 200
<211> LENGTH: 5
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (1)..(2)
<223> OTHER INFORMATION: May or may not be present

<400> SEQUENCE: 200 gusbb 5

<210> SEQ ID NO 201
<211> LENGTH: 7
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (2)..(2)
<223> OTHER INFORMATION: a, c, u, g, unknown or other
<220> FEATURE:
<221> NAME/KEY: misc_feature
<222> LOCATION: (6)..(7)
<223> OTHER INFORMATION: May or may not be present

<400> SEQUENCE: 201 gnvvsac 7

<210> SEQ ID NO 202
<211> LENGTH: 7
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (2)..(2)
<223> OTHER INFORMATION: a, c, u, g, unknown or other
<220> FEATURE:
<221> NAME/KEY: misc_feature
<222> LOCATION: (6)..(7)
<223> OTHER INFORMATION: May or may not be present

<400> SEQUENCE: 202 knvvsac 7

<210> SEQ ID NO 203
<211> LENGTH: 7
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (6)..(7)
<223> OTHER INFORMATION: May or may not be present

<400> SEQUENCE: 203 kgvvsac 7

<210> SEQ ID NO 204
<211> LENGTH: 6
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (1)..(1)
<223> OTHER INFORMATION: a, c, u, g, unknown or other
<220> FEATURE:
<221> NAME/KEY: misc_feature
<222> LOCATION: (5)..(6)
<223> OTHER INFORMATION: May or may not be present

<400> SEQUENCE: 204 nvvsac 6

<210> SEQ ID NO 205
<211> LENGTH: 6
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (5)..(6)
<223> OTHER INFORMATION: May or may not be present

<400> SEQUENCE: 205 kvvsac 6

<210> SEQ ID NO 206
<211> LENGTH: 6
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (5)..(6)
<223> OTHER INFORMATION: May or may not be present

<400> SEQUENCE: 206 gvvsac 6

<210> SEQ ID NO 207
<211> LENGTH: 5
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (4)..(5)
<223> OTHER INFORMATION: May or may not be present

<400> SEQUENCE: 207 vvsac 5

<210> SEQ ID NO 208
<211> LENGTH: 4
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 208 ssbs 4

<210> SEQ ID NO 209
<211> LENGTH: 4
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 209 svss 4

<210> SEQ ID NO 210
<211> LENGTH: 7
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: misc_feature
<222> LOCATION: (1)..(2)
<223> OTHER INFORMATION: May or may not be present

<400> SEQUENCE: 210 gugcvgc 7

<210> SEQ ID NO 211
<211> LENGTH: 8
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: misc_feature
<222> LOCATION: (7)..(8)
<223> OTHER INFORMATION: May or may not be present

<400> SEQUENCE: 211 ggcagcac 8

<210> SEQ ID NO 212
<211> LENGTH: 16
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 212
acacgccgcg uaggac 16

<210> SEQ ID NO 213
<211> LENGTH: 9
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 213 guagaaugg 9

<210> SEQ ID NO 214
<211> LENGTH: 7
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: misc_feature
<222> LOCATION: (1)..(3)
<223> OTHER INFORMATION: May or may not be present

<400> SEQUENCE: 214 gcbkvgm 7

<210> SEQ ID NO 215

<211> LENGTH: 7
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 215 gcbkvgm 7

<210> SEQ ID NO 216
<211> LENGTH: 7
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (5)..(7)
<223> OTHER INFORMATION: May or may not be present

<400> SEQUENCE: 216 dybhvgc 7

<210> SEQ ID NO 217
<211> LENGTH: 7
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 217 dybhvgc 7

<210> SEQ ID NO 218
<211> LENGTH: 34
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 218
guucggacgu ggcauguucc uugacaaacg guug 34

<210> SEQ ID NO 219
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 219
gacgccgaac aggac 15

<210> SEQ ID NO 220
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 220
gacgccggau agguc 15

<210> SEQ ID NO 221
<211> LENGTH: 31
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 221
gcggcacccu ugcgggacug gggaguacgc u 31

<210> SEQ ID NO 222
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 222
cgggacuggg gaguacgcu 19

<210> SEQ ID NO 223
<211> LENGTH: 17
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 223
cgggacuggg gaguacg 17

<210> SEQ ID NO 224
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 224
gggacugggg aguacg 16

<210> SEQ ID NO 225
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 225
cgggacuggg gagcgc 16

<210> SEQ ID NO 226
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 226
gggacugggg agcgc 15

<210> SEQ ID NO 227

<211> LENGTH: 11
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 227
uggcggcacc c 11

<210> SEQ ID NO 228
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 228
gggacugggg agcgc 15

<210> SEQ ID NO 229
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 229
gggacugggg agcgc 15

<210> SEQ ID NO 230
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 230
gggacugggg gcgc 14

<210> SEQ ID NO 231
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 231
ggacugggga gcgc 14

<210> SEQ ID NO 232
<211> LENGTH: 17
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 232
ggguagaaug ggcagcc 17

<210> SEQ ID NO 233
<211> LENGTH: 31
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 233
gcggcacccu ugcgggacug gggaguacgc u 31

<210> SEQ ID NO 234
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 234
cgggacuggg gaguacgcu 19

<210> SEQ ID NO 235
<211> LENGTH: 17
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 235
cgggacuggg gaguacg 17

<210> SEQ ID NO 236
<211> LENGTH: 16
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 236
gggacugggg aguacg 16

<210> SEQ ID NO 237
<211> LENGTH: 16
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 237
cgggacuggg gagcgc 16

<210> SEQ ID NO 238
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 238
gggacugggg agcgc 15

<210> SEQ ID NO 239
<211> LENGTH: 11
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 239
uggcggcacc c 11

<210> SEQ ID NO 240
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 240
gggacugggg agcgc 15

<210> SEQ ID NO 241
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 241
gggacugggg agcgc 15

<210> SEQ ID NO 242
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 242
gggacugggg gcgc 14

<210> SEQ ID NO 243
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 243
ggacugggga gcgc 14

<210> SEQ ID NO 244
<211> LENGTH: 17
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 244
ggguagaaug ggcagcc 17

<210> SEQ ID NO 245
<211> LENGTH: 16
<212> TYPE: RNA
<213> ORGANISM: Artificial Sequence
<220> FEATURE:
<223> OTHER INFORMATION: Description of Artificial Sequence: Synthetic
oligonucleotide -continued

```
<400> SEQUENCE: 245

cgggacuggg gagcgc                                                     16


<210> SEQ ID NO 246
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 246

cgggacuggg gagcgc                                                     16


<210> SEQ ID NO 247
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 247

His His His His His His
1               5
```